US005686233A

United States Patent [19]

Valet et al.

[11] Patent Number: 5,686,233
[45] Date of Patent: Nov. 11, 1997

[54] BISRESORCINYLTRIAZINES

[75] Inventors: Andreas Valet, Binzen, Germany; Jean-Luc Birbaum, Kobe, Japan; Vien Van Toan, Lentigny; Walter Knupp, Düdingen, both of Switzerland

[73] Assignee: Ciba-Geigy Corporation, Tarrytown, N.Y.

[21] Appl. No.: 539,150

[22] Filed: Oct. 4, 1995

[30] Foreign Application Priority Data

| Oct. 10, 1994 | [CH] | Switzerland | 3039/94 |
| Feb. 8, 1995 | [CH] | Switzerland | 364/95 |
| Feb. 8, 1995 | [CH] | Switzerland | 365/95 |

[51] Int. Cl.$^6$ .................... G03C 1/815; C08K 5/3492
[52] U.S. Cl. .................... 430/512; 544/113; 544/116; 544/216
[58] Field of Search .................... 430/626, 512; 544/113, 116, 216

[56] References Cited

U.S. PATENT DOCUMENTS

| 3,244,708 | 4/1966 | Duennenberger | 260/248 |
| 3,249,608 | 5/1966 | Beland et al. | 260/248 |
| 3,645,743 | 2/1972 | Mucke et al. | 430/626 |
| 3,843,371 | 10/1974 | Peller et al. | 96/84 |
| 4,220,765 | 9/1980 | Findeisen . | |
| 4,619,956 | 10/1986 | Susi | 524/87 |
| 4,826,978 | 5/1989 | Migdal et al. | 544/216 |
| 5,364,749 | 11/1994 | Leppard et al. | 430/507 |
| 5,438,840 | 8/1995 | Toan et al. | 430/512 |
| 5,489,503 | 2/1996 | Toan | 430/512 |

FOREIGN PATENT DOCUMENTS

| 0002493 | 6/1979 | European Pat. Off. . |
| 0434608 | 6/1991 | European Pat. Off. . |
| 0483488 | 5/1992 | European Pat. Off. . |
| 480090 | 12/1969 | Switzerland . |
| 484695 | 3/1970 | Switzerland . |
| 1321561 | 6/1973 | United Kingdom . |
| 2273498 | 6/1994 | United Kingdom . |
| 2278115 | 11/1994 | United Kingdom . |
| 9405645 | 3/1994 | WIPO . |
| 9418278 | 8/1994 | WIPO . |

OTHER PUBLICATIONS

Chem. Abst. 90534r vol. 72 1970 of Swiss 480,090.
Chem. Abst. 121590m vol. 72 1970 of Swiss 484,695.
Chemical Abstract 213920n—European Patent Application EP 530,135.

Primary Examiner—Thorl Chea
Attorney, Agent, or Firm—Luther A. R. Hall

[57] ABSTRACT

Compounds of the formula I

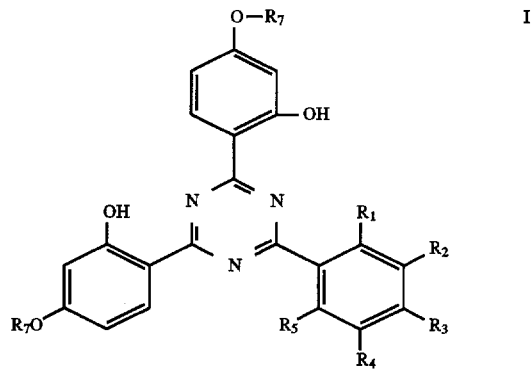

in which $R_1$ and $R_5$, independently of one another, are $C_1$–$C_{12}$alkyl; $R_2$, $R_3$ and $R_4$, independently of one another, are H; $C_1$–$C_{12}$alkyl; $C_2$–$C_6$alkenyl; $C_1$–$C_{12}$alkoxy; $C_2$–$C_{18}$alkenyloxy; halogen; trifluormethyl; $C_7$–$C_{11}$phenylalkyl; phenyl; phenyl which is substituted by $C_1$–$C_{18}$alkyl, $C_1$–$C_{18}$alkoxy or halogen; phenoxy; or phenoxy which is substituted by $C_1$–$C_{18}$alkyl, $C_1$–$C_{18}$alkoxy or halogen; the two radicals $R_7$ are identical or different and are hydrogen or $C_1$–$C_{18}$alkyl; or are $C_1$–$C_{18}$alkyl which is substituted by OH, $C_1$–$C_{18}$alkoxy, $C_3$–$C_6$alkenyloxy, halogen, —COOH, —COOR$_8$, —CONH$_2$, —CONHR$_9$, —CON(R$_9$)(R$_{10}$), —NH$_2$, —NHR$_9$, —N(R$_9$)(R$_{10}$), —NHCOR$_{11}$, —CN, —OCOR$_{11}$, phenoxy and/or phenoxy which is substituted by $C_1$–$C_{18}$alkyl, $C_1$–$C_{18}$alkoxy or halogen; or the radicals $R_7$ are $C_3$–$C_{50}$alkyl which is interrupted by —O— and may be substituted by OH, phenoxy or $C_7$–$C_{18}$alkylphenoxy; or the radicals $R_7$ are $C_3$–$C_6$alkenyl; glycidyl; $C_5$–$C_{12}$cycloalkyl; $C_5$–$C_{12}$cycloalkyl which is substituted by OH, $C_1$–$C_4$alkyl oder —OCOR$_{11}$; $C_7$–$C_{11}$phenylalkyl which is unsubstituted or substituted by OH, Cl or CH$_3$; $C_4$–$C_{14}$alkenyl which is substituted by OH or —OCOR$_{11}$; —CO—R$_{12}$ or —SO$_2$—R$_{13}$; and R$_8$ to R$_{14}$ are as defined in claim 1, are highly suitable for stabilizing organic material, including photographic recording material.

6 Claims, No Drawings

BISRESORCINYLTRIAZINES

The invention relates to novel compounds of the 2,4-bis (2'-hydroxyphenyl)-6-aryl-1,3,5-triazine type, to organic material, in particular a coating material or photographic recording material, stabilized with the aid of these compounds against damage by light, heat and oxygen, and to the corresponding use of the compounds as stabilizers for organic material.

If it is desired to increase the light stability of an organic material, a light stabilizer is usually added. A class of light stabilizers which is very frequently used is the UV absorbers, which protect the material by absorbing the harmful radiation via chromophores. An important group of UV absorbers is the triphenyltriazines, as described, inter alia, in the publications EP-A-434 608, EP-A-520 938, U.S. Pat. No. 4,619,956 and EP-A-483 488. Some bisresorcinyl derivatives from this group are mentioned, for example, in the publications CH-A-480 090, CH-A-484 695, U.S. Pat. Nos. 3,249,608, 3,244,708, 3,843,371, 4,826,978, EP-A-434 608, EP-A-520 938, GB-A-2 273 498 and WO-A-94/18 278.

It has now been found that certain derivatives of 2,4-bis (2'-hydroxyphenyl)-1,3,5-triazine surprisingly have particularly good stabilizer properties.

The invention therefore relates to a compound of the formula I

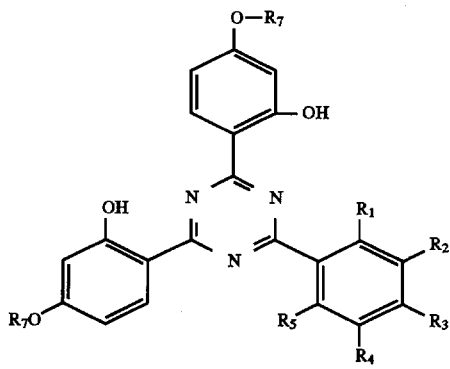

in which
$R_1$ and $R_5$, independently of one another, are $C_1$–$C_{12}$alkyl;

$R_2$, $R_3$ and $R_4$, independently of one another, are H; $C_1$–$C_{12}$alkyl; $C_2$–$C_6$alkenyl; $C_1$–$C_{12}$alkoxy; $C_2$–$C_{18}$alkenyloxy; halogen; trifluormethyl; $C_7$–$C_{11}$phenylalkyl; phenyl; phenyl which is substituted by $C_1$–$C_{18}$alkyl, $C_1$–$C_{18}$alkoxy or halogen; phenoxy; or phenoxy which is substituted by $C_1$–$C_{18}$alkyl, $C_1$–$C_{18}$alkoxy or halogen;

the two radicals $R_7$ are identical or different and are hydrogen or $C_1$–$C_{18}$alkyl; or are $C_1$–$C_{18}$alkyl which is substituted by OH, $C_1$–$C_{18}$alkoxy, $C_3$–$C_6$alkenyloxy, halogen, —COOH, —COOR$_8$, —CONH$_2$, —CONHR$_9$, —CON(R$_9$)(R$_{10}$), —NH$_2$, —NHR$_9$, —N(R$_9$)(R$_{10}$), —NHCOR$_{11}$, —CN, —OCOR$_{11}$, phenoxy and/or phenoxy which is substituted by $C_1$–$C_{18}$alkyl, $C_1$–$C_{18}$alkoxy or halogen; or the radicals $R_7$ are $C_3$–$C_{50}$alkyl which is interrupted by —O— and may be substituted by OH, phenoxy or $C_7$–$C_{18}$alkylphenoxy; or the radicals $R_7$ are $C_3$–$C_6$alkenyl; glycidyl; $C_5$–$C_{12}$cycloalkyl; $C_5$–$C_{12}$cycloalkyl which is substituted by OH, $C_1$–$C_4$alkyl oder —OCOR$_{11}$; $C_7$–$C_{11}$phenylalkyl which is unsubstituted or substituted by OH, Cl or CH$_3$; $C_4$–$C_{14}$alkenyl which is substituted by OH or —OCOR$_{11}$; —CO—R$_{12}$ or —SO$_2$—R$_{13}$;

$R_8$ is $C_1$–$C_{18}$alkyl; $C_2$–$C_{18}$alkenyl; $C_3$–$C_{50}$alkyl which is interrupted by O, NH, NR$_9$ or S and/or is substituted by OH; $C_1$–$C_4$alkyl which is substituted by —P(O)(OR$_{14}$)$_2$, —N(R$_9$)(R$_{10}$) or —OCOR$_{11}$ and/or OH; glycidyl; $C_5$–$C_{12}$cycloalkyl; phenyl; $C_7$–$C_{14}$alkylphenyl or $C_7$–$C_{11}$phenylalkyl;

$R_9$ and $R_{10}$, independently of one another, are $C_1$–$C_{12}$alkyl; $C_3$–$C_{12}$alkoxyalkyl; $C_4$–$C_{16}$dialkylaminoalkyl or $C_5$–$C_{12}$cycloalkyl, or $R_9$ and $R_{10}$ together are $C_3$–$C_9$alkylene or -oxaalkylene or -azaalkylene;

$R_{11}$ is $C_1$–$C_{18}$alkyl, $C_5$–$C_{12}$cycloalkyl or phenyl; or is $C_3$–$C_{50}$alkyl which is interrupted by —O— and may be substituted by OH;

$R_{12}$ is $C_1$–$C_{18}$alkyl; phenyl; $C_5$–$C_{12}$cycloalkyl; $C_1$–$C_{12}$alkoxy; phenoxy; $C_1$–$C_{12}$alkylamino; phenylamino; tolylamino or naphthylamino;

$R_{13}$ is $C_1$–$C_{12}$alkyl; phenyl; naphthyl or $C_7$–$C_{14}$alkylphenyl; and $R_{14}$ is $C_1$–$C_{12}$alkyl or phenyl.

If more than one radical of the same name appears within the same compound, these may be identical or different, within the limits of the possible meanings given; for example, the radicals $R_7$ in a compound of the formula I can have identical or different meanings. In compounds of the formula I, the radicals $R_7$ are preferably identical.

Of particular industrial interest are compounds of the formula I whose hydroxyl groups in the p-position to the triazinyl ring are etherified, i.e. whose radicals $R_7$ are not hydrogen.

A halogen substituent is —F, —Cl, —Br or —I; preferably —F, —Cl or —Br, in particular —Cl.

Alkylphenyl is alkyl-substituted phenyl; $C_7$–$C_{14}$alkylphenyl covers, for example, methylphenyl (tolyl), dimethylphenyl (xylyl), trimethylphenyl (mesityl), ethylphenyl, propylphenyl, butylphenyl, dibutylphenyl, pentylphenyl, hexylphenyl, heptylphenyl and octylphenyl.

Phenylalkyl is phenyl-substituted alkyl; $C_7$–$C_{11}$phenylalkyl covers, for example, benzyl, α-methylbenzyl, α,α-dimethylbenzyl, phenylethyl, phenylpropyl, phenylbutyl and phenylpentyl.

Glycidyl is 2,3-epoxypropyl.

n-Alkyl or alkyl-n is an unbranched alkyl radical.

Alkyl which is interrupted by O, NH, NR$_9$ or S and is unsubstituted or substituted by OH can generally contain one or more of said hetero atoms, although oxygen, nitrogen and sulfur atoms cannot be adjacent to one another. In general, a hetero atom in the alkyl chain and hydroxyl are not vicinal; a carbon atom in the alkyl chain is preferably bonded to at most 1 oxygen, nitrogen or sulfur atom.

Alkyl $R_1$, $R_2$, $R_3$, $R_4$, $R_5$, $R_7$, $R_8$, $R_9$, $R_{10}$, $R_{11}$, $R_{12}$, $R_{13}$ and $R_{14}$ are, within the stated definitions, branched or unbranched alkyl, such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl. Alkyl $R_1$, $R_2$, $R_3$, $R_4$, $R_5$, $R_8$, $R_9$, $R_{10}$, $R_{11}$, $R_{12}$, $R_{13}$ and $R_{14}$ are preferably short-chain, for example $C_1$–$C_8$alkyl, in particular $C_1$–$C_4$alkyl, such as methyl or butyl. $R_1$, $R_3$ and $R_5$ are particularly preferably methyl, ethyl or isopropyl.

$R_2$, $R_3$ and $R_4$ are preferably H, $C_1$–$C_{12}$alkyl, $C_1$–$C_{12}$alkoxy, phenyl or phenyloxy; in particular H, $C_1$–$C_4$alkyl, $C_1$–$C_4$alkoxy or phenyl. $R_2$ and $R_4$ are particularly preferably H, methyl or methoxy, and $R_3$ is in particular $C_1$–$C_4$alkyl or methoxy.

$C_1$–$C_4$Alkyl is, in particular, methyl, ethyl, isopropyl, n-butyl, 2-butyl, 2-methylpropyl or tert-butyl.

$C_4$–$C_{16}$dialkylamino alkyl $R_9$ or $R_{10}$ is dialkylamino-substituted alkyl with a total of from 4 to 16 carbon atoms. Examples thereof are $(CH_3)_2N$—$CH_2CH_2$—; $(C_2H_5)_2N$—$CH_2CH_2$—; $(C_3H_7)_2N$—$CH_2CH_2$—; $(C_4H_9)_2N$—$CH_2CH_2$—; $(C_5H_{11})_2N$—$CH_2CH_2$—; $(C_6H_{13})_2N$—$CH_2CH_2$—; $(CH_3)_2N$—$CH_2CH_2CH_2$—; $(C_2H_5)_2N$—$CH_2CH_2CH_2$—; $(C_3H_7)_2N$—$CH_2CH_2CH_2$—; $(C_4H_9)_2N$—$CH_2CH_2CH_2$—; $(C_5H_{11})_2N$—$CH_2CH_2CH_2$—; $(C_6H_{13})_2N$—$CH_2CH_2CH_2$—.

$R_9$ and $R_{10}$ together as $C_3$–$C_9$alkylene or -oxaalkylene or -azaalkylene are, together with the nitrogen atom to which they are bonded, generally a 5- to 9-membered ring which contains 3 to 9 carbon atoms and may contain further nitrogen or oxygen atoms, although directly adjacent nitrogen and oxygen atoms (structures of the hydrazine, nitrogen oxide or peroxide type) are excluded. Examples thereof include pyrrolidino, piperidino, piperazino and morpholino.

Of particular interest are compounds of the formula I in which the radicals $R_1$, $R_3$ and $R_5$ are identical, in particular those in which $R_2$ and $R_4$ are simultaneously H; particular preference is given to compounds in which $R_1$, $R_3$ and $R_5$ are methyl.

$R_7$ as unsubstituted or substituted $C_5$–$C_{12}$cycloalkyl is, for example, cyclopentyl, cyclohexyl, cycloheptyl, cyclooctyl, cyclododecyl, methylcyclohexyl, hydroxycyclohexyl or acetoxycyclohexyl; cyclohexyl is preferred.

If alkyl radicals carry further substituents or are individual alkylene radicals, free valences and bonds to substituents can emanate from the same or different carbon atoms. Bonds to hetero atoms preferably emanate from different carbon atoms.

Thus, substituted $C_1$–$C_{12}$alkyl $R^7$ includes, for example, hydroxyalkyl, such as 2-hydroxyethyl, 3-hydroxypropyl and 2-hydroxypropyl; alkoxyhydroxyalkyl, such as 2-hydroxy-3-methoxypropyl, 2-hydroxy-3-ethoxypropyl, 2-hydroxy-3-butoxypropyl, 2-hydroxy-3-hexoxypropyl and 2-hydroxy-3-(2-ethylhexyloxy)propyl; alkoxycarbonylalkyl, such as methoxycarbonylmethyl, ethoxycarbonylmethyl, butoxycarbonylmethyl, octyloxycarbonylmethyl, 1-octyloxycarbonyl-1-methylmethyl, 1-octyloxycarbonyl-1-ethylmethyl and 1-octyloxycarbonyl-1-hexylmethyl; and alkanoyloxyalkyl and alkenoyloxyalkyl, such as 2-(acetoxy)ethyl, 2-acryloxyethyl and 2-methacryloxyethyl; and, for example, 3-acrylyloxy- and 3-methacryloxy-2-hydroxypropyl.

$R_7$ as alkyl which is substituted by OH, alkoxy, phenoxy, —$COOR_8$, and/or —$OCOR_{11}$ covers, for example, the following meanings: —$CH_2CH(OH)CH_2O$—$R_{19}$, in which $R_{19}$ is as defined above for alkyl or can be, for example, phenyl, acetyl or propionyl; or alkyloxycarbonylalkyl, for example —$CH(R_{20})$—$(CH_2)_p$—$COOR_8$, in which p is the number 0 or an integer in the range from 1 to 9, and $R_{20}$ is hydrogen or $C_1$–$C_{10}$alkyl, and where the sum of p and the number of carbon atoms in $R_{20}$ is not greater than 17; and $R_8$ is $C_1$–$C_8$alkyl; examples which may be mentioned of such radicals are —$CH_2CH(OH)C_8H_{17}$, —$CH_2CH(OH)C_{12}H_{25}$, —$CH_2CH(OH)CH_2O$-n-$C_8H_{17}$, —$CH_2CH(OH)CH_2O$—$C_6H_5$, —$CH_2CH(OH)CH_2O$—$CH_2CH(C_2H_5)$—$(CH_2)_3$—$CH_3$, —$CH_2CH(OH)CH_2O$—$(CH_2)_{12-14}$—$CH_3$.

$R_7$, $R_8$ and $R_{11}$ as alkyl which is interrupted by O and is unsubstituted or substituted by OH can be interrupted by one or more O atoms and substituted by one or more OH groups.

These radicals are preferably interrupted by a plurality of O atoms, for example 2–12 oxygen atoms, and are unsubstituted or substituted by 1 or 2 OH groups. $R_8$ and $R_{11}$ in this meaning preferably conform to the formula —$(CH_2CHR_{15}$—$O)_n$—$R_{18}$, and $R_7$ preferably conforms to one of the formulae —$(CH_2CHR_{15}$—$O)_n$—$R_{18}$ or —$CH_2$—$CH(OH)$—$CH_2$—$O$—$(CH_2CHR_{15}$—$O)_n$—$R_8$, where n is a number in the range from 1 to 16, in particular in the range from 2 to 12, especially in the range from 4 to 10, $R_{15}$ is H or methyl, and $R_{18}$ is H, $C_1$–$C_{18}$alkyl, phenyl or $C_7$–$C_{10}$alkylphenyl. A typical example of such radicals is polyoxyethylene, for example having 4–10 ethylene oxide units, which carries a free hydroxyl group at the chain end or is saturated by alkyl.

Alkenyl $R_2$, $R_3$, $R_4$, $R_7$, $R_8$ covers, within the stated definitions, inter alia, allyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-octadec-2-enyl and n-octadec-4-enyl.

Compounds of the formula I containing an ethylenic double bond, in particular a conjugated ethylenic double bond, in $R_2$, $R_3$, $R_4$, $R_7$ or $R_8$ are suitable for incorporation into suitable polymers by copolymerization. The incorporation can be carried out, for example, by the processes described in U.S. Pat. No. 5,198,498 or analogously to such processes. The corresponding compounds are therefore of particular interest.

Also of particular industrial interest are compounds of the formula I in which at least one of the radicals $R_2$, $R_3$ and $R_4$ is not H. Also of interest are compounds of the formula I in which 2 of the radicals $R_2$, $R_3$ and $R_4$ or all 3 radicals are different from H.

A subject-matter of particular interest is formed by compounds of the formula I in which $R_1$ and $R_5$, independently of one another, are $C_1$–$C_4$alkyl;

$R_2$, $R_3$ and $R_4$, independently of one another, are H, $C_1$–$C_{12}$alkyl, $C_2$–$C_6$alkenyl, $C_1$–$C_{12}$alkoxy, Cl, F, phenyl or phenoxy; in particular those in which $R_1$ and $R_5$, independently of one another, are $C_1$–$C_4$alkyl; and $R_2$, $R_3$ and $R_4$, independently of one another, are H, $C_1$–$C_6$alkyl, allyl, $C_1$–$C_4$alkoxy, Cl, F or phenyl.

Preference is given to compounds of the formula I in which $R_7$ is hydrogen or $C_1$–$C_{18}$alkyl; or $C_1$–$C_{12}$alkyl which is substituted by OH, $C_1$–$C_{18}$alkoxy, $C_3$–$C_6$alkenyloxy, —Cl, —F, —COOH, —$COOR_8$, —$CONHR_9$, —$CON(R_9)(R_{10})$, —$NH_2$, —$NHR_9$, —$N(R_9)(R_{10})$, —$NHCOR_{11}$, —CN, —$OCOR_{11}$, phenoxy and/or phenoxy which is substituted by $C_1$–$C_{18}$alkyl, $C_1$–$C_{18}$alkoxy or halogen; or the radicals $R_7$ are $C_3$–$C_{50}$alkyl which is interrupted by —O— and may be substituted by OH, phenoxy or $C_7$–$C_{18}$alkylphenoxy; or the radicals $R_7$ are $C_3$–$C_6$alkenyl; glycidyl; $C_5$–$C_{12}$cycloalkyl; $C_5$–$C_{12}$cycloalkyl which is substituted by OH, $C_1$–$C_4$alkyl or —$OCOR_{11}$; $C_7$–$C_{11}$phenylalkyl which is unsubstituted or substituted by OH, Cl or $CH_3$; $C_4$–$C_{14}$alkenyl which is substituted by OH or —$OCOR_{11}$; or —CO—$R_{12}$;

$R_8$ is $C_1$–$C_{18}$alkyl; $C_3$–$C_{18}$alkenyl; $C_3$–$C_{50}$alkyl which is interrupted by O and/or substituted by OH; $C_1$–$C_4$alkyl which is substituted by —$P(O)(OR_{14})_2$, —$N(R_9)(R_{10})$ or —$OCOR_{11}$ and/or OH; glycidyl; $C_5$–$C_{12}$cycloalkyl; phenyl or $C_7$–$C_{11}$phenylalkyl;

$R_{11}$ is $C_1$–$C_{18}$alkyl, cyclohexyl or phenyl; or $C_3$–$C_{50}$alkyl which is interrupted by —O— and may be substituted by OH; and $R_{12}$ is $C_1$–$C_{18}$alkyl; phenyl; cyclohexyl; $C_1$–$C_{12}$alkoxy; phenoxy.

Particular preference is given to compounds of the formula I in which $R_7$ is hydrogen or $C_1$–$C_{18}$alkyl; or $C_1$–$C_{18}$alkyl which is substituted by OH, $C_1$–$C_{18}$alkoxy, $C_3$–$C_6$alkenyloxy, phenoxy, —COOR$_8$, —CONHR$_9$, —CON(R$_9$)(R$_{10}$) and/or —OCOR$_{11}$; or $R_7$ is —(CH$_2$CHR$_{15}$—O)$_n$—R$_{18}$ or —CH$_2$—CH(OH)—CH$_2$—O—(CH$_2$CHR$_{15}$—O)$_n$—R$_{18}$, where n is a number in the range from 1 to 12; or the radicals $R_7$ are $C_3$–$C_6$alkenyl; glycidyl; $C_5$–$C_{12}$cycloalkyl; $C_5$–$C_{12}$cycloalkyl which is substituted by OH or —OCOR$_{11}$; $C_7$–$C_{11}$phenylalkyl; $C_4$–$C_{14}$alkenyl which is substituted by OH or —OCOR$_{11}$; or —CO—R$_{12}$;

$R_8$ is $C_1$–$C_{18}$alkyl; $C_3$–$C_8$alkenyl; $C_3$–$C_{50}$alkyl which is interrupted by O and/or substituted by OH; $C_1$–$C_4$alkyl which is substituted by —P(O)(OR$_{14}$)$_2$ or —OCOR$_{11}$ and/or OH; $C_5$–$C_{12}$cycloalkyl; phenyl or $C_7$–$C_{11}$phenylalkyl;

$R_{11}$ is $C_1$–$C_8$alkyl, cyclohexyl or phenyl;

$R_{12}$ is $C_1$–$C_{18}$alkyl or phenyl;

$R_{14}$ is $C_1$–$C_4$alkyl;

$R_{15}$ is H or methyl; and $R_{18}$ is H, $C_1$–$C_{18}$alkyl, phenyl or $C_7$–$C_{18}$alkylphenyl.

Of these, particular preference is given to compounds of the formula I in which $R_1$ and $R_5$ are methyl;

$R_2$, $R_3$ and $R_4$ are H, $C_1$–$C_4$alkyl, $C_1$–$C_4$alkoxy, —Cl or phenyl;

the radicals $R_7$ are identical and are hydrogen or $C_1$–$C_{18}$alkyl; or $C_1$–$C_{12}$alkyl which is substituted by OH, $C_1$–$C_{18}$alkoxy, $C_3$–$C_5$alkenyloxy, phenoxy, —COOR$_8$ and/or —OCOR$_{11}$; or $R_7$ is —(CH$_2$CHR$_{15}$—O)$_n$—R$_{18}$ or —CH$_2$—CH(OH)—CH$_2$—O—(CH$_2$CHR$_{15}$—O)$_n$—R$_{18}$, where n is a number in the range from 1 to 12; or the radicals $R_7$ are $C_5$–$C_{12}$cycloalkyl;

$C_5$–$C_{12}$cycloalkyl which is substituted by OH; or OH-substituted $C_4$–$C_{14}$alkenyl;

$R_8$ is $C_1$–$C_{12}$alkyl;

$R_{11}$ is $C_1$–$C_4$alkyl; and $R_{18}$ is H or $C_1$–$C_8$alkyl.

Compounds of the formula I in which $R_7$ is $C_1$–$C_{18}$alkyl, $C_5$–$C_{12}$cycloalkyl or a group of one of the formulae —CH$_2$CH(OH)CH$_2$O—R$_{19}$, —CH$_2$CH(OH)R$_{20}$,

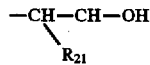

or —C(R$_{22}$)(R$_{23}$)—(CH$_2$)$_p$—COOR$_8$, in which p is the number 0 or an integer in the range from 1 to 9;

$R_8$ is $C_1$–$C_8$alkyl;

$R_{19}$ is $C_1$–$C_{18}$alkyl, $C_3$–$C_5$alkenyl or phenyl;

$R_{20}$ hydrogen, $C_1$–$C_{16}$alkyl or $C_4$–$C_8$alkenyl;

$R_{21}$ is straight-chain $C_4$–$C_{10}$alkylene; and in the case where p is 0, $R_{22}$ and $R_{23}$, independently of one another, are hydrogen or $C_1$–$C_{16}$alkyl, and in the case where p is a number in the range from 1 to 9, $R_{22}$ and $R_{23}$ are hydrogen; in particular those in which $R_1$, $R_3$ and $R_5$ are methyl, and $R_2$ and $R_4$ are hydrogen, represent a subject-matter of very particular interest.

Examples of typical compounds of the formula I are the following (straight-chain radicals denoted by -n):

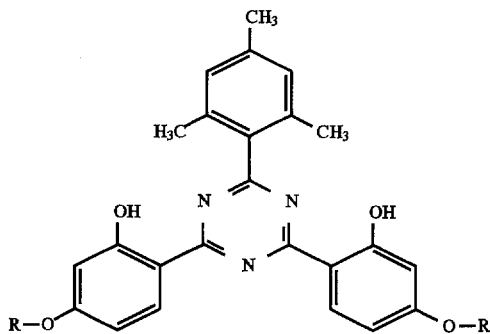

(1) R=CH$_2$—CH(OH)—CH$_2$—O—C$_2$H$_5$
(2) R=CH$_2$—CH(OH)—CH$_2$—O—C$_4$H$_9$-n
(3) R=CH$_2$—CH(OH)—CH$_2$—O—C(CH$_3$)$_3$
(4) R=CH$_2$—CH(OH)—CH$_2$—O—CH$_2$—CH(CH$_3$)—CH$_3$
(4a) R=CH$_2$—CH(OH)—CH$_2$—O—CH(CH$_3$)—C$_2$H$_5$
(5) R=CH$_2$—CH(OH)—CH$_2$—O—(—CH(CH$_3$)—C$_2$H$_5$/—CH(CH$_3$)—C$_3$H$_7$-n) (1:1)
(6) R=CH$_2$—CH(OH)—CH$_2$—O—C$_6$H$_{13}$-n
(7) R=CH$_2$—CH(OH)—CH$_2$—O—CH$_2$—CH(C$_2$H$_5$)—C$_4$H$_9$-n
(8) R=CH$_2$—CH(OH)—CH$_2$—O—C$_{12}$H$_{25}$ (isomer mixture)
(8d) R=CH$_2$—CH(OH)—CH$_2$—O—C$_6$H$_5$
(8x) R=CH$_2$—CH(OH)—CH$_2$—O—(—C$_{12}$H$_{25}$/—C$_{13}$H$_{27}$) (isomer mixture)
(9) R=C$_6$H$_{13}$-n
(10) R=CH$_2$—CH(C$_2$H$_5$)—C$_4$H$_9$-n
(11) R=C$_8$H$_{17}$ (isomer mixture)
(12) R=CH$_2$—CH(OH)—CH$_2$—O—(CH$_2$—CH$_2$—O—)$_{7-8}$—CH$_3$
(13) R=CH(CH$_3$)—CO—O—C$_2$H$_5$
(14) R=CH(C$_4$H$_9$-n)-CO—OC$_2$H$_5$
(15) R=—(CH$_2$)$_5$—CO—O—C$_2$H$_5$
(15a) R=CH(C$_2$H$_5$)—CO—OC$_2$H$_5$
(15b) R=CH(CH$_3$)$_2$—CO—OC$_2$H$_5$
(15c) R=CH(C$_2$H$_5$)—CO—OC$_8$H$_{17}$ (isomer mixture)
(16) R=CH$_2$—CH(O—CO—CH$_3$)—CH$_2$—O—C$_4$H$_9$-n
(17) R=CH$_2$—CH(OH)—CH$_2$—O—CH$_2$—CH=CH$_2$
(20a) R=CH$_2$—CH(OH)—C$_4$H$_9$-n
(20b) R=CH$_2$—CH(OH)—(CH$_2$)$_2$—CH=CH$_2$
(20c) R=CH$_2$—CH(OH)—(CH$_2$)$_6$—CH=CH$_2$
(20d) R=

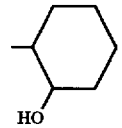

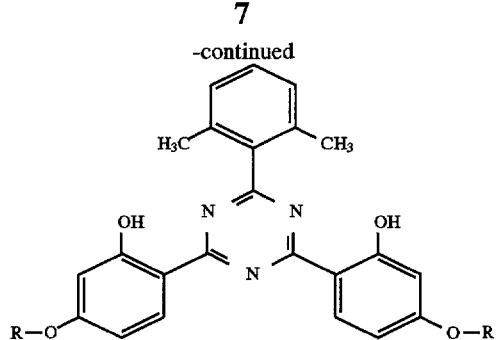

(21) R=CH$_2$—CH(OH)—CH$_2$—O—C$_4$H$_9$-n
(22) R=C$_8$H$_{17}$ (isomer mixture)
(22a) R=C$_6$H$_{13}$-n

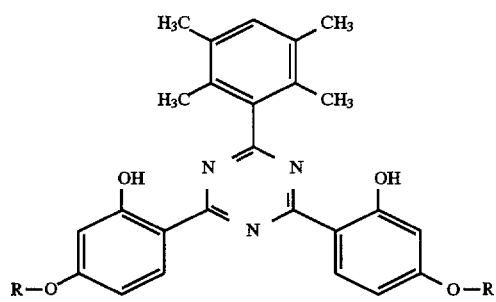

(23) R=CH$_2$—CH(OH)—CH$_2$—O—C$_4$H$_9$-n
(24) R=—(CH$_2$)$_{10}$—CO—O—C$_2$H$_5$

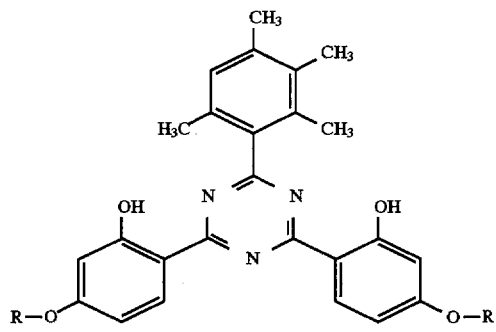

(25) R=CH$_2$—CH(OH)—CH$_2$—O—C$_4$H$_9$-n
(26) R=CH$_2$—CH(OH)—C$_6$H$_{13}$-n

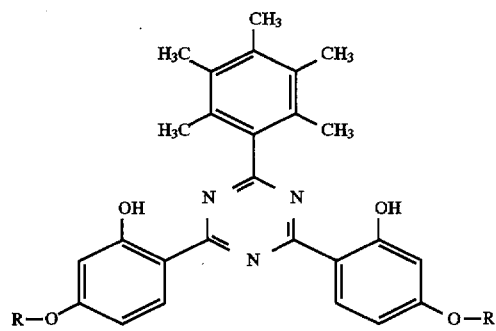

(27) R=CH$_2$—CH(OH)—CH$_2$—O—C$_4$H$_9$-n
(28) R=CH$_2$—CH(OH)—CH$_2$—O—C$_{12}$H$_{25}$ (isomer mixture)

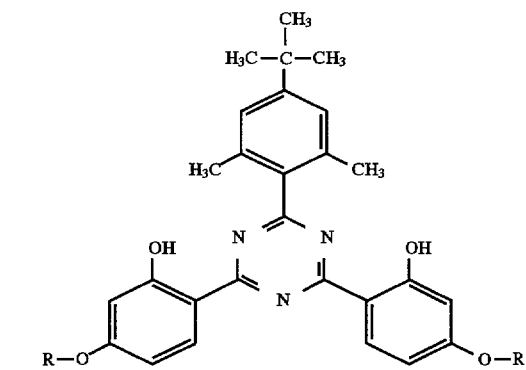

(29) R=CH$_2$—CH(OH)—CH$_2$—O—C$_4$H$_9$-n
(30) R=CH$_2$—CH(OH)—CH$_2$—O—C$_6$H$_5$

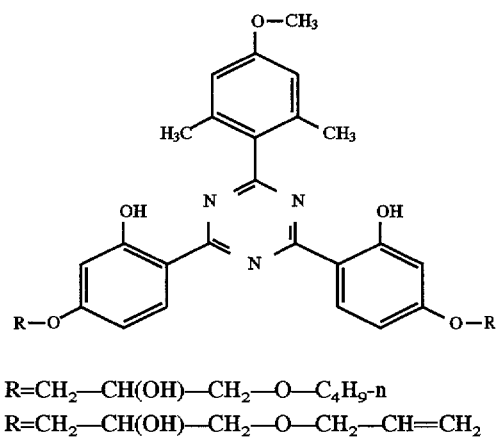

(31) R=CH$_2$—CH(OH)—CH$_2$—O—C$_4$H$_9$-n
(32) R=CH$_2$—CH(OH)—CH$_2$—O—CH$_2$—CH=CH$_2$

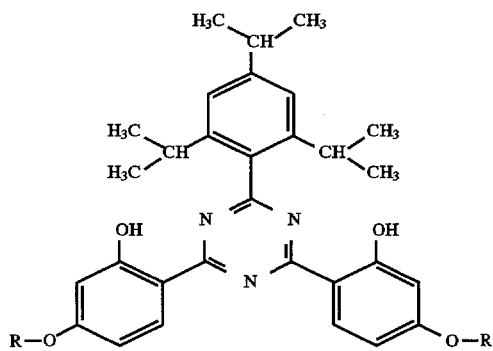

(33) R=CH$_2$—CH(OH)—CH$_2$—O—C$_4$H$_9$-n
(34) R=

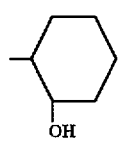

-continued

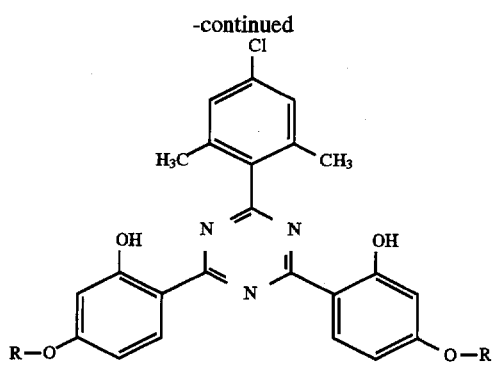

(35) R=CH₂—CH(OH)—CH₂—O—C₄H₉-n
(36) R=C₆H₁₃-n

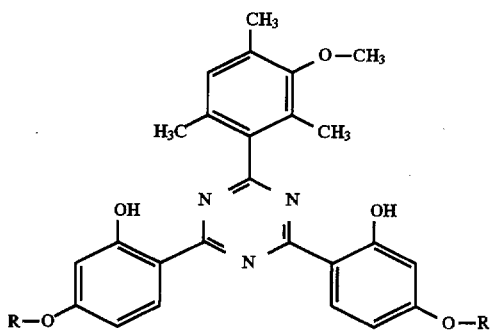

(37) R=CH₂—CH(OH)—CH₂—O—C₄H₉-n.

The compounds of the formula I can be prepared analogously to one of the methods indicated in EP-A-434 608 or in the publication by H. Brunetti and C. E. Lüthi, Helv. Chim. Acta 55, 1566 (1972), by the Friedel-Crafts addition reaction of halotriazines onto corresponding phenols. This can be followed by a further reaction by known methods to give compounds of the formula I in which $R_7$ is not hydrogen; such reactions and processes are described, for example, in EP-A-434 608, page 15, line 11, to page 17, line 1.

The compounds of the formula I are expediently prepared starting from one equivalent of a compound of the formula (A)

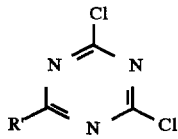
(A)

in which R' is a radical of the formula

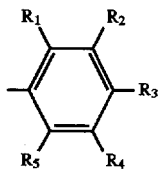

and $R_1$, $R_2$, $R_3$, $R_4$ and $R_5$ are each as defined above under formula I, which is reacted with two equivalents of resorcinol.

The reaction is carried out in a manner known per se by reacting the starting materials in an inert solvent in the presence of anhydrous AlCl₃. Aluminium trichloride and resorcinol are expediently employed in excess; for example, aluminium trichloride can be used in a 5–15% molar excess and the phenol in a 1–30%, in particular in a 5–20% molar excess.

Examples of suitable solvents are hydrocarbons, chlorinated hydrocarbons, SO- or SO₂-containing hydrocarbons or nitrated aromatic hydrocarbons; preference is given to high-boiling hydrocarbons, such as ligroin, petroleum ether, toluene or xylene, or sulfolane.

The temperature is generally not crucial; the process is usually carried out at temperatures from 20° C. to the boiling point of the solvent, for example from 50° C. to 150° C. Work-up can be effected by usual methods, for example by extraction and separation steps, filtration and drying; if necessary, further purification steps, for example recrystallization, can be carried out.

Free phenolic hydroxyl groups of the reaction product in the p-position to the triazinyl ring can subsequently be etherified or esterified in a known manner. In order to prepare the phenol ethers, the free phenols are preferably reacted with epoxides or halides, in particular with glycidyl compounds or with suitable chlorides or bromides.

The starting compounds of the formula (A)

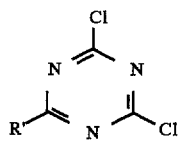
(A)

in which R' is a radical of the formula

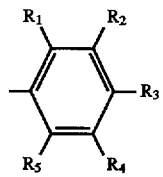

and $R_1$, $R_2$, $R_3$, $R_4$ and $R_5$ are each as defined above under formula I, are likewise novel compounds and, as such, represent a further subject-matter of the invention.

Starting compounds of the formula (A) can be prepared, for example, by reacting cyanuric chloride with an appropriately substituted phenylmagnesium halide (Grignard reaction). The reaction can likewise be carried out in a known manner, for example analogously to the process described in EP-A-577 559. To this end, firstly reaction of a compound of the formula

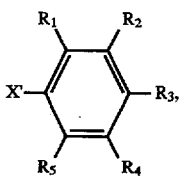

in which X' is Cl or Br, with metallic magnesium in an ether, for example in diethyl ether or in tetrahydrofuran (THF), gives the phenylmagnesium halide. This reagent is subsequently reacted with cyanuric chloride to give the compound of the formula (A), preferably in the absence of oxygen and moisture, for example under nitrogen. The subsequent work-up can again be carried out in a known manner, for example by dilution with an organic solvent, for example toluene, hydrolysis of residual phenylmagnesium halide using aqueous HCl, and separating off, drying and evaporating the organic phase.

The starting compounds of the formula (A) can also be prepared by Friedel-Crafts reaction of a compound of the formula

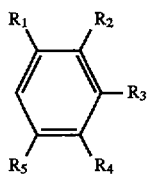

with AlCl₃ and cyanuric chloride, for example analogously to the process described in GB-A-884 802.

Examples of starting compounds of the formula (A) include the following compounds:

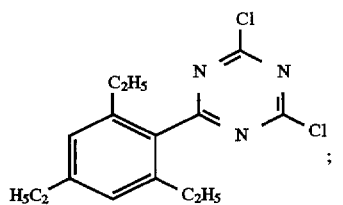

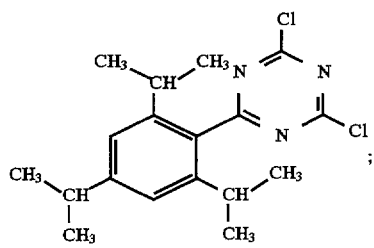

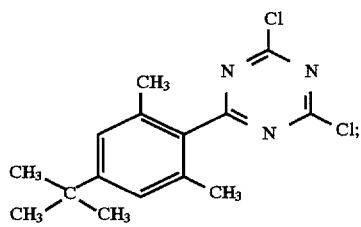

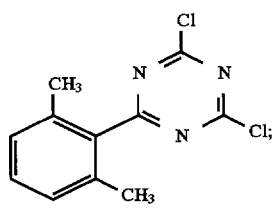

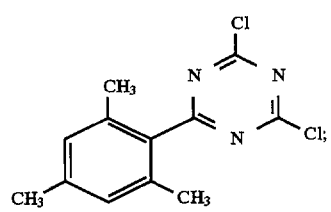

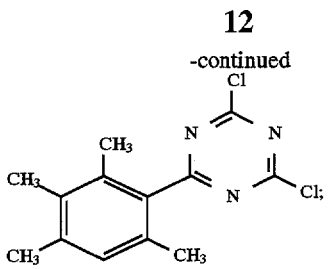

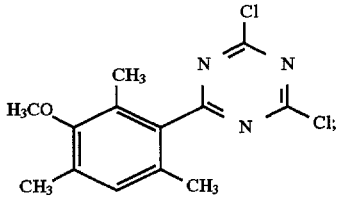

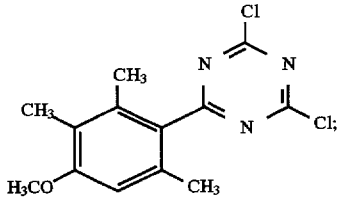

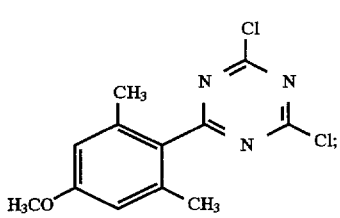

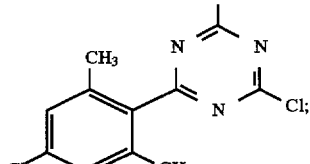

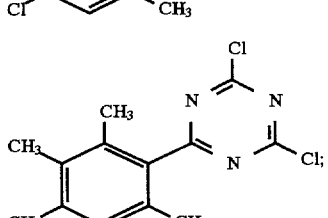

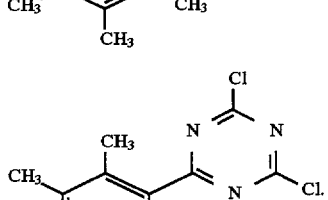

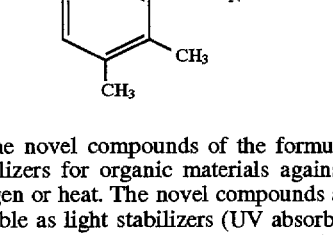

The novel compounds of the formula I can be used as stabilizers for organic materials against damage by light, oxygen or heat. The novel compounds are very particularly suitable as light stabilizers (UV absorbers). Such materials to be stabilized can be, for example, oils, fats, waxes, photographic material, cosmetics or biocides. Of particular interest is use in polymeric materials, as are present in plastics, rubbers, paints and adhesives. Examples of polymers and other substrates which can be stabilized in this manner are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylenelbutylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonilrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 ) above.

12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore also relates to a composition comprising A) an organic material which is sensitive to damage by light, oxygen and/or heat, and B) a compound of the formula I as stabilizer.

The invention also relates to a process for stabilizing organic material against damage by light, oxygen and/or heat, which comprises adding a compound of the formula I thereto as stabilizer, and to the use of compounds of the formula I for stabilizing organic material.

The amount of stabilizer to be used depends on the organic material to be stabilized and on the intended use of the stabilized material. In general, the novel composition comprises from 0.01 to 15 parts by weight, in particular from 0.05 to 10 parts by weight, especially from 0.1 to 5 parts by weight, of the stabilizer (component B) per 100 parts by weight of component A.

The stabilizer (component B) can also be a mixture of two or more novel compounds. The novel compositions can also, in addition to the stabilizer of the formula I, comprise other stabilizers or other additives, for example antioxidants, further light stabilizers, metal deactivators, phosphites or phosphonites. Examples thereof are the following stabilizers:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroguinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate. p0 1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4- octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9 Aromatic hydrobenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β(3,5di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'- phenyl-p-phenylenediamine, N-cyclohexyl-N'-phenyl-p-phenylenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis (phenylamino)propane, (o-tolyl)biguanide, Bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl- phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH₂CH₂—COO(CH₂)₃]₂, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)

ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol disphosphite, bis(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863, 4,338,244, 5,175, 312, 5,216,052, 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5, 7-di-tert-butyl-benzofuran-2-one, 3-(3,5-dimethyl-4-pivaloyloxyphenyl)-5,7-di-tert-butyl-benzofuran-2-one.

The type and amount of the further stabilizers added is determined by the type of substrate to be stabilized and on its intended use; frequently, from 0.1 to 5% by weight, based on the polymer to be stabilized, are used.

The novel compounds of the formula I can particularly advantageously be employed in compositions which comprise, as component A, a synthetic organic polymer, in particular a thermoplastic polymer, a binder for coatings, for example paints, or a photographic material.

Suitable thermoplastic polymers are, for example, polyolefins and polymers containing hetero atoms in the main chain. Preference is also given to compositions in which component A is a thermoplastic polymer containing nitrogen, oxygen and/or sulfur, in particular nitrogen or oxygen, in the main chain.

Polymers containing hetero atoms in the main chain are in particular O-, S- and/or N-containing polymers. Examples of such polymers are the following classes of thermoplastic polymers:

1. Polyacetals, such as polyoxymethylene, and polyoxymethylenes containing comonomers, for example ethylene oxide; polyacetals which have been modified with thermoplastic polyurethanes, acrylates or MBS.
2. Polyphenylene oxides and sulfides, and mixtures thereof with styrene polymers or polyamides.
3. Polyamides and copolyamides, for example those derived from diamines and dicarboxylic acids and/or from aminocarboxylic acids or the corresponding lactams, such as nylon 4, nylon 6, nylon 6/6, 6/10, 6/9, 6/12, 4/6, nylon 11, nylon 12, aromatic polyamides derived from m-xylene, diamine and adipic acid; polyamides prepared from hexamethylenediamine and iso- and/or terephthalic acid and, if desired, an elastomer as modifier, for example poly-2,4,4-trimethylhexamethyleneterephthalamide, poly-m-phenyleneisophthalamide; block copolymers of the abovementioned polyamides with polyolefins, olefin copolymers, ionomers or chemically bonded or grafted elastomers; or with polyethers, for example with polyethylene glycol, polypropylene glycol or polytetramethylene glycol; furthermore polyamides or copolyamides modified with EPDM or ABS; and polyamides condensed during processing ("RIM polyamide systems").
4. Polyureas, polyimides, polyamide-imides and polybenzimidazoles.
5. Polyesters, for example those derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and block polyether-esters derived from polyethers containing hydroxyl terminal groups; furthermore polyesters modified with polycarbonates or MBS.
6. Polycarbonates and polyester carbonates, in particular aromatic polycarbonates, for example those based on 2,2-bis(4-hydroxyphenyl)propane or 1,1-bis(4-hydroxyphenyl)cyclohexane.
7. Polysulfones, polyether sulfones and polyether ketones, in particular aromatic polymers from this class.
8. Mixtures (polyblends) of such polymers with one another or with other polymers, for example with polyolefins, polyacrylates, polydienes or other elastomers as impact modifiers.

Of these, preference is given to polycarbonates, polyesters, polyamides, polyacetals, polyphenylene oxides and polyphenylene sulfides, but in particular to polycarbonates. These are taken to mean, in particular, polymers whose constitutional recurring unit conforms to the formula

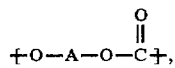

in which A is a divalent phenolic radical. Examples of A are mentioned, inter alia, in U.S. Pat. No. 4,960,863 and DE-A-3 922 496. A can be derived, for example, from hydroquinone, resorcinol, from dihydroxybiphenyls or bisphenols in the broadest sense, such as bis(hydroxyphenyl)alkanes, -cycloalkanes, sulfides, ethers, ketones, sulfones, sulfoxides, α,α'-bis(hydroxyphenyl) diisopropylbenzenes, for example from the compounds 2,2-bis(4-hydroxyphenyl)propane, 2,2-bis(3,5-dimethyl-4-hydroxyphenyl)propane, 2,2-bis(3,5-dichloro-4-hydroxyphenyl)propane, 2,2-bis(3,5-dibromo-4-hydroxyphenyl)propane, 1,1-bis(4-hydroxyphenyl)cyclohexane, or from the compounds of the formulae

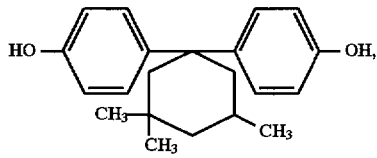

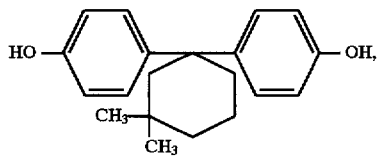

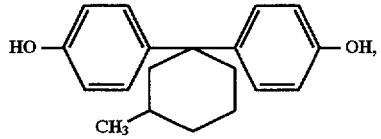

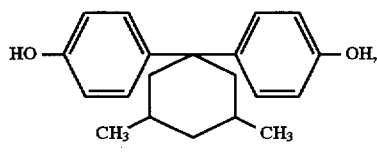

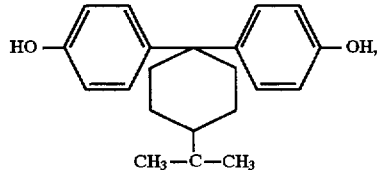

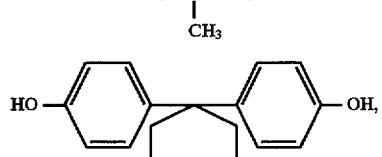

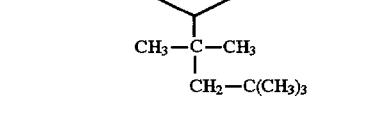

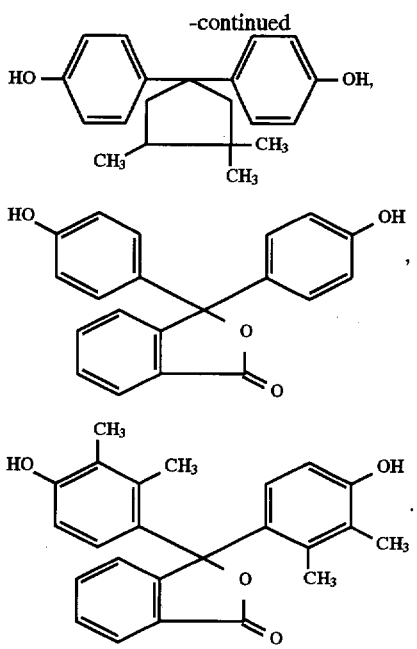

Also of interest are compositions in which component (A) is a polyolefin, for example polyethylene or polypropylene.

Incorporation into the organic polymers, for example in the synthetic organic, in particular thermoplastic polymers, can be carried out by addition of the novel compounds and any further additives by the methods conventional in industry. The incorporation can expediently be carried out before or during shaping, for example by mixing the pulverulent components or by addition of the stabilizer to the melt or solution of the polymers, or by application of the dissolved or dispersed compounds to the polymer, if desired with subsequent evaporation of the solvent. In the case of elastomers, these can also be stabilized as lattices. Another way of incorporating the novel compounds into polymers comprises adding them before or during the polymerization of the corresponding monomers or before the crosslinking.

The novel compounds or mixtures thereof can also be added to the plastics to be stabilized in the form of a masterbatch which comprises these compounds, for example, in a concentration of from 2.5 to 25% by weight.

The novel compounds can expediently be incorporated by the following methods:

- as an emulsion or dispersion (for example to lattices or emulsion polymers)
- as a dry mix during mixing of additional components or polymer mixtures
- by direct addition into the processing equipment (for example extruder, internal mixer, etc.)
- as a solution or melt.

The stabilized polymer compositions obtained in this way can be convened into shaped articles, for example fibres, films, tapes, sheets, sandwich boards, containers, pipes and other profiles, by conventional methods, for example by hot pressing, spinning, extrusion or injection moulding.

The invention therefore furthermore relates to the use of the novel polymer composition for the production of a shaped article.

Also of interest is use in multilayer systems. In this case, a novel polymer composition having a relatively high content of stabilizer of the formula I, for example 5–15% by weight, is applied in a thin film (10–100 μm) to a shaped article made from a polymer containing little or no stabilizer of the formula I. The application can be carried out at the same time as shaping of the base structure, for example by coextrusion. However, the application can also take place to the ready-shaped base structure, for example by lamination with a film or by coating with a solution. The outer layer or layers of the finished article have the function of a UV filter which protects the interior of the article against UV light. The outer layer preferably comprises 5–15% by weight, in particular 5–10% by weight, of at least one stabilizer of the formula I.

The use of the novel polymer composition for the production of multilayer systems in which the outer layer(s) in a thickness of 10–100 μm comprises a novel polymer composition, while the inner layer contains little or no stabilizer of the formula I therefore represents a further subject-matter of the invention.

Of particular interest is the use of a novel polymer composition in which component A is a polycarbonate for the production of multilayer systems.

The polymers stabilized in this way are distinguished by high weathering resistance, in particular by high resistance to UV light. This enables them to retain their mechanical properties and their colour and gloss even when used outside for extended periods.

Likewise of particular interest is the use of the novel compounds of the formula I as stabilizers for coatings, for example for paints. The invention therefore also relates to compositions whose component A is a film-forming binder.

The novel coating composition preferably comprises 0.01–10 parts by weight of B, in particular 0.05–10 parts by weight of B, especially 0.1–5 parts by weight of B, per 100 parts by weight of solid binder A.

Multilayer systems are also possible here, where the concentration of the compound of the formula I (component B) in the outer layer can be higher, for example from 1 to 15 parts by weight of B, especially 3–10 parts by weight of B, per 100 parts by weight of solid binder A.

The use of the novel compound of the formula I as stabilizer in coatings has the additional advantage that delamination, i.e. peeling-off of the coating from the substrate, is prevented. This advantage is particularly important in the case of metallic substrates, including in the case of multilayer systems on metallic substrates.

The binder (component A) can in principle be any binder which is customary in industry, for example those as described in Ullmann's Encyclopedia of Industrial Chemistry, 5th Edn., Vol. A18, pp. 368–426, VCH, Weinheim, 1991. In general, this is a film-forming binder based on a thermoplastic or thermosetting resin, predominantly based on a thermosetting resin. Examples thereof are alkyd, acrylic, polyester, phenolic, melamine, epoxy and polyurethane resins and mixtures thereof.

Component A can be a cold-curable or hot-curable binder; it may be advantageous to add a curing catalyst. Suitable catalysts which accelerate curing of the binder are described, for example, in Ullmann's Encyclopedia of Industrial Chemistry, Vol. A 18, p. 469, VCH Verlagsgesellschaft, Weinheim, 1991.

Preference is given to coating compositions in which component A is a binder comprising a functional acrylate resin and a crosslinking agent.

Examples of coating compositions containing specific binders are:

1. Paints based on cold- or hot-crosslinkable alkyd, acrylate, polyester, epoxy or melamin resins, or mixtures of such resins, if desired with addition of a curing catalyst;
2. Two-component polyurethane paints based on hydroxyl-containing acrylate, polyester or polyether resins and aliphatic or aromatic isocyanates, isocyanurates or polyisocyanates;

3. One-component polyurethane paints based on blocked isocyanates, isocyanurates or polyisocyanates which are deblocked during baking;
4. Two-component paints based on (poly)ketimines and aliphatic or aromatic isocyanates, isocyanurates or polyisocyanates;
5. Two-component paints based on (poly)ketimines and an unsaturated acrylate resin or a polyacetoacetate resin or a methacrylamidoglycolate methyl ester;
6. Two-component paints based on carboxyl- or amino-containing polyacrylates and polyepoxides;
7. Two-component paints based on anhydride-containing acrylate resins and a polyhydroxyl or polyamino component;
8. Two-component paints based on (poly)oxazolines and anhydride-containing acrylate resins or unsaturated acrylate resins or aliphatic or aromatic isocyanates, isocyanurates or polyisocyanates;
9. Two-component paints based on unsaturated polyacrylates and polymalonates;
10. Thermoplastic polyacrylate paints based on thermoplastic acrylate resins or externally crosslinking acrylate resins in combination with etherified melamine resins;
11. Paint systems based on siloxane-modified or fluorine-modified acrylate resins.

The novel coating compositions can also be radiation-curable. In this case, the binder essentially comprises monomeric or oligomeric compounds containing ethylenically unsaturated bonds which are cured, after application, by UV radiation or electron beams, i.e. are converted into a crosslinked, high-molecular-weight form. Corresponding systems are described in the abovementioned publication, Ullmann's Encyclopedia of Industrial Chemistry, 5th Edn. Vol. A18, pages 451–453. In radiation-curable coating compositions, the compounds of the formula I can also be employed without addition of sterically hindered amines.

In addition to components A and B, the novel coating composition preferably comprises, as component C, a light stabilizer of the sterically hindered amine, 2-(2-hydroxyphenyl)-1,3,5-triazine and/or 2-hydroxyphenyl-2H-benztriazole type, for example as mentioned in the above list under points 2.1, 2.6 and 2.8. Of particular industrial interest is the addition of 2-monoresorcinyl-4,6-diaryl-1,3,5-triazines and/or 2-hydroxyphenyl-2H-benzotriazoles.

In order to achieve maximum light stability, it is of particular interest to add sterically hindered amines, as mentioned, for example, in the above list under 2.6. The invention therefore also relates to a coating composition which, in addition to components A and B, comprises, as component C, a light stabilizer of the sterically hindered amine type.

This is preferably a 2,2,6,6-tetraalkylpiperidine derivative containing at least one group of the formula

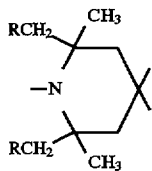

in which R is hydrogen or methyl, in particular hydrogen.

Component C is preferably used in an amount of 0.05–5 parts by weight, based on 100 parts by weight of the solid binder.

Examples of tetraalkylpiperidine derivatives which can be used as component C are given in EP-A-356 677, pages 3–17, sections a) to f). These sections of this EP-A are regarded as part of the present description. It is particularly expedient to employ the following tetraalkylpiperidine derivatives:

bis(2,2,6,6-tetramethylpiperidin-4-yl)succinate,
bis(2,2,6,6-tetramethylpiperidin-4-yl)sebacate,
bis(1,2,2,6,6-pentamethylpiperidin-4-yl)sebacate,
di(1,2,2,6,6-pentamethylpiperidin-4-yl)butyl(3,5-di-tert-butyl-4-hydroxybenzyl)malonate,
bis(1-octyloxy-2,2,6,6-tetramethylpiperidin-4-yl)sebacate,
tetra(2,2,6,6-tetramethylpiperidin-4-yl)butane-1,2,3,4-tetracarboxylate,
tetra(1,2,2,6,6-pentamethylpiperidin-4-yl)butane-1,2,3,4-tetracarboxylate,
2,2,4,4-tetramethyl-7-oxa-3,20-diaza-21-oxodispiro[5.1.11.2]heneicosane,
8-acetyl-3-dodecyl-1,3,8-triaza-7,7,9,9-tetramethylspiro[4,5]decane-2,4-dione, or a compound of the formulae

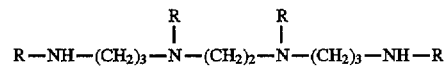

where R=

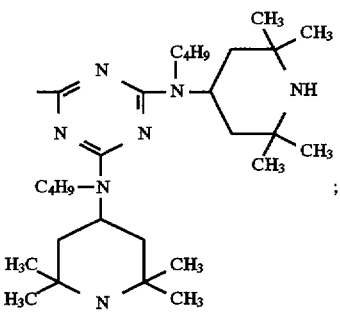

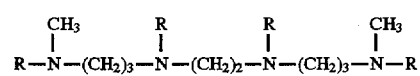

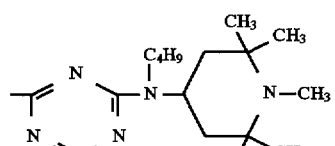

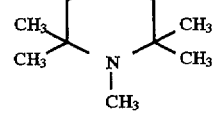

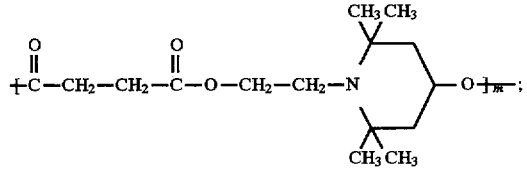

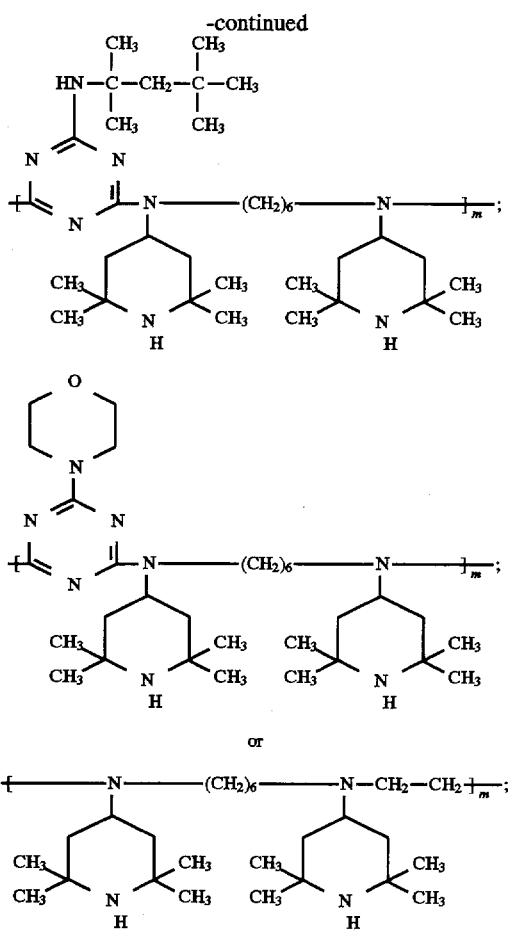

where m has a value of 5-50.

In addition to components A, B and, if used, C, the coating composition can comprise further components, for example solvents, pigments, dyes, plasticizers, stabilizers, thixotropic agents, drying catalysts and/or flow-control agents. Examples of possible components are those as described in Ullmann's Encyclopedia of Industrial Chemistry, 5th Edn., Vol. A18, pp. 429–471, VCH, Weinheim, 1991.

Possible drying catalysts or curing catalysts are, for example, organometallic compounds, amines, amino-containing resins and/or phosphines. Examples of organometallic compounds are metal carboxylates, in particular those of the metals Pb, Mn, Co, Zn, Zr and Cu, or metal chelates, in particular those of the metals Al, Ti and Zr, or organometallic compounds, for example organotin compounds.

Examples of metal carboxylates are the stearates of Pb, Mn and Zn, the octanoates of Co, Zn and Cu, the naphthenates of Mn and Co and the corresponding linoleates, resinates and tallates.

Examples of metal chelates are the aluminium, titanium and zirconium chelates of acetylacetone, ethyl acetylacetate, salicyl aldehyde, salicyl aldoxime, o-hydroxyacetophenone and ethyl trifluoroacetylacetate, and the alkoxides of these metals.

Examples of organotin compounds are dibutyltin oxide, dibutyltin dilaurate and dibutyltin dioctanoate.

Examples of amines are in particular tertiary amines, for example tributylamine, triethanolamine, N-methyldiethanolamine, N-dimethylethanolamine, N-ethylmorpholine, N-methylmorpholine and diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst can also be a phosphine, for example triphenylphosphine.

The novel coating compositions can be applied to any desired substrates, for example to metal, wood, plastic or ceramic materials. They are preferably used as top coat in the painting of automobiles. If the top coat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by conventional processes, for example by brushing, spraying, pouring, dipping or electrophoresis; see also Ullmann's Encyclopedia of Industrial Chemistry, 5th Edn., Vol. A18, pp. 491–500.

The curing of the coatings can—depending on the binder system—be carried out at room temperature or by warming. The coatings are preferably cured at 50°–150° C., powder coatings also at high temperatures.

The coatings obtained in accordance with the invention have excellent resistance to the harmful effects of light, oxygen and heat; particular mention should be made of the good light and weathering resistance of the coatings, for example paints, obtained in this way.

The invention therefore also relates to a coating, in particular a paint, which has been stabilized against the harmful effects of light, oxygen and heat by a content of the novel compound of the formula I. The paint is preferably a top coat for automobiles. The invention furthermore relates to a process for stabilizing a coating based on organic polymers against damage by light, oxygen and/or heat, which comprises admixing a compound of the formula I with the coating composition, and to the use of compounds of the formula I in coating compositions as stabilizers against damage by light, oxygen and/or heat.

A further embodiment of the process uses binders into which a compound of the formula I has been incorporated by copolyaddition or copolycondensation. Suitable compounds of the formula I are for example those in which the radical $R^7$ contains a functional group which is suitable for copolycondensation. In this case, the novel coating composition can also comprise only one component, namely the binder with incorporated stabilizer.

The coating compositions usually comprise an organic solvent or solvent mixture in which the binder is soluble. However, the coating composition can also be an aqueous solution or dispersion. The vehicle can also be a mixture of an organic solvent and water. The coating composition can also be a high-solids paint or contain no solvent (powder paint).

The pigments can be inorganic, organic or metallic pigments. The novel coating compositions preferably contain no pigments and are used as clear coats.

Likewise preferred is the use of the coating composition as top coat for applications in the automobile industry, in particular as a pigmented or unpigmented top coat of the finish. However, use for underlying layers is also possible.

Photographic recording materials are typically based on silver-halide emulsions, silver halide and, in the case of colour-photographic materials, also the dyes or dye precursors being sensitive to UV radiation. In particular UV radiation having a wavelength of from 300 to 400 nm causes the material to change, discolour or bleach. This sensitivity to UV radiation is undesired. The effects mentioned can be suppressed in full or part by adding stabilizers, typically UV absorbers whose absorption maximum is below 400 nm, for example from 300 to 400 nm, to the cyan, magenta and yellow dyes and to the couplers; examples of these UV absorbers are compounds from the 2-hydroxyphenylbenzotriazole class.

However, the use of UV absorbers (UVAs) known hitherto frequently results in undesired effects, for example discolouration and/or spotting, as a consequence of inadequate inherent stability to light, heat or moisture. Furthermore, as a consequence of the high-boiling organic solvent used to prepare the UVA emulsion, softening of the layer and impaired adhesion between the various layers can occur. Compensation for this effect by increasing the gelatin content generally results only in destabilization of the layer, whereas an additional gelatin-protecting layer over the UVA-containing layers causes an undesired increase in the total layer thickness. Other disadvantages of conventional UVA systems can be: migration, surface crystallization or blooming, clumping together and scattering of light at excessively large oil droplets containing the UVAs and prepared by known emulsification methods.

It is known that polymer lattices prepared by polymerization of certain UVA monomers can partly solve the abovementioned problems, as discussed, for example, in EP-A-577 122 for polymeric 2-hydroxyphenylbenzotriazoles.

The use of some UV absorbers of the 2-hydroxyphenyltriazine type in photographic material has also already been proposed (EP-A-530 135, U.S. Pat. No. 5,364,749 and U.S. Pat. No. 5,300,414). Further compounds of this type are described, for example, in EP-A-434 608 and U.S. Pat. No. 5,189,084.

It has now been found that the novel bisresorcinyltriazine UV absorbers of the formula I surprisingly satisfy industrial requirements to a large extent. In particular, these bisresorcinyltriazines have improved inherent stability to light and furthermore are suitable for increasing the stability of the cyan, magenta and yellow layers in photographic materials. The novel photographic materials offer the advantage over known materials stabilized using hydroxyphenyltriazine UV absorbers (for example U.S. Pat. No. 5,364,749) of, for example, low yellowing without impairment of the light-stabilization action.

The novel UV absorbers can be used for photosensitive materials of all types. For example, they can be used for colour paper, colour reversal paper, direct-positive colour materials, colour negative film, colour positive film, colour reversal film, inter alia. They are preferably used, inter alia, for photosensitive colour material which comprises a reversal substrate or forms positives.

These triazines can furthermore advantageously be combined with UV absorbers of the hydroxyphenylbenzotriazole type, in particular representatives thereof which are liquid at room temperature. (cf., for example, U.S. Pat. No. 4,853, 471, U.S. Pat. No. 4,973,702, U.S. Pat. No. 4,921,966 and U.S. Pat. No. 4,973,701).

Combinations of the hydroxyphenyltriazines with UV absorbers of other types, such as benzophenones, oxanilides, cyanoacrylates, salicylates, acrylnitriles or thiazolines, are also suitable for use in photographic recording materials.

The present application thus also relates to photographic recording material comprising, on a base, at least one silver-halide emulsion layer and, if desired, at least one interlayer and/or protection layer, where at least one of said layers contains a UV absorber of the formula I.

The novel photographic recording materials also offer the advantage over materials containing benzotriazole UV absorbers that the UVAs of the formula I are required in a comparatively small amount, so that the thickness of the UVA-containing layer also remains small, which has a positive effect, inter alia, on the imaging properties.

The novel photographic recording materials offer the advantage over materials containing known hydroxyphenyltriazine UVAs, as described, for example, in U.S. Pat. No. 5,364,749, of less yellowing without impairment of the light-stabilization action with respect to the three cyan, magenta and yellow dyes.

The novel photographic recording material can be a black/white or colour material, preferably a colour material.

Examples of colour-photographic materials are colour negative films, colour reversal films, colour positive films, colour-photographic paper, colour reversal photographic paper, colour-sensitive materials for the dye diffusion transfer process or the silver dye bleach process.

Examples of suitable bases for the production of colour-photographic materials are films of semisynthetic and synthetic polymers, such as cellulose nitrate, cellulose acetate, cellulose butyrate, polystyrene, polyvinyl chloride, polyethylene terephthalate and polycarbonate, and paper laminated with a barytes layer or an α-olefin polymer layer (for example polyethylene). These bases can have been coloured with dyes or pigments, for example titanium dioxide. They can also have been coloured black for the purposes of light screening. The surface of the base is generally subjected to a treatment for improving the adhesion of the photographic emulsion layer, for example corona discharge with subsequent application of a substrate layer.

The colour-photographic materials usually contain at least one each of red-sensitive, green-sensitive and blue-sensitive silver halide emulsion layers and, if desired, interlayers and protective layers. The novel material preferably contains the silver-halide emulsion layers from the base in the sequence: blue-sensitive, green-sensitive and red-sensitive layers. The UV absorber in the novel colour-photographic material is preferably in a layer above the green-sensitive layer, particularly preferaemulsion layer above the silver-halide emulsion layer(s).

The novel UV absorber is preferably present in the photographic material in an amaount of from 0.05 to 10 g/m², in particular from 0.1 to 8 g/m², especially from 0.2 to 5 g/m².

An example of a novel colour-photographic recording material is a material having the following layer sequence:

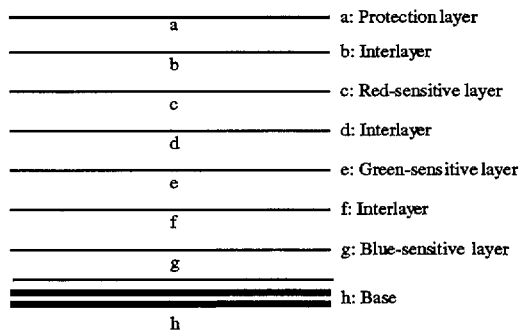

Another example is a material having a similar layer structure, but in which layer a is absent. The novel UV absorber of the formula (I) is, in the layer sequence shown, expediently, for example, in layer b, c and/or d, in particular in b and/or c, especially in b.

Preference is generallay given to a photographic recording material containing a compound of the formula (I) in a layer above the silver-halide emulsion layer(s). Preference is furthermore given to a photographic recording material containing at least one each of red-sensitive and green-sensitive silver-halide emulsion layers and an interlayer in between, where at least one compound of the formula (I) is present in the interlayer between the red-sensitive and green-sensitive silver-halide emulsion layers. Very particular preference is given to a photographic recording material containing at least one each of red-sensitive, green-sensitive and blue-sensitive silver-halide emulsion layers and at least two interlayers between said layers and a protection layer, or at least one compound of the formula (I) is in the layer above the green-sensitive silver-halide emulsion layer, and the silver-halide emulsion layers contain dark-storage and/or light stabilizers.

Essential constituents of the photographic emulsion layers are binders, silver-halide grains and colour couplers.

The binder used is preferably gelatin. However, all or some of this can be replaced by other synthetic, semisynthetic or naturally occurring polymers. Examples of synthetic gelatin replacements are polyvinyl alcohol, poly-N-vinylpyrrolidone, polyacrylamides, polyacrylic acid or derivatives thereof, in particular copolymers thereof. Examples of naturally occuring gelatin replacements are other proteins, such as albumin or casein, cellulose, sugar, starch or alginates. Semisynthetic gelatin replacements are generally modified natural products. Cellulose derivatives, such as hydroxyalkylcellulose, and gelatin derivatives obtained by reaction with alkylating or acylating agents or by grafting-on polymerizable monomers, are examples thereof.

The binders should contain a sufficient mount of functional groups so that sufficiently resistant layers can be produced by reaction with suitable curing agents. Such functional groups are, in particular, amino groups, but also carboxyl groups, hydroxyl groups and active methylene groups.

The gelatin preferably used can be obtained by acidic or alkaline digestion. Oxidized gelatin can also be used. The preparation of such gelatins is described, for example, in The Science and Technology of Gelatin, edited by A. G. Ward and A. Courts, Academic Press 1977, pages 295 ff. The particular gelatin employed should contain the lowest possible content of photographically active impurities (inert gelatin). Gelatins having high viscosity and low swelling are particularly advantageous.

The halide in the silver-halide present in the photographic material as photosensitive constituent can be chloride, bromide or iodide, or a mixture thereof. The halide content of at least one layer can be, for example, from 0 to 15 mol % of iodide, from 0 to 100 mol % of chloride and from 0 to 100 mol % of bromide. The silver bromide iodide emulsions are usually used in the case of colour negative and colour reversal films, and silver chloride bromide emulsions having a high chloride content, for example at least 90 mol % of silver chloride, up to pure silver chloride emulsions are usually used in the case of colour negative and colour reversal paper. The crystals can be predominantly compact, having, for example, regular cubic or octahedral or intermediate forms, but can preferably be platelet-shaped crystals whose mean diameter:thickness ratio is preferably at least 5:1, where the diameter of a grain is defined as the diameter of a circle having an area corresponding to the projected area of the grain. However, the layers can also contain plate-shaped silver-halide crystals in which the diameter:thickness ratio is significantly greater than 5:1, for example from 12:1 to 30:1.

The silver-halide grains can also have a multilayered structure, in the simplest case if inner and outer grain regions (core/shell), the halide composition and/or other modifications, for example doping, differing in the individual grain regions. The mean grain size of the emulsions is preferably from 0.2 µm to 2.0 µm, and the grain size distribution can be either homodisperse or heterodisperse. Homodisperse grain-size distribution means that 95% of the grains have a grain size differing in the mean grain size by not more than ±30%. In addition to the silver halide, the emulsions can also contain organic silver salts, for example silver benzotriazolate or silver behenate.

It is also possible for two or more types of silver-halide emulsion, prepared separately, to be used as a mixture.

The photographic emulsions can be prepared by various methods (for example P. Glafkides, Chimie et Physique, Paul Montel, Paris (1967), G. F. Duffin, Photographic Emulsion Chemistry, The Focal Press, London (1966), V. L. Zelikman et al., Making and Coating Photographic Emulsions, The Focal Press, London (1966), from soluble silver salts and soluble halides.

Precipitation of the silver halide is preferably carried out in the presence of the binder, for example the gelatin, and can be carried out in the acidic, neutral or alkaline pH region, where silver halide complexing agents are preferably used in addition. The latter include, for example, ammonia, thioethers, imidazole, ammonium thiocyanate and excess halide. The water-soluble silver salts and the halides are combined either successively by the single-jet process or simultaneously by the double-jet process or by any combination of the two. Metering with an increasing teed rate is preferred, in which case the "critical" feed ram, at which new nuclei just fail to form, should not be exceeded. The $p_{Ag}$ region can varied within broad limits during the precipitation; the $p_{Ag}$-controlled process is preferably used, in which a certain $p_{Ag}$ value is kept constant or a defined $p_{Ag}$ profile is passed through during the precipitation. In addition to the preferred precipitation in the presence of an excess of halide, however, so-called inverse precipitation in the presence of an excess of silver halide is also possible. Besides by precipitation, the silver-halide crystals can also grow by physical ripening (Ostwald ripening) in the presence of excess halide and/or silver halide complexing agents. The growth of the emulsion nuclei can even take place predominantly by Ostwald ripening, in which case a fine-grained, so-called Lippmann emulsion is preferably mixed with a less-soluble emulsion and redissolved in the latter.

During the precipitation and/or the physical ripening of the silver halide grains, salts or complexes of metals, such as Cd, Zn, Pb, Tl, Bi, Ir, Rh or Fe, can also be present.

Furthermore, the precipitation can also be carried out in the presence of sensitizing dyes. Complexing agents and/or dyes can be deactivated at any desired point in time, for example by changing the pH or by oxidalive treatment.

When the crystal formation is complete or at any earlier point, the soluble salts are removed from the emulsion, for example by concentration and washing, by flocculation and washing, by ultra filtration or by ion exchangers.

The silver halide emulsion is generally subjected to chemical sensitization under defined conditions—pH, $p_{Ag}$, temperature, and concentration of gelatin, silver halide and sensitizer—until the sensitivity and fogging optimum has been reached. The procedure is described, for example, in H. Frieser, "Die Grundlagen der Photographischen Prozesse mir Silberhalogeniden" [The Principles of Photographic Processes using Silver Halides], pages 675–734, Akademische Verlagsgesellschaft (1968).

The chemical sensitization can be carried out with addition of compounds of sulfur, selenium, tellurium and/or compounds of metals from sub-group VIII of the Periodic Table (for example gold, palladium and iridium), and furthermore thiocyanate compounds, surface-active compounds, such as thioethers, heterocyclic nitrogen compounds (for example imidazoles and azaindenes) or spectral sensitizers (described, for example, in F. Hamer "The Cyanine Dyes and Related Compounds", 1964, and Ullmanns Encyclopädie der technischen Chemie [Ullmann's Encyclopaedia of Industrial Chemistry], 4th Edition, Vol. 18, pp. 431 ff, and Research Disclosure 17643 (December 1978), Chapter III). Instead of or in addition to the above, reduction sensitization but with addition of reducing agents (tin(II) salts, amines, hydrazine derivatives, aminoboranes, silanes or formamidinesulfinic acid), can be carried out by hydrogen, a low $p_{Ag}$ (for example less than 5) and/or high pH (above 8).

The photographic emulsions can contain compounds for inhibiting fogging or for stabilizing the photographic function during production, storage or photographic processing. Particularly suitable are azaindenes, preferably tetra- and pentaazaindenes, in particular those substituted by hydroxyl or amino groups. Such compounds have been described, for example, by Birr, Z. Wiss. Phot. 47 (1952), pp. 2–58. It is also possible to use, as antifogging agent, salts of metals such as mercury or cadmium, aromatic sulfonic or sulfinic acids, such as benzenesulfinic acid, or nitrogen-containing heterocyclic compounds, such as nitrobenzimidazole, nitroindazole, substituted or unsubstituted benzotriazoles or benzothiazolium salts. Particularly suitable are heterocyclic compounds containing mercapto groups, for example mercaptobenzothiazoles, mercaptobenzimidazoles, mercaptotetrazoles, mercaptothiadiazoles and mercaptopyrimidines, where these mercaptoazoles also contain a water-solubilizing group, for example a carboxyl group or sulfo group. Other suitable compounds are disclosed in Research Disclosure 17643 (December 1978), Chapter VI.

The stabilizers can be added to the silver-halide emulsions before, during or after their ripening. It is of course also possible to add the compounds to other photographic layers assigned to a silver-halide layer.

It is also possible to use mixtures of two or more of said compounds.

The photographic emulsion layers or other hydrophilic colloid layers of the photosensitive material produced in accordance with the invention can contain surfactants for various purposes, such as coating auxiliaries, for preventing electrical charging, for improving the sliding properties, for emulsification of the dispersion, for preventing adhesion and for improving the photographic characteristics (for example development acceleration, contrast increase, sensitization, etc.). Besides natural surface-active compounds, for example saponin, use is principally made of synthetic surface-active compounds (surfactants); nonionic suffactants, for example alkylene oxide compounds, glycerol compounds or glycidol compounds, cationic surfactants, for example higher alkylamines, quaternary ammonium salts, pyridine compounds and other heterocyclic compounds, sulfonium compounds or phosphonium compounds, anionic surfactants containing an acid group, for example a carboxyl, sulfo, phosphoric acid, sulfate or phosphate group, ampholytic surfactants, for example amino acid and aminosulfonic acid compounds and sulfates or phosphates of an amino alcohol.

The photographic emulsions can be spectrally sensitized using methine or other dyes. Particularly suitable dyes are cyanine dyes, merocyanine dyes and complex merocyanine dyes.

A review of polymethine dyes which are suitable as spectral sensitizers, suitable combinations thereof and supersensitizing combinations is given in Research Disclosure 17643 (December 1978), Chaper IV.

In particular, the following dyes—arranged by spectral region—are suitable:

1. As red sensitizers:
9-ethylcarbocyanines containing benzothiazole, benzoselenazole or naphthothiazole as basic terminal groups, which can be substituted in the 5- and/or 6-position by halogen, methyl, methoxy, carbalkoxy or aryl, and 9-ethylnaphthoxathia- and -selenocarbocyanines and 9-ethylnaphthothiazoxa- and -benzimidazocarbocyanines, provided that the dyes carry at least one sulfoalkyl group of the heterocyclic nitrogen.

2. As green sensitizers
9-ethylcarbocyanines containing benzoxazole, naphthoxazole or a benzoxazole and a benzothiazole as basic terminal groups, and benzimidazocarbocyanines, which can likewise be further substituted and likewise contain at least one sulfoalkyl group on the heterocyclic nitrogen.

3. As blue sensitizers
symmetrical or asymmetrical benzimidazo- -oxa-, -thia- or -selenacyanines containing at least one sulfoalkyl group on the heterocyclic nitrogen and, if desired, further substituents on the aromatic ring, and apomerocyanines containing a rhodanine group.

Examples which may be mentioned, in particular for negative and reversal film, are the red sensitizers (RS), green sensitizers (CS) and blue sensitizers (BS) listed below, each of which may be employed individually or in combination with one another, for example RS-1 and RS-2, and GS-1 and GS-2.

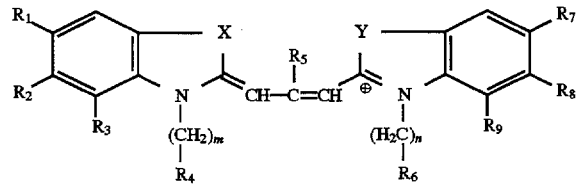

RS-1: $R_1$, $R_3$, $R_7$ and $R_9$=H; $R_2$, $R_8$=Cl; $R_4$=—$SO_3\ominus\oplus NH(C_2H_5)_3$; $R_5$=—$C_2H_5$; $R_6$=—$SO_3\ominus$; m and n=3; x and 4=5;

RS-2: $R_1$, $R_3$ and $R_9$=H; $R_2$=phenyl; $R_4$=

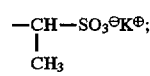

$R_5$=$C_2H_5$; $R_6$=—$SO_3\ominus$; $R_7$, $R_8$=—$OCH_3$; m=2; n=3; X=O; Y=S;

RS-3: $R_1$ and $R_9$=H; $R_2$ and $R_3$ together —CH=CH—CH=CH—; $R_4$=—$SO_3\ominus Na\oplus$; $R_5$=—$C_2H_5$; $R_6$=—$SO_3\ominus$; $R_7$, $R_8$=Cl; m and n=3; X=S; Y=N—$C_2H_5$;

RS-4: $R_1$=—$OCH_3$; $R_2$ and $R_8$=—$CH_3$; $R_3$, $R_4$, $R_7$ and $R_9$=H; $R_5$=—$C_2H_5$; $R_6$=—$SO_3\ominus$; m=2; n=4; X=S; Y=Se;

RS-5: $R_1$ and $R_7$=H; $R_2$ and $R_3$, and $R_8$ and $R_9$ together —CH=CH—CH=CH—; $R_4$=—$SO_3\ominus\oplus NH(C_2H_5)_3$; $R_5$=$C_2H_5$; $R_6$=$SO_3\ominus$; m=2; n=3; X and Y=S;

GS-1: $R_1$, $R_3$, $R_7$ and $R_9$=H; $R_2$=phenyl; $R_4$=

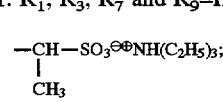

$R_5$=—$C_2H_5$; $R_6$=—$SO_3\ominus$; $R_8$=Cl; m=2; m=3; X and Y=O;

GS-2: $R_1$, $R_2$, $R_7$ and $R_8$=Cl; $R_3$, $R_5$, $R_6$ and $R_9$=H; $R_4$=

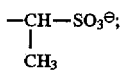

m and n=2; X and Y=N—$C_2H_5$;

GS-3: $R_1$ and $R_7$=H; $R_2$ and $R_3$, and $R_8$ and $R_9$ together —CH=CH—CH=CH—; $R_4$=$SO_3\ominus Na\oplus$; $R_5$=$C_2H_5$; $R_6$=$SO_3\ominus$; m and n=3; X and Y=O;

GS-4: $R_1$, $R_3$, $R_4$, $R_7$, $R_8$ and $R_9$=H; $R_2$=—$OCH_3$; $R_5$=—$C_2H_5$; $R_6$=$SO_3\ominus$; m=2; n=4; X=O; Y=S;

BS-1:

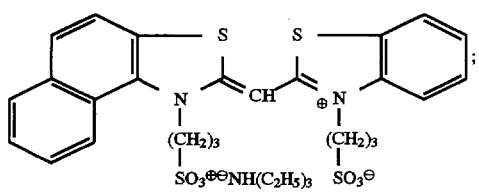

BS-2:

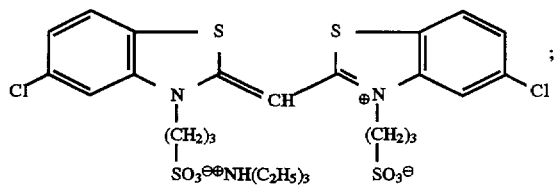

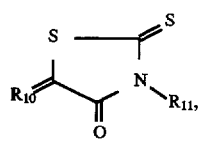

wherein in

BS-3: $R_{10}$=

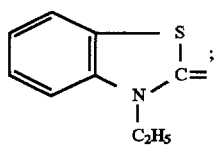

$R_{11}$=—$CH_2$—COOH;

BS-4: $R_{10}$=

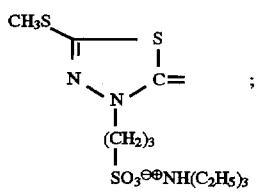

$R_{11}$=—$C_2H_5$;

BS-5: $R_{10}$=

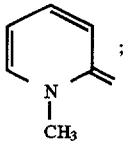

$R_{11}$=—$C_2H_5$.

Sensitizers can be omitted if the inherent sensitivity of the silver halide is sufficient for a certain spectral region, for example the blue sensitivity of silver bromides.

Non-diffusing monomeric or polymeric colour couplers are assigned to the emulsion layers of various sensitization; these couplers can be in the same layer or in an adjacent layer. Cyan couplers are usually assigned to the red-sensitive layers, magenta couplers to the green-sensitive layers and yellow couplers to the blue-sensitive layers.

Yellow couplers which can be used in the material according to the invention are preferably compounds of the formula A

in which $R_1$ is alkyl or aryl, $R_2$ is aryl and Q is hydrogen or a group which can be eliminated by reaction with the oxidised developer.

A group of yellow couplers comprises the compounds of the formula A in which $R_1$ is t-butyl and $R_2$ is a group of the formula

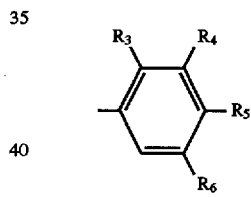

in which $R_3$ is hydrogen, halogen, alkyl or alkoxy, and $R_4$, $R_5$ and $R_6$ are hydrogen, halogen, alkyl, alkenyl, alkoxy, aryl, carboxyl, alkoxycarbonyl, carbamoyl, sulfonyl, sulfamoyl, alkoxysulfonylamino, acylamino, ureido or amino.

Preferably, $R_3$ is chlorine or methoxy, $R_4$ and $R_5$ are hydrogen and $R_6$ is an acylamion group. This group also includes the compounds of the formula

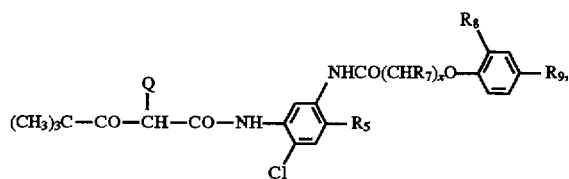

in which x is 0–4, $R_7$ is hydrogen or alkyl, $R_8$ and $R_9$ are alkyl.

Another group of yellow couplers conforms to the formula B

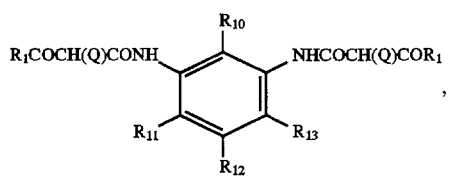

(B)

in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, carbamoyl, sulfonyl, sulfamoyl, sulfonamido, acylamino, ureido or amino, and $R_1$ and Q are as defined above.

This group includes compounds of the formula B in which $R_1$ is t-butyl, $R_{10}$ is chlorine, $R_{11}$ and $R_{13}$ are hydrogen, and $R_{12}$ is alkoxycarbonyl.

In the compounds of the formulae A and B, leaving group Q may be hydrogen (tetraequivalent couplers) or a heterocyclic group (diequivalent couplers)

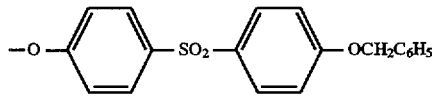

in which $R_{14}$ is a divalent organic group which supplements the ring to make up a 4–7-membered ring, or Q is an —$OR_{15}$ group in which $R_{15}$ is alkyl, aryl, acyl or a heterocyclic radical.

Typical examples of customary yellow couplers are the compounds of the formulae below:

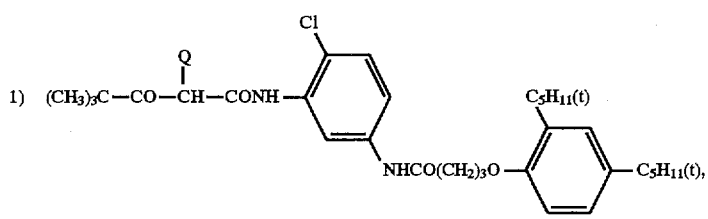

wherein a) Q=

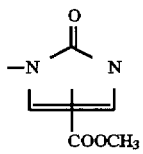

b) Q= c) Q= d) Q= e) Q=

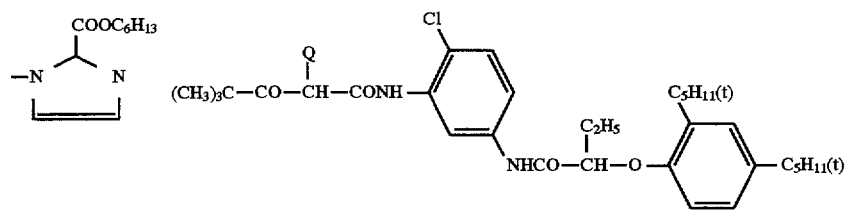

f) Q=
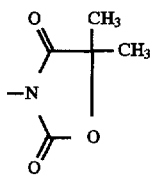
g) Q=
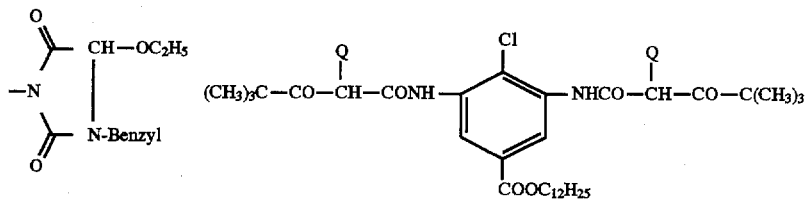
h) Q=
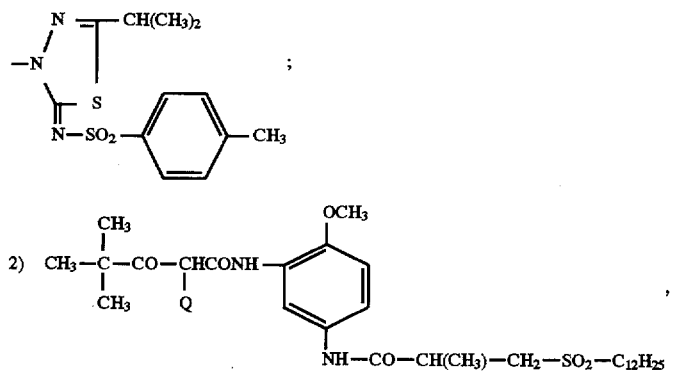
wherein
i) Q=
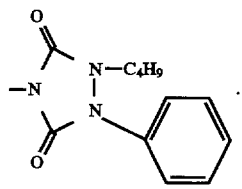
Further examples of yellow couplers are given in U.S. Pat. Nos. 2,407,210, 2,778,658, 2,875,057, 2,908,513, 2,908,573, 3,227,155, 3,227,550, 3,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752, 4,022,620, 5,118,599, 5,215,878, 5,260,182, 5,294,527, 5,298,383, 5,300,412, 5,306,609, 5,314,797 and 5,336,591 in DE-A1 547 868, 2 057 941, 2 162 899, 2 163 813, 2 213 461, 2 219 917, 2 261 361, 2 261 362, 2 263 875, 2 329 587, 2 414 006 and 2 422 812, in GB-A 1 425 020 and 1 077 874 and in JP-A-88/123 047, U.S. Pat. Nos. 4,133,052, 5,080,469 and 5,313,323, and in EP-A 447 969, 447 969, 508 398, 510 535, 542 463 and 568 198.
The yellow couplers are usually used in an amount of 0.05–2 mol and preferably 0.1–1 mol per mol of silver halide.

Typical and preferred yellow couplers conform to the formulae:
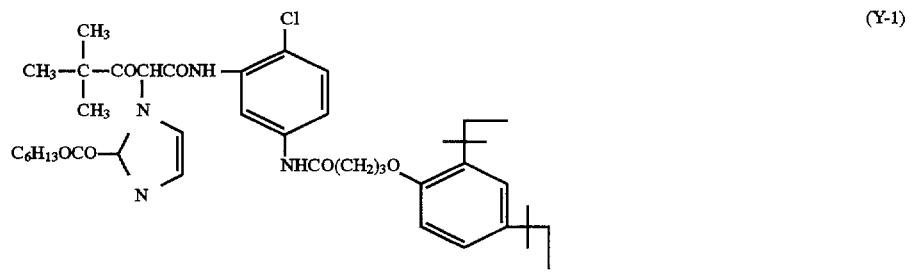
(Y-1)
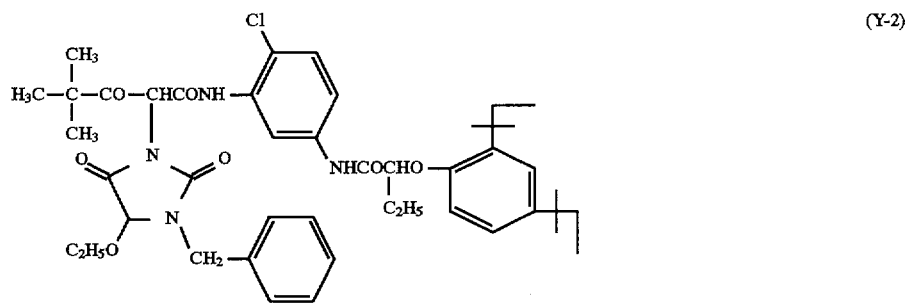
(Y-2)
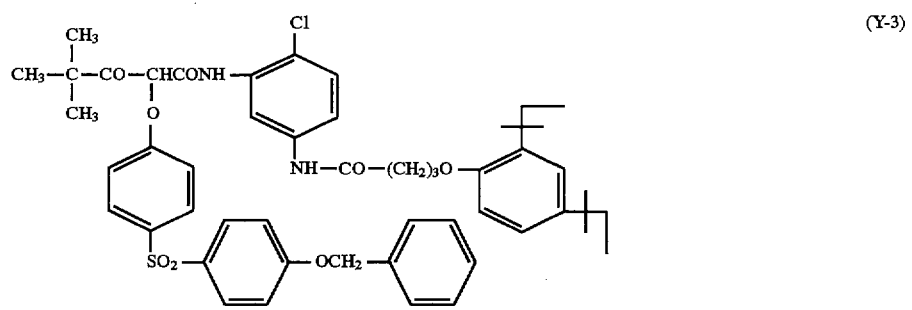
(Y-3)
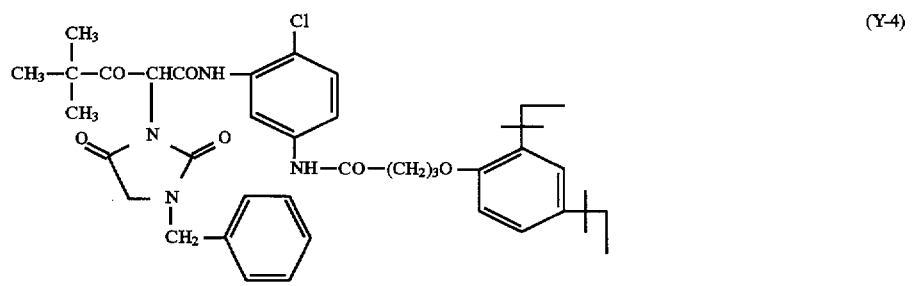
(Y-4)
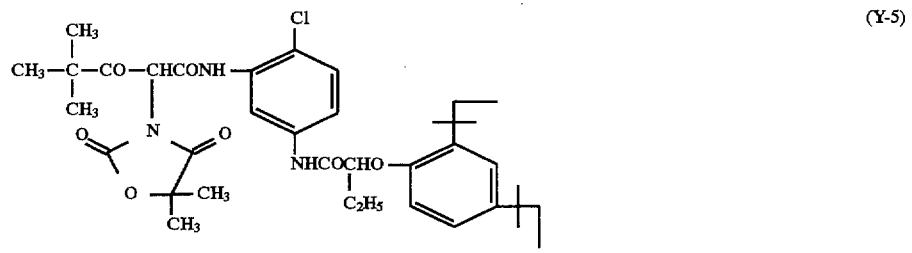
(Y-5)
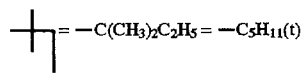

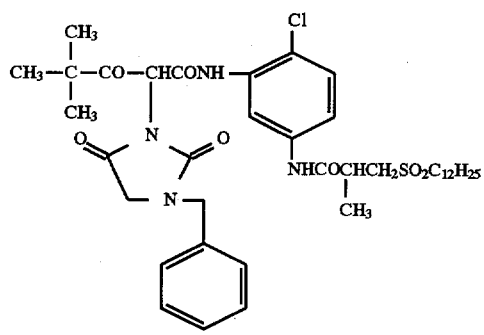 (Y-6)
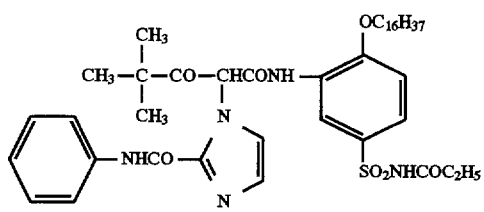 (Y-7)
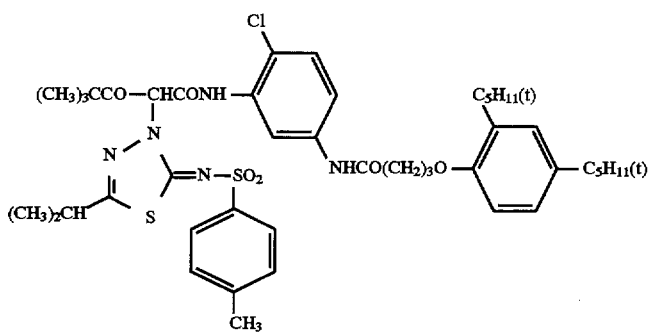 (Y-8)
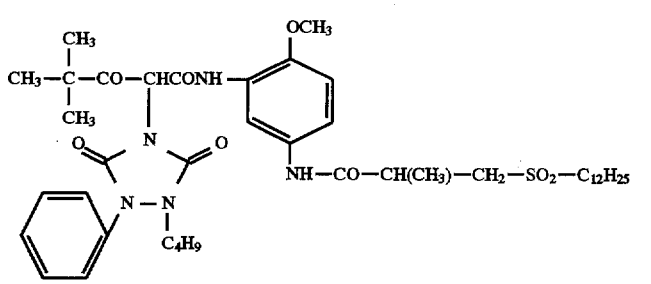 (Y-9)
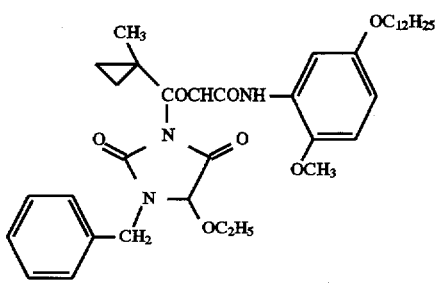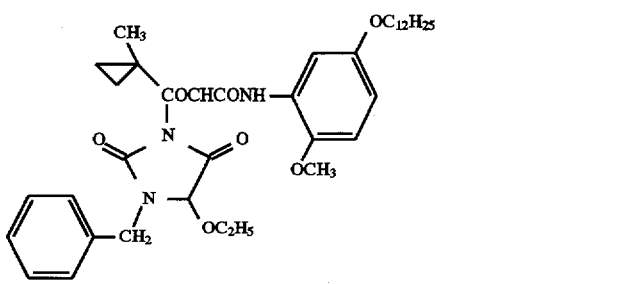 (Y-10)

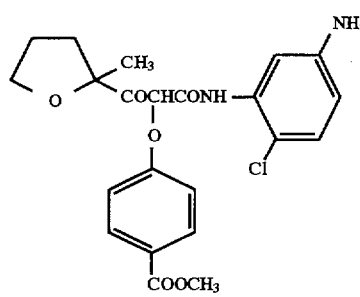
(Y-11)
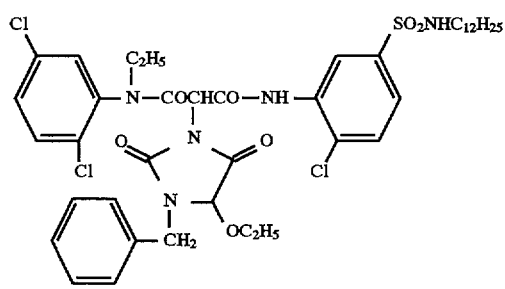
(Y-12)
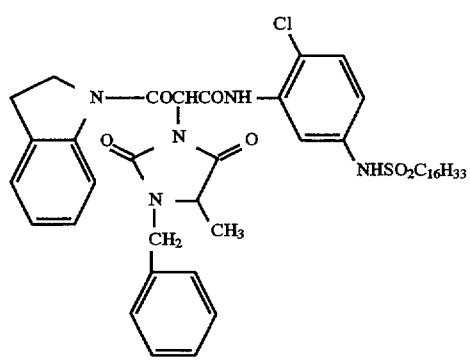
(Y-13)
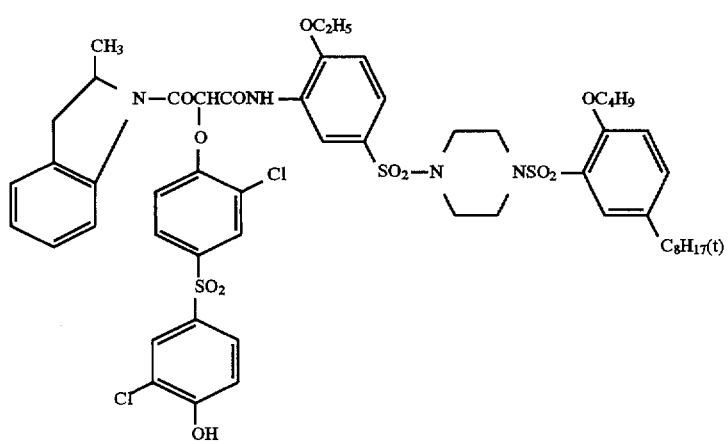
(Y-14)

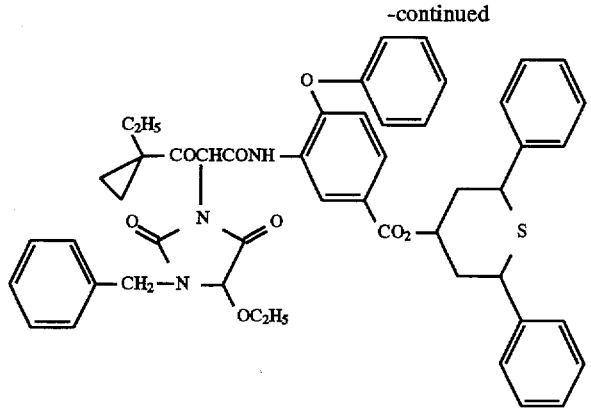
(Y-15)
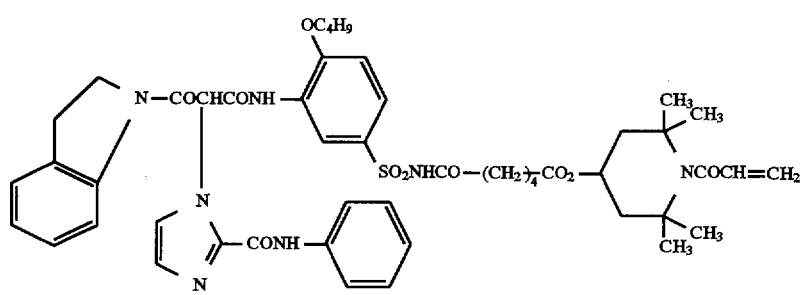
(Y-16)
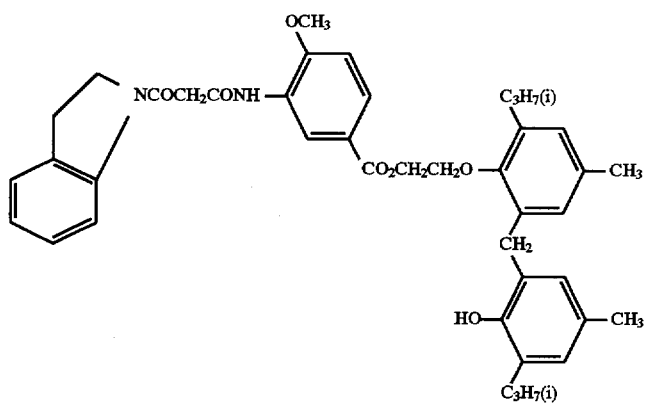
(Y-17)
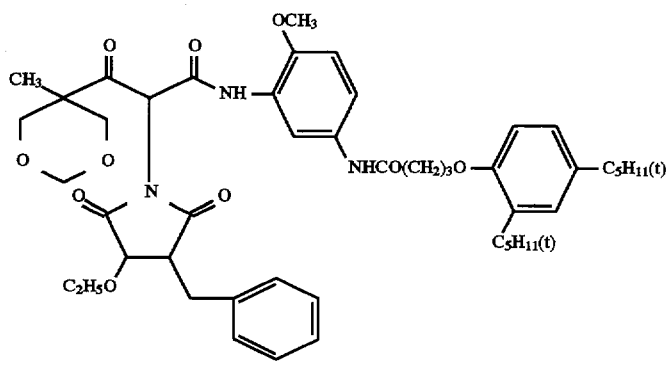
(Y-18)

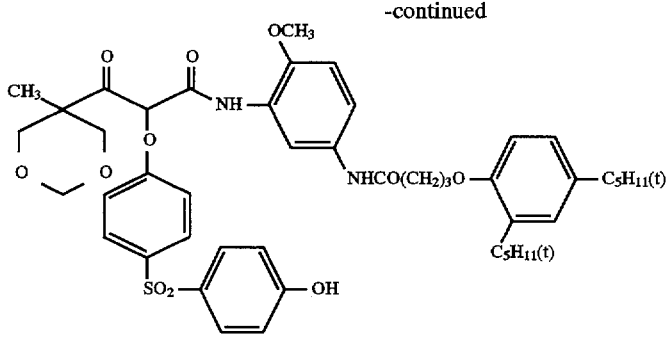

(Y-19)

Examples of magenta couplers are simple 1-aryl-5-pyrazolones or pyrazole derivatives which have been condensed with 5-membered hereto rings, e.g. imidazopyrazoles, pyrazolopyrazoles, pyrazolotriazoles and pyrazolotetrazoles.

One group of magenta couplers comprises 5-pyrazolones of the formula C

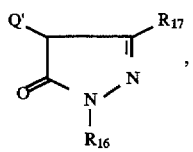

(C)

as described in British Patent 2 003 473. In this formula, $R_{16}$ is hydrogen, alkyl, alkenyl or a heterocyclic group and $R_{17}$ is hydrogen, alkyl, aryl, a heterocyclic group, an ester group, an alkoxy group, an alkylthio group, a carboxyl group, an arylamino group, an acylamino group, a (thio)urea group, a (thio)carbamoyl group, a guanidino group or sulfonamido group.

$R_{17}$ is preferably an

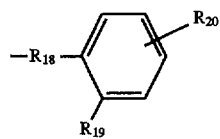

group, in which $R_{18}$ is imino, acylamino or ureido, $R_{19}$ is hydrogen, halogen, alkyl or alkoxy and $R_{20}$ is hydrogen, alkyl, acylamino, carbamoyl, sulfamoyl, sulfonamido, alkoxycarbonyl, acyloxy or a urethane group.

If Q' is hydrogen, the magenta coupler is tetraequivalent with respect to the silver halide.

Typical examples of magenta couplers of this type are compounds of the formula

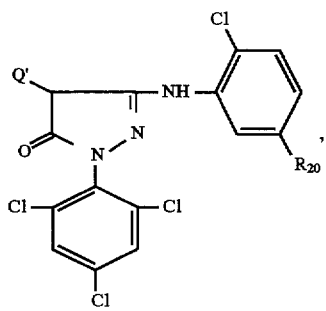

in which $R_{20}$ is as defined above, and Q', as described above, is a leaving group. These compounds are preferably present in the material according to the invention.

Further examples of tetraequivalent magenta couplers of this type are given in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500 and JP-A-89/309 058.

If Q' in the formula C is not hydrogen, but instead a group which is eliminated during the reaction with the oxidised developer, the magenta coupler is diequivalent. In this case, Q can be, for example, halogen or a group bonded to the pyrazole ring via O, S or N. Diequivalent couplers of this type give greater colour density and are more reactive towards the oxidised developer than are the corresponding tetraequivalent magenta couplers.

Examples of diequivalent magenta couplers are described in U.S. Pat. Nos. 3,006,579, 3,419,391, 3,311,476, 3,432, 521, 3,214,437, 4,032,346, 3,701,783, 4,351,897, 3,227,554, 3,262,292. in EP-A-133 503, 529 784, 530 039, DE-A-2 944 601, JP-A-78/34 044, 74/53 435, 74/53 436, 75/53 372 and 75/122 935, 3 323 851, 4 018 547 and 5 150 429 and WO 93/02 392.

Typical and preferred magenta couplers conform to the formulae:

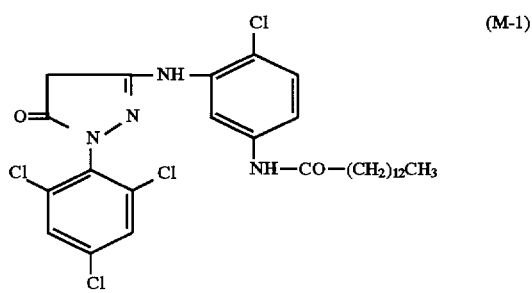

(M-1)

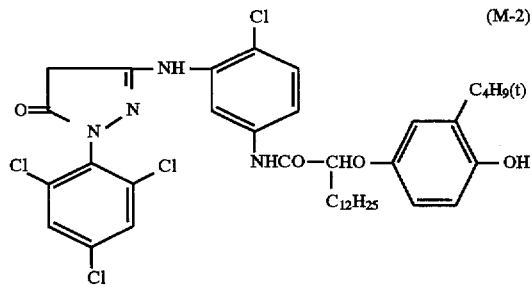

(M-2)

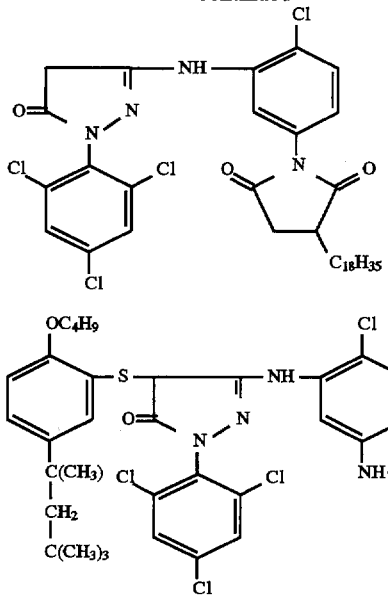

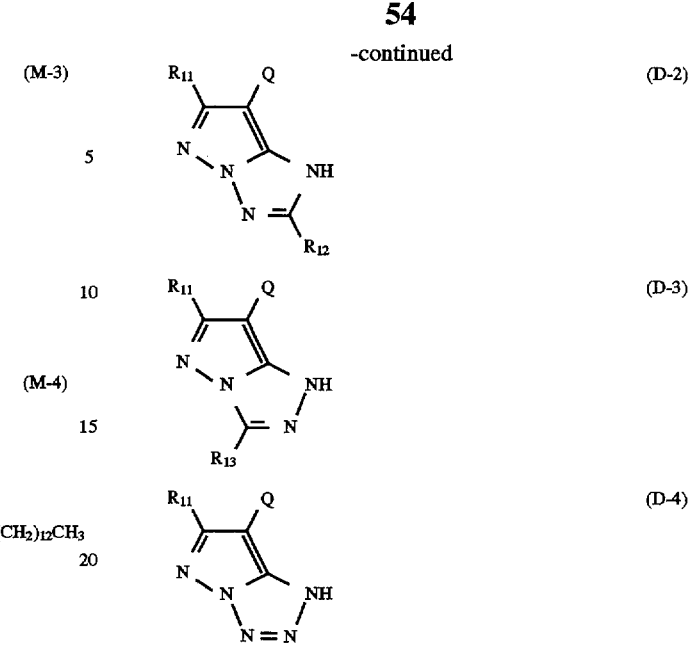

It is possible for 2 pyrazolone rings to be linked via a divalent Q', giving so-called bis-couplers. These are described, for example, in U.S. Pat. Nos. 2,632,702, 2,618, 864, GB-A-968 461, GB-A-786 859, JP-A-76/37 646, 59/4 086, 69/16 110, 69/26 589, 74/37 854 and 74/29 638. Y is preferably an O-alkoxyarylthio group.

As mentioned above, the magenta couplers used can also be pyrazoles condensed with 5-membered heterocyclic rings, known as pyrazoloazoles. Their advantages over simple pyrazoles is that they have colours of greater formalin resistance and have purer absorption spectra.

Magenta couplers of the pyrazoloazole type, which are likewise preferred, may be represented by the formula D

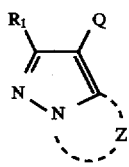                                                     D in which $R_1$ is hydrogen or a substituent, Z represents the non-metallic atoms necessary to complete a 5-membered ring containing 2 or 3 nitrogen atoms, it being possible for this ring to be substituted, and Q is hydrogen (tetraequivalent couplers) or a leaving group (diequivalent couplers).

Of these compounds, preference is given to magenta couplers of the formulae

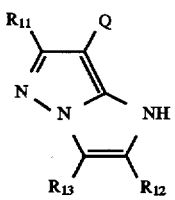                                                    (D-1)

$R_{11}$, $R_{12}$ and $R_{13}$, independently of one another, are, for example, hydrogen; halogen (for example chlorine or bromine), —$CR_3$ in which the radicals $R_3$ are, independently of one another, hydrogen or alkyl, aralkyl, alkenyl, alkynyl, cycloalkyl or cycloalkenyl, particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy) dodecanamido)phenyl)propyl, 2-ethoxytridecyl, trifluoromethyl, cyclopentyl, 3-(2,4-di-t-amylphenoxy) propyl; aryl (for example phenyl, 4-t-butylphenyl, 2,4-di-t-amylphenyl or 4-tetradecaneamidophenyl); heterocyclyl (for example 2-furyl, 2-thienyl, 2-pyrimidinyl or 2-benzothiazolyl); cyano; hydroxyl, nitro; carboxyl; amino; alkoxy (for example methoxy, ethoxy, 2-methoxyethoxy; 2-dodecylethoxy, 2-methanesulfonylethoxy); aryloxy (for example phenoxy, 2-methylphenoxy, 4-t-butylphenoxy, 3-nitrophenoxy, 3-t-butyloxycarbamoylphenoxy or 3-methoxycarbamoyl); acylamino (for example acetoamido, benzamido, tetradecaneamido, 2-(2,4-di-t-amylphenoxy) butaneamido, 4-(3-t-butyl-4-hydroxyphenoxy)butaneamido or 2-(4-(4-hydroxyphenylsulfonyl)phenoxy)decaneamido); methylbutylamino; anilino (for example phenylamino, 2-chloroanilino, 2-chloro-5-tetradecaneaminoanilino, 2-chloro-5-dodecyloxycarbonylanilino, N-acetylanilino or 2-chloro-5-(alpha-(3-t-butyl-4-hydroxyphenoxy) dodecaneamidoanilino)); ureido (for example phenylureido, methylureido or N,N-dibutylureido); sulfamoylamino (for example N,N-dipropylsulfamoylamino or N-methyl-N-decylsulfamoylamino); alkylthio (for example methylthio, octylthio, tetradecylthio, 2-phenoxyethylthio, 3-phenoxypropylthio or 3-(4-t-butylphenoxy)propylthio); arylthio (for example phenylthio, 2-butoxy-5-t-octylphenylthio, 3-pentadecylphenylthio, 2-carboxyphenylthio or 4-tetradecaneamidophenylthio); alkoxycarbonylamino (for example methoxycarbonylamino or tetradecyloxycarbonylamino); sulfonamido (for example methanesulfonamido, hexadecanesulfonamido, benzenesulfonamido, p-toluenesulfonamido, octadecane-sulfonamido or 2-methoxy-5-t-butylbenzenesulfonamido); carbamoyl (for example N-ethylcarbamoyl, N,N-dibutylcarbamoyl, N-(2-dodecyloxyethyl)carbamoyl, N-methyl-N-dodecylcarbamoyl or N-(3-(2,4-di-t- amylphenoxy)propyl)carbamoyl); sulfamoyl (for example N-ethylsulfamoyl, N,N-dipropylsulfamoyl, N-2-(dodecyloxyethyl)sulfamoyl, N-ethyl-N-dodecylsulfamoyl or N,N-diethylsulfamoyl); sulfonyl (for example methanesulfonyl, octanesulfonyl, benzenesulfonyl or toluenesulfonyl); alkoxycarbonyl (for example methoxycarbonyl, butoxycarbonyl, dodecyloxycarbonyl or octadecyloxycarbonyl); heterocyclyloxy (for example 1-phenyltetrazol-5-oxy or 2-tetrahydropyranyloxy); azo (for example phenylazo, 4-methoxyphenylazo, 4-pivaloylaminophenylazo or 2-hydroxy-4-propanoylphenylazo); acyloxy (for example acetoxy); carbamoyloxy (for example N-methylcarbamoyloxy or N-phenylcarbamoyloxy); silyloxy (for example trimethylsilyloxy or dibutylmethylsilyloxy); aryloxycarbonylamino (for example phenoxycarbonylamino); imido (for example N-succinimido, N-phthalimido or 3-octadecenylsuccinimido); heterocyclylthio (for example 2-benzothiazolylthio, 2,4-diphenyloxy-1,3,5-triazole-6-thio or 2-pyridylthio); sulfinyl (for example dodecanesulfinyl, 3-pentadecylphenylsulfinyl or 3-phenoxypropylsulfinyl); phosphonyl (for example phenoxyphosphonyl, octyloxyphosphonyl or phenylphosphonyl); aryloxycarbonyl (for example phenoxycarbonyl); acyl (for example acetyl, 3-phenylpropanoyl, benzoyl or 4-dodecyloxybenzoyl); or azolyl (for example imidazolyl, pyrazolyl or 3-chloropyrazol-1-yl).

These substituents may be further substituted, for example by halogen or by an organic radical bonded via a C, O, N or S atom.

Preferred groups $R_{11}$ are alkyl, aryl, alkoxy, aryloxy, alkylthio, ureido, urethane and acylamino groups.

$R_{12}$ may be as defined for $R_{11}$ and is preferably hydrogen, alkyl, aryl, a heterocyclic ring, alkoxycarbonyl, carbamoyl, sulfamoyl, sulfinyl, acyl or cyano.

$R_{13}$ may be as defined for $R_{11}$ and is preferably hydrogen, alkyl, aryl, a heterocyclic ring, alkoxy, aryloxy, alkylthio, arylthio, alkoxycarbonyl, carbamoyl or acyl, in particular alkyl, aryl, a heterocyclic ring, alkylthio or arylthio.

Q is hydrogen or a leaving group, such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl-, aryl- or heterocyclyl-S-carbamoylamino, a 5- or 6-membered, nitrogen-containing heterocyclic radical, imido or arylazo. These groups may be further substituted as indicated for $R_{11}$.

Q is preferably halogen (for example fluorine, chlorine or bromine); alkoxy (for example ethoxy, dodecyloxy, methoxyethylcarbamoylmethoxy, carboxypropoxy, methylsulfonylethoxy or ethoxycarbonylmethoxy); aryloxy (for example 4-methylphenoxy, 4-chlorophenoxy, 4-methoxyphenoxy, 4-carboxyphenoxy, 3-ethoxycarboxyphenoxy, 3-acetylaminophenoxy or 2-carboxyphenoxy); acyloxy (for example acetoxy, tetradecanoyloxy or benzoyloxy); alkyl- or arylsulfonyloxy (for example methanesulfonyloxy or toluenesulfonyloxy); acylamino (for example dichloroacetylamino or heptafluorobutyrylamino); alkyl- or arylsulfonamido (for example methanesulfonamido, trifluoromethanesulfonamido or p-toluenesulfonamido); alkoxycarbonyloxy (for example ethoxycarbonyloxy or benzyloxycarbonyloxy); aryloxycarbonyloxy (for example phenoxycarbonyloxy); alkyl-, aryl- or heterocyclyl-S- (for example dodecylthio, 1-carboxydodecylthio, phenylthio, 2-butoxy-5-t-octylphenylthio or tetrazolylthio); carbamoylamino (for example N-methylcarbamoylamino or N-phenylcarbamoylamino); a 5- or 6-membered, nitrogen-containing ring (for example imidazolyl, pyrazolyl, triazolyl, tetrazolyl or 1,2-dihydro-2-oxo-1-pyridyl); imido (for example succinimido or hydantoinyl); or arylazo (for example phenylazo or 4-methoxyphenylazo).

Q may alternatively form corresponding bis-compounds by condensation of tetraequivalent couplers with an aldehyde or ketone. Furthermore, Q may contain photographically active groups, such as development inhibitors or development accelerators. Q is preferably halogen, alkoxy, aryloxy, alkyl- or arylthio, or a 5- or 6-membered, nitrogen-containing, heterocyclic group which is bonded to the coupling site via a nitrogen atom.

Pyrazolotetrazoles are described in JP-A-85/33 552; pyrazolopyrazoles in JP-A-85/43 695; pyrazoloimidazoles in JP-A-85/35 732, JP-A-86/18 949 and U.S. Pat. No. 4,500,630; pyrazolotriazoles in JP-A-85/186 567, JP-A-86/47 957, JP-A-85/215 687, JP-A-85/197 688, JP-A-85/172 982, EP-A-119 860, EP-A-173 256, EP-A-178 789, EP-A-178 788 and in Research Disclosure 84/24 624.

Further pyrazoloazole magenta couplers are described in: JP-A-86/28 947, JP-A-85/140 241, JP-A-85/262 160, JP-A-85/213 937, JP-A-87/278 552, JP-A-87/279 340, JP-A-88/100 457, JP-A-5 027 391, JP-A-5 053 271, JP-A-5 053 272, JP-A-232 646, JP-A-5 241 286, JP-A-5 241 287, JP-A-5 241 288, JP-A-5 241 289, JP-A-5 241 290, JP-A-5 249 633, JP-A-5 3033181, JP-A-5 323 530, EP-A-177 765, EP-A-176 804, EP-A-170 164, EP-A-164 130, EP-A-178 794, EP-A-0 487 081, EP-A-0 489 333, EP-A-0 558 145, EP-A-0 568 894, DE-A-3 516 996, DE-A-3 508 766, DE-A-4 240 000, WO 92/10 788, WO 92/12 464, U.S. Pat. Nos. 5,100,772, 5,254,451, 5,300,407, 5,336,593 and Research Disclosure 81/20 919, 84/24 531 and 85/25 758.

Examples of suitable couplers of this type are:

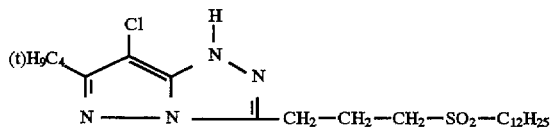

(M-5)

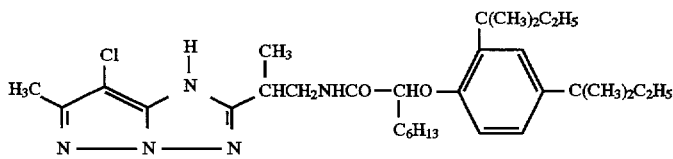

(M-6)

-continued
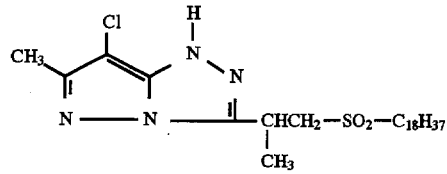
(M-7)
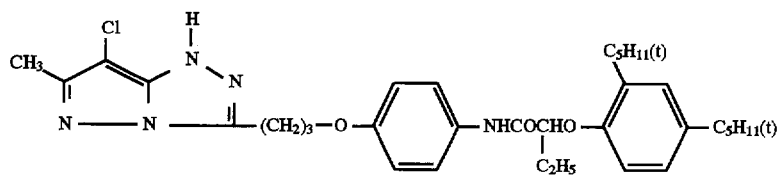
(M-8)
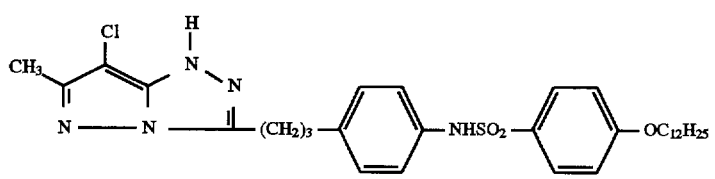
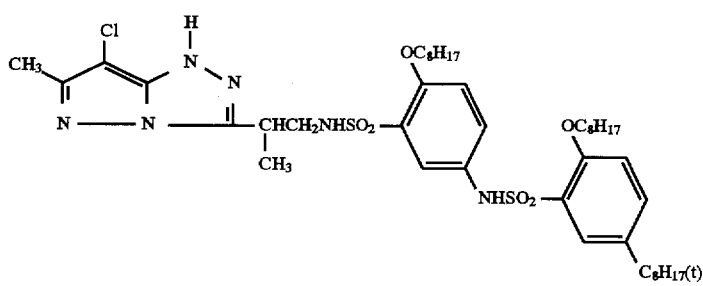
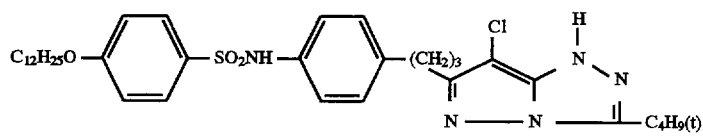
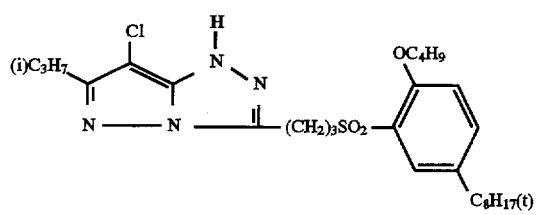
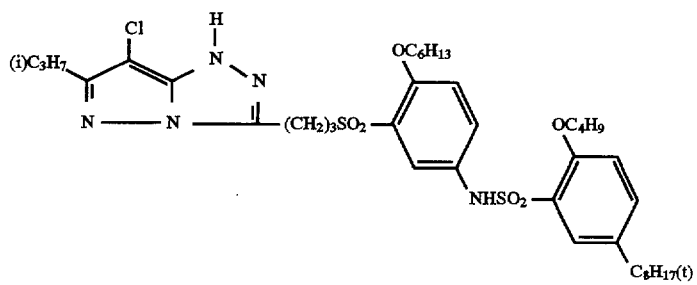
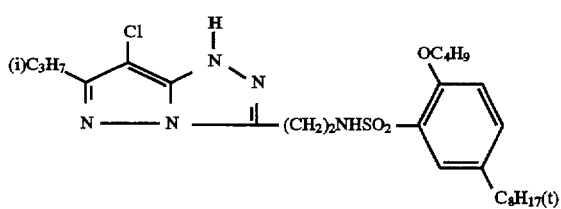

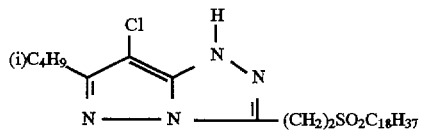
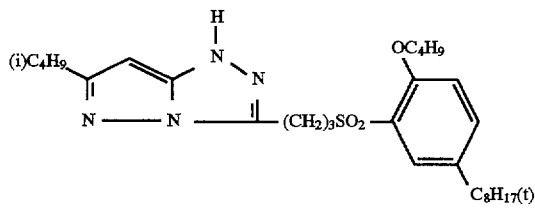
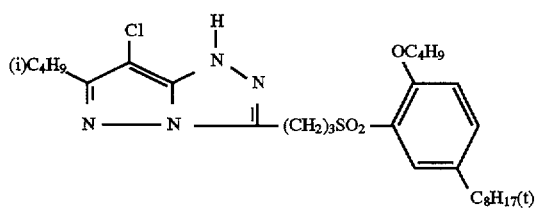
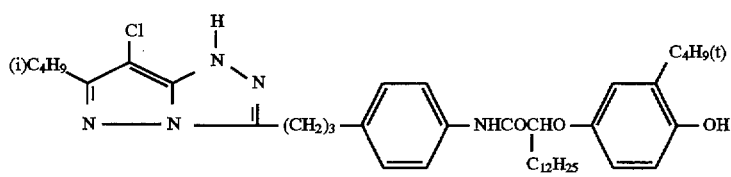
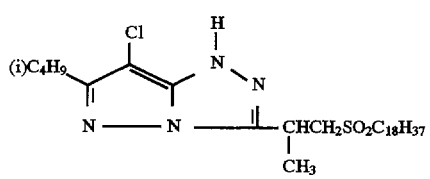
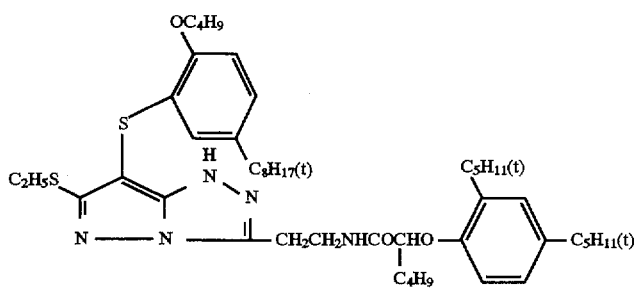
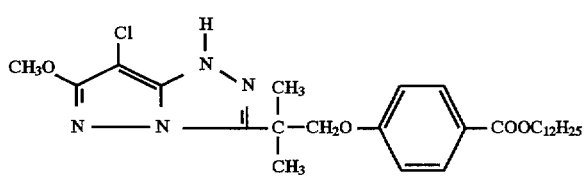
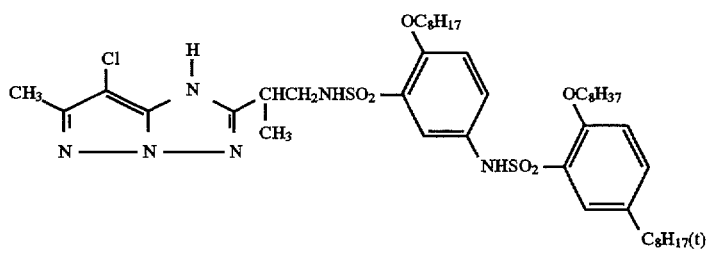

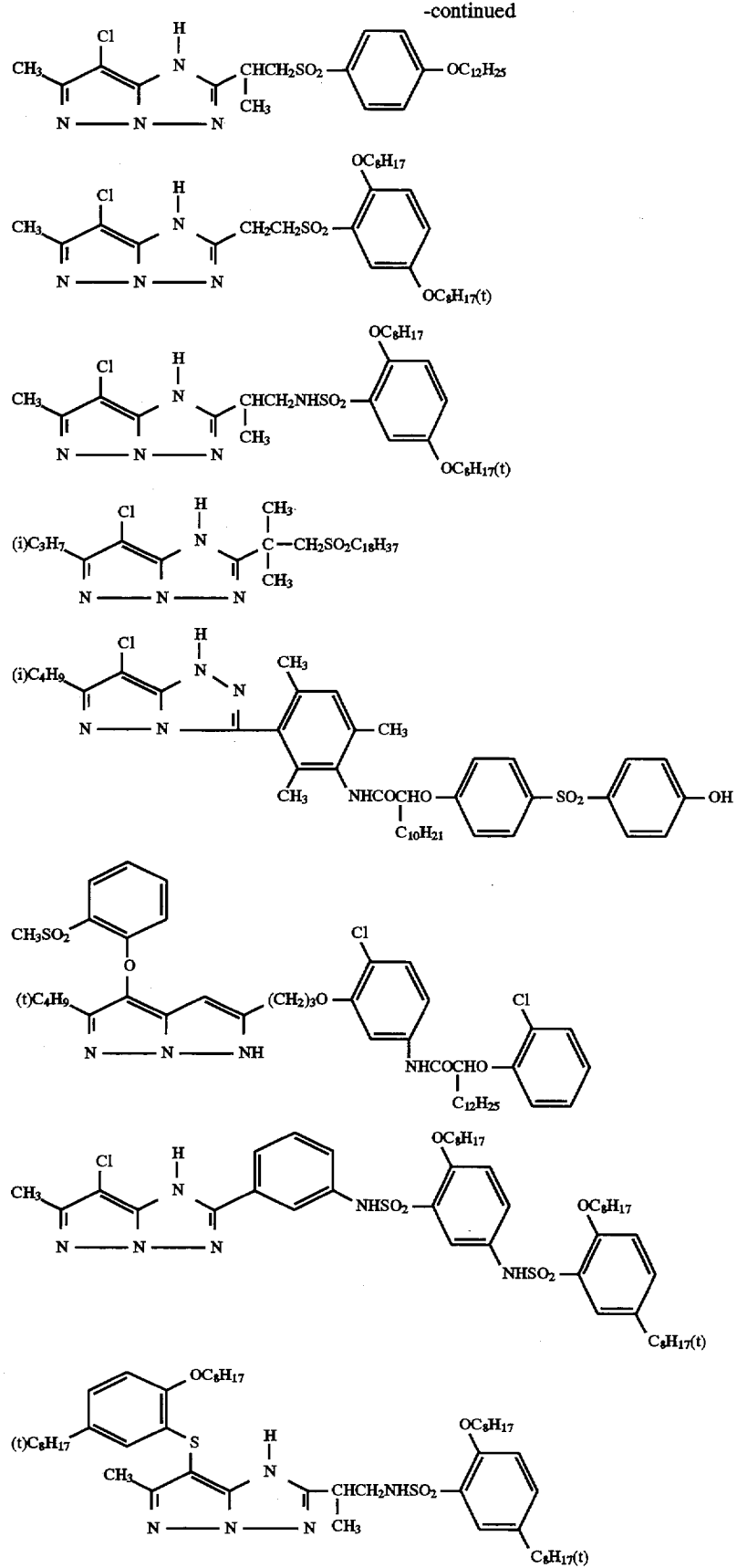

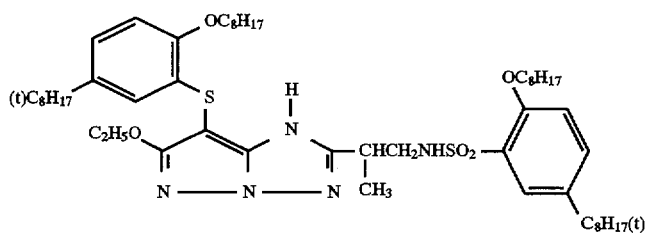
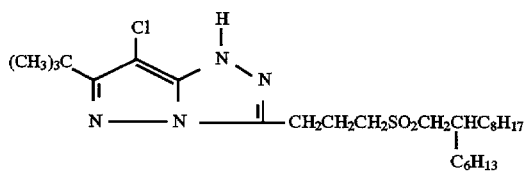
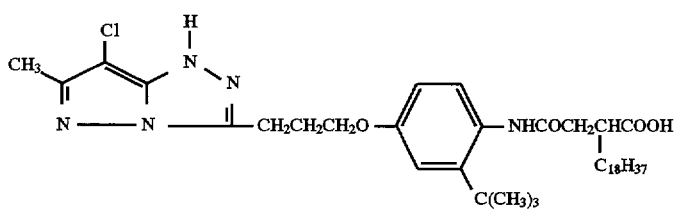
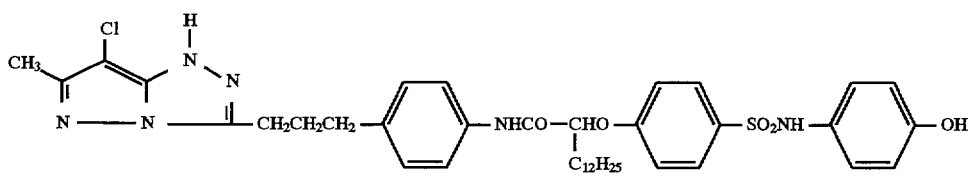
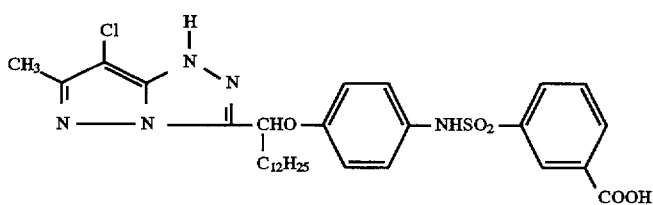
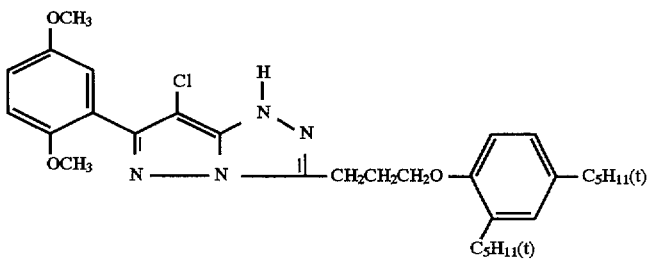
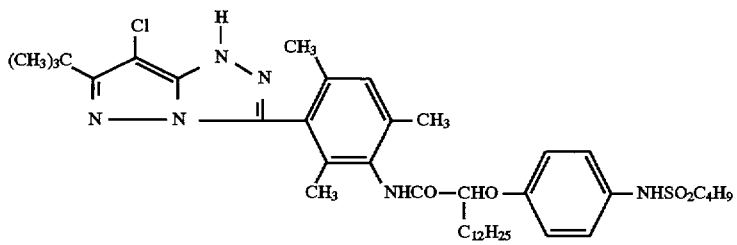

-continued
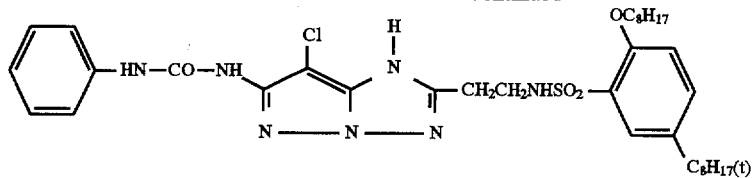
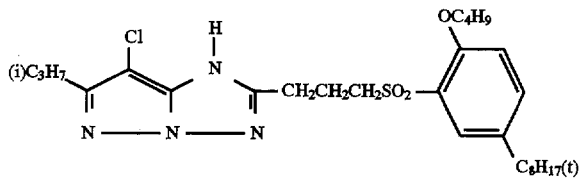
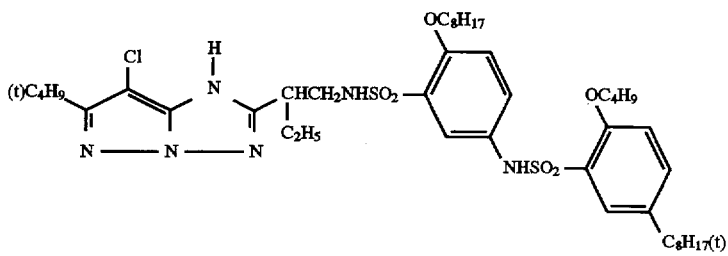
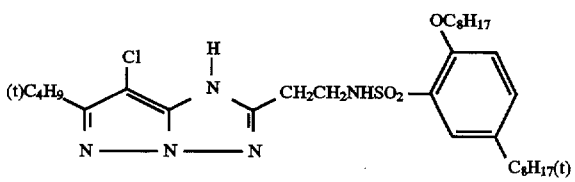
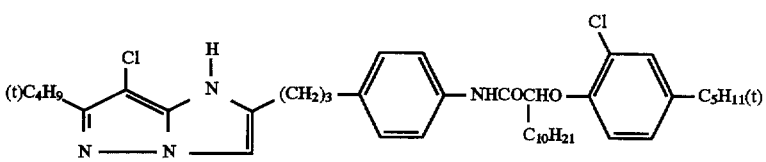
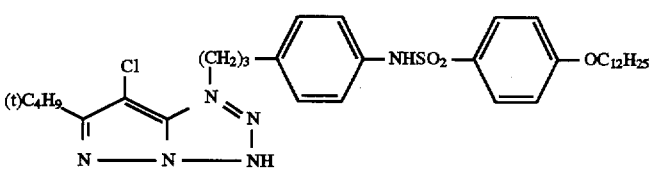
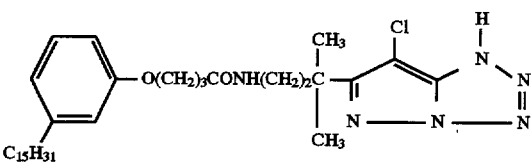
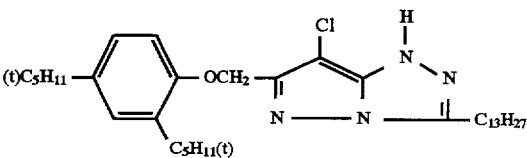
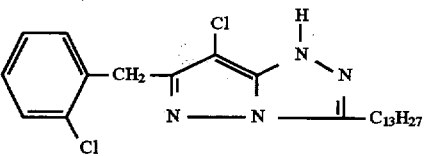

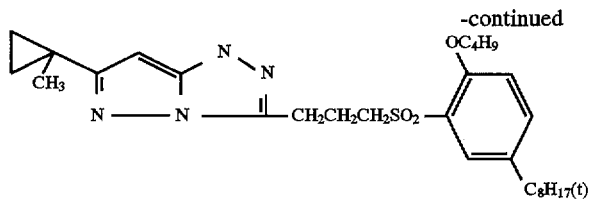
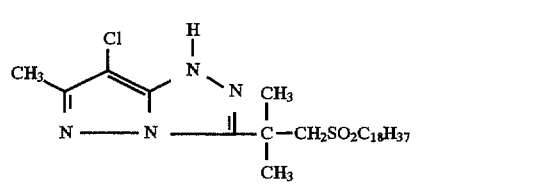
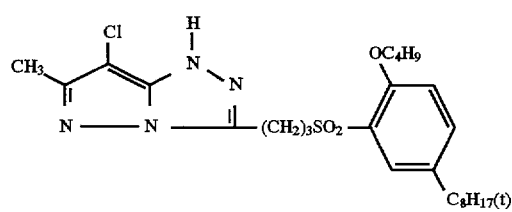
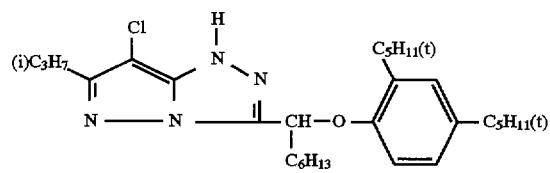
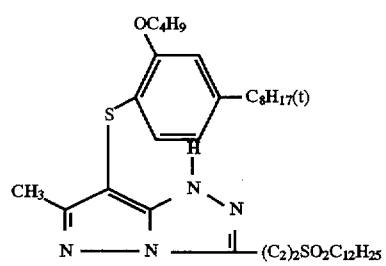
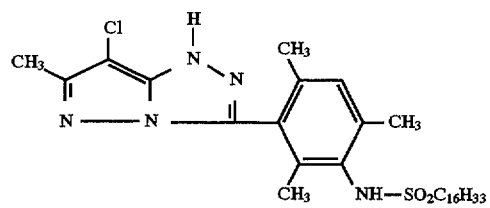
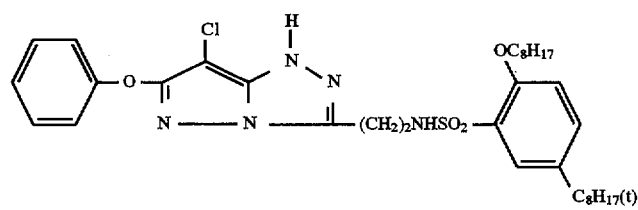
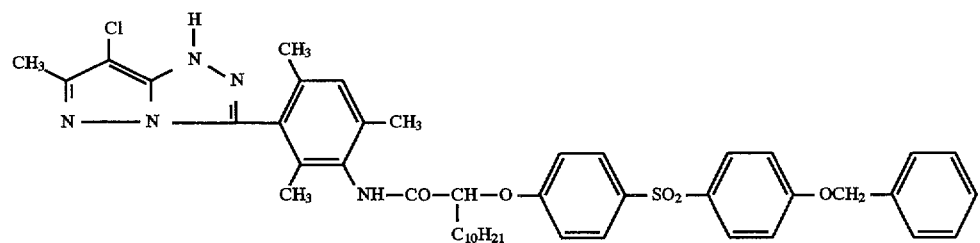

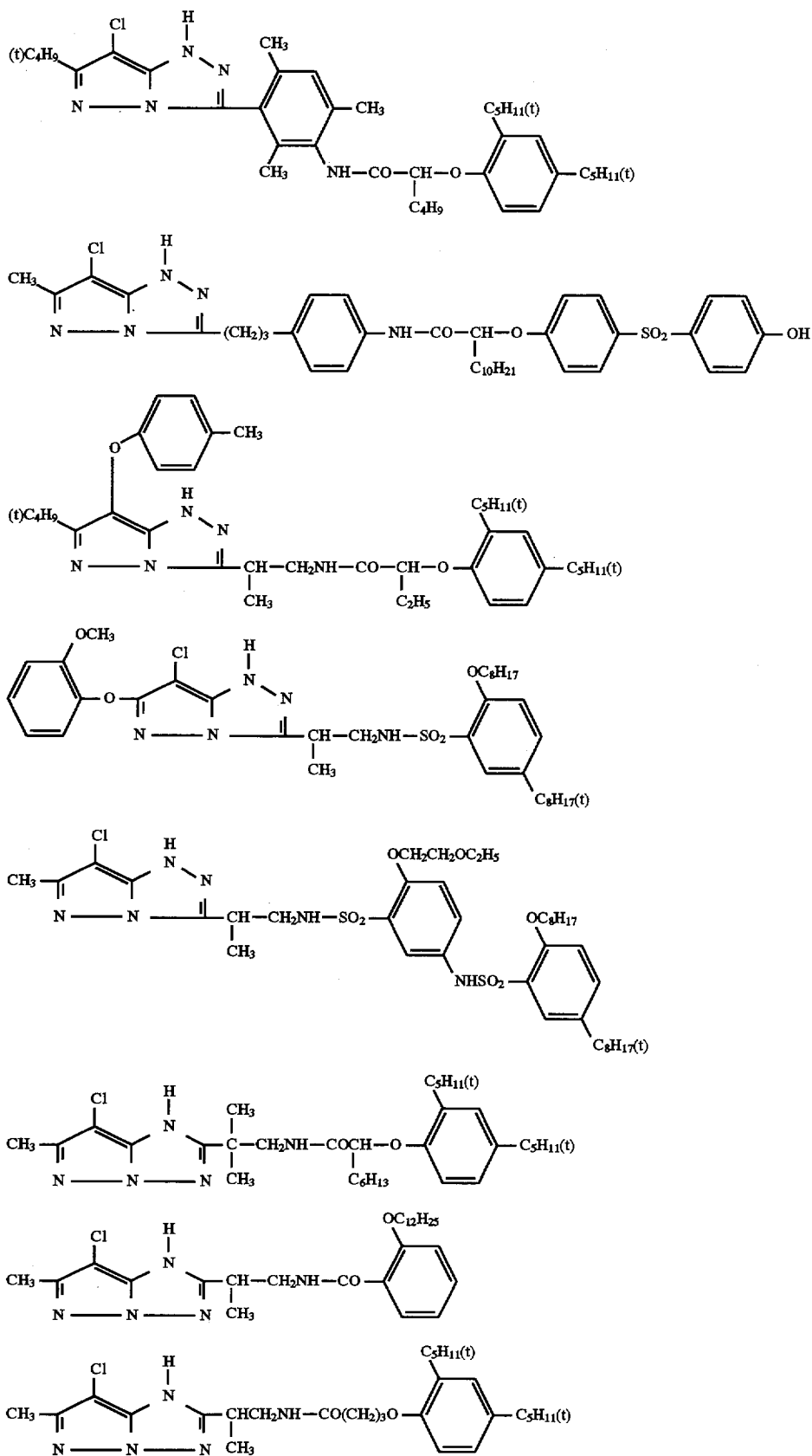

-continued
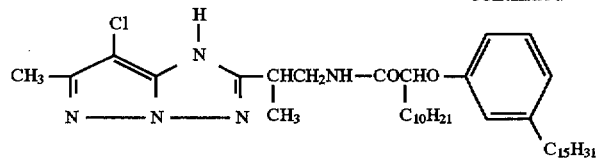
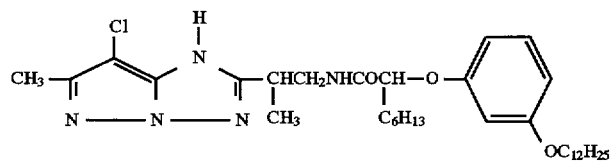
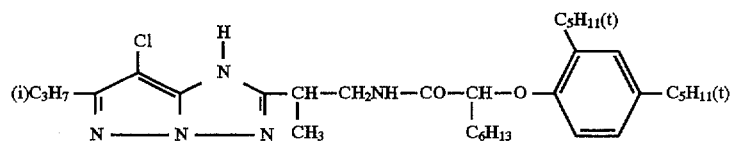
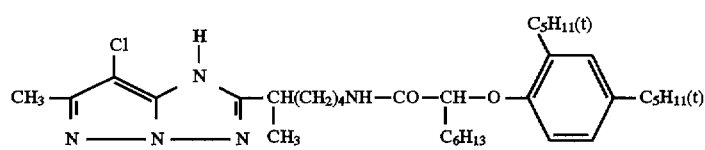
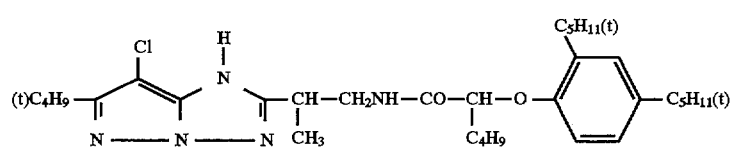
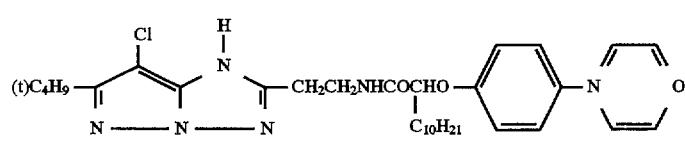
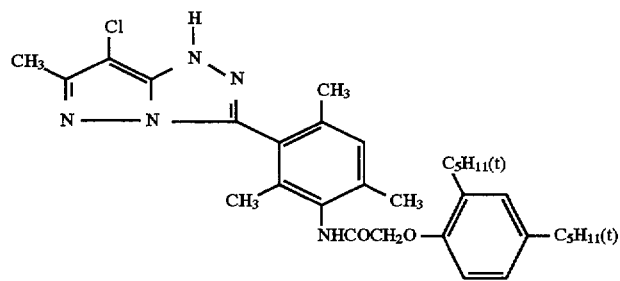
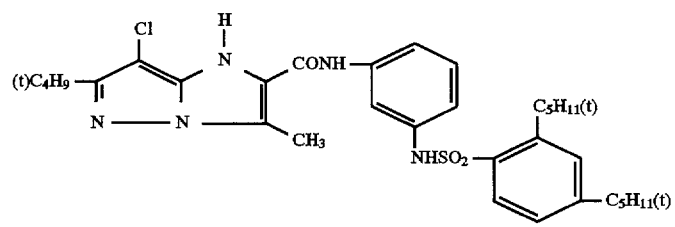
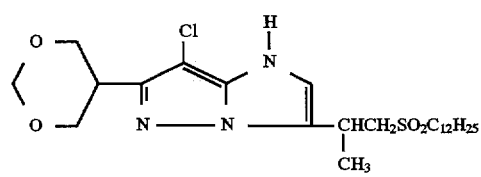

-continued

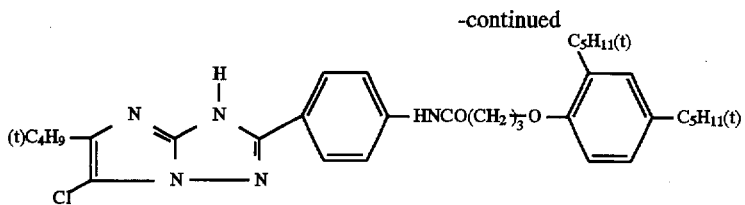

Cyan couplers may be, for example, derivatives of phenol, of 1-naphthol or of pyrazoloquinazolone. Preference is given to structures of the formula E

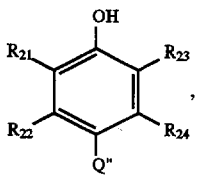
(E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group, $R_{23}$ is preferably an amino group and $R_{24}$ is preferably hydrogen. Q" is hydrogen (tetraequivalent couplers) or a leaving group (diequivalent couplers) which can be eliminated during the reaction with the oxidised developer. A detailed list of cyan couplers is given in U.S. Pat. No. 4,456,681.

The red-sensitive silver-halide emulsion layer of the material according to the invention preferably contains a cyan coupler of the formula

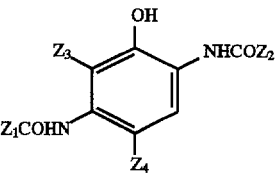
(E-12)

and/or of the formula

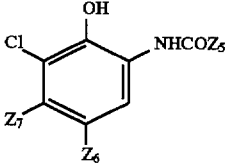
(E-13)

in which $Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together can form a ring, and $Z_4$ is hydrogen or a leaving group, and $Z_5$ is a ballast group, $Z_6$ is hydrogen or a leaving group and $Z_7$ is alkyl.

Examples of customary cyan couplers are the following:

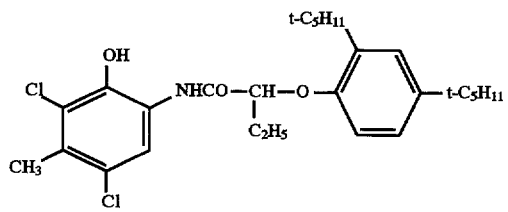
(E-1)

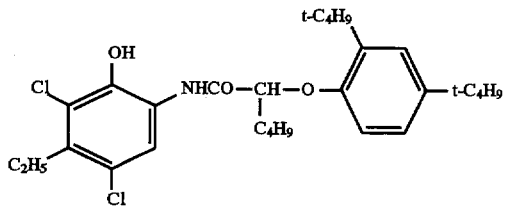
(E-2)

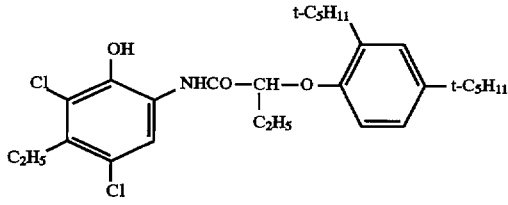
(E-3)

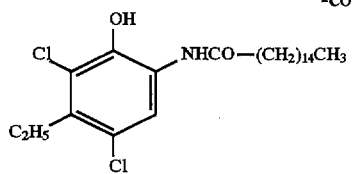
(E-4)
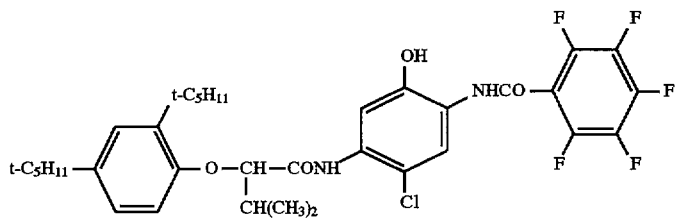
(E-5)
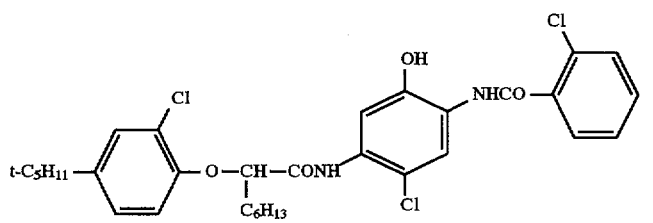
(E-6)
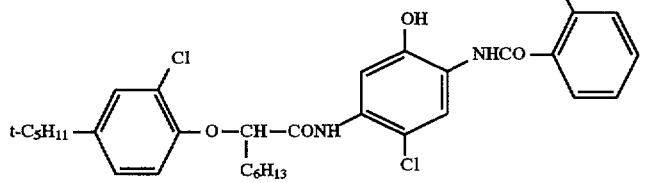
(E-7)
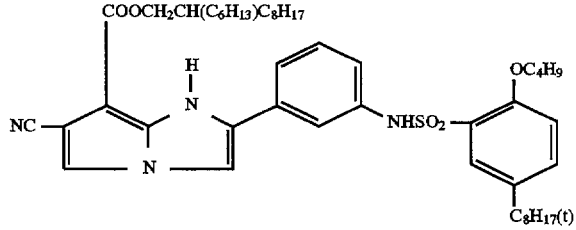
(E-8)
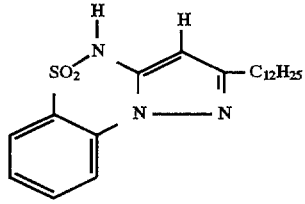
(E-9)
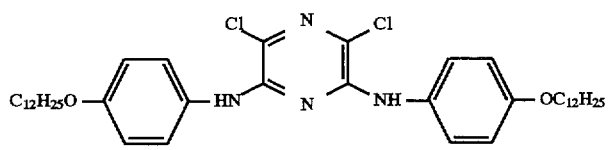
(E-10)
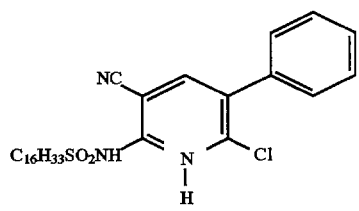
(E-11)
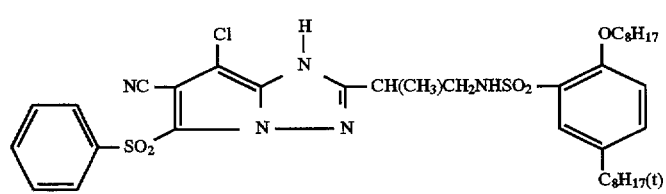

Further examples of cyan couplers are given in the following: U.S. Pat. Nos. 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183, 4,923,791, 5,143,824, 5,256,526, 5,269,181, 5,262,293, 5,270,153 and 5,306,610 and in EP-A-354 549 and EP-A-398 664, EP-A-0 456 226, EP-A-0 484 909, EP-A-0 487 111, EP-A-0 488 248, EP-A-0 491 197, EP-A-0 544316, EP-A-0 545 300, EP-A-0 545 305, EP-A-0 556 777, EP-A-0 578 248 and EP-A-0 608 133 and JP-A-3 240 053, 3 284 746, 4 009 050, 4 043 346, 4 125 557, 5 262 293, 5 306 610, 6 083 000 and 6 083 001.

The diequivalent couplers include those which are colourless and those which have an intense inherent colour which, on colour coupling, disappears or is replaced by the colour of the image dye formed (mask couplers), and white couplers which form essentially colourless products on reaction with colour developer oxidation products. The diequivalent couplers furthermore include couplers which contain, at the coupling point, a leaving group which is liberated on reaction with colour developer oxidation products and exhibits a certain desired photographic activity, for example as a development inhibitor or accelerator, either directly or after one or more further groups have been cleaved off from the radical cleaved off first (for example DE-A-2 703 145, DE-A-2 855 697, DE-A-3 105 026 and DE-A-3 319 428). Examples of such diequivalent couplers are known DIR couplers and DAR and FAR couplers.

Examples of white couplers are:

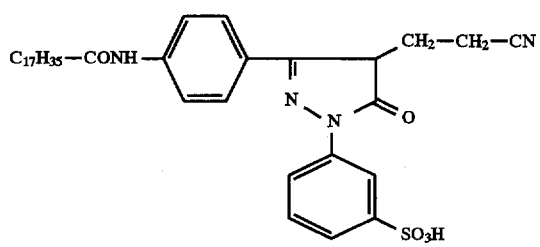

W-1

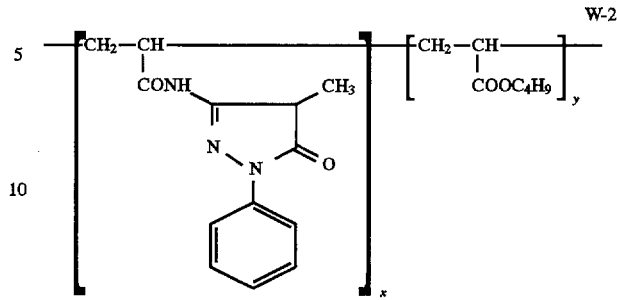

W-2

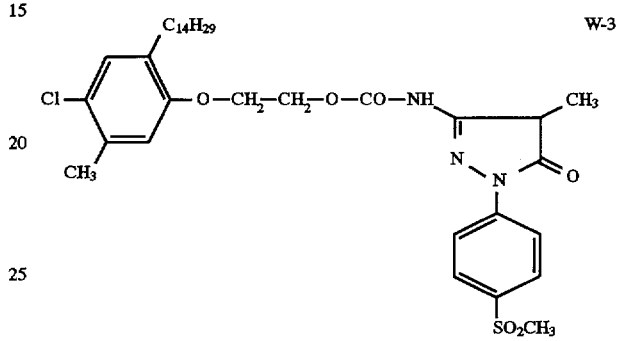

W-3

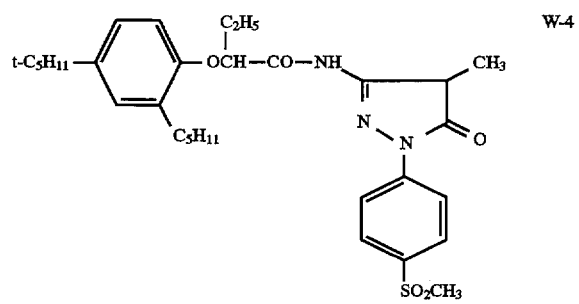

W-4

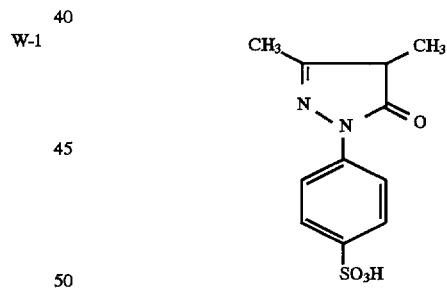

W-5

Examples of mask couplers are:

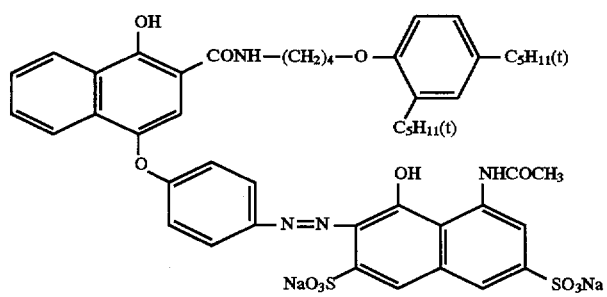

RM-1

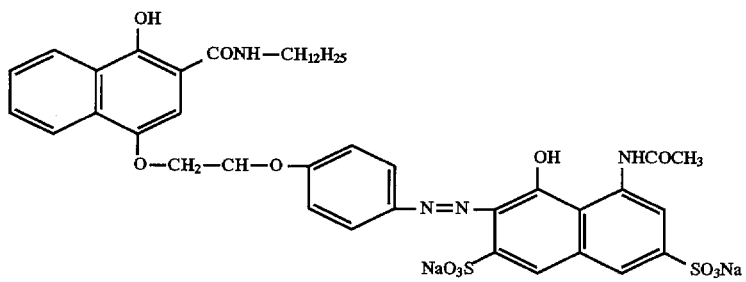
RM-2
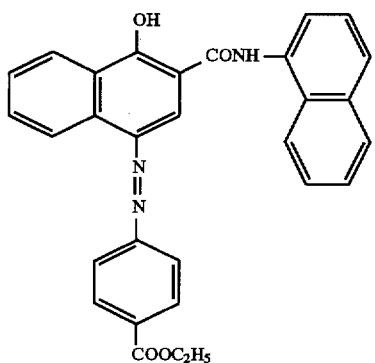
RM-3
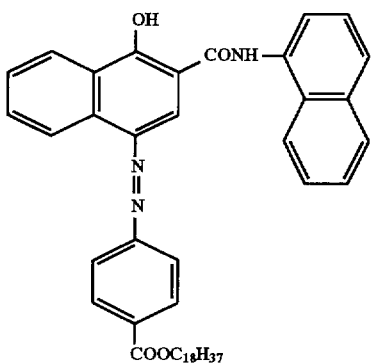
RM-4
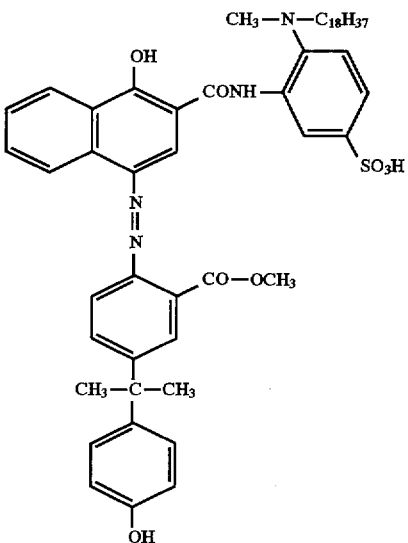
RM-5

-continued
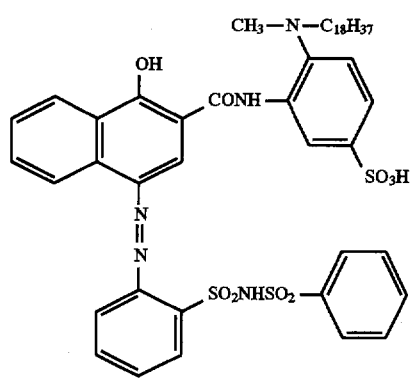
RM-6
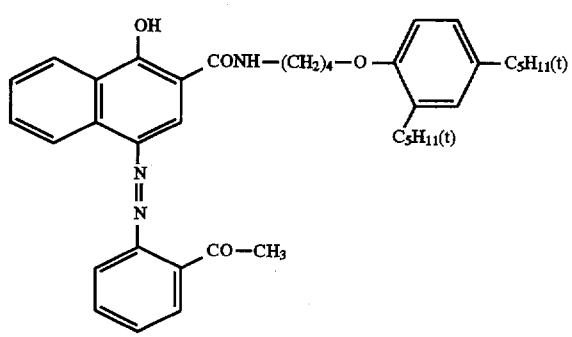
RM-7
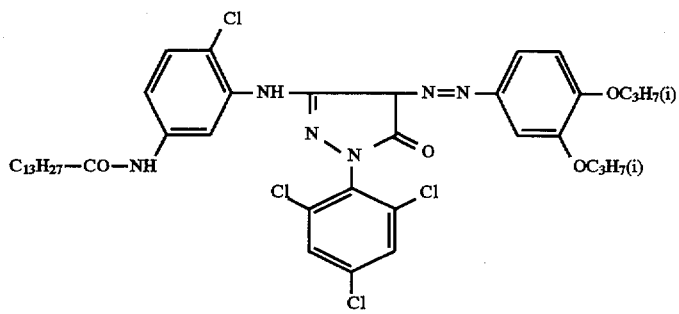
YM-1
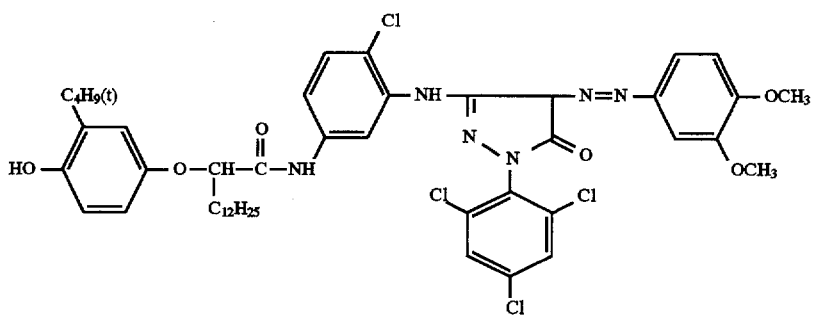
YM-2
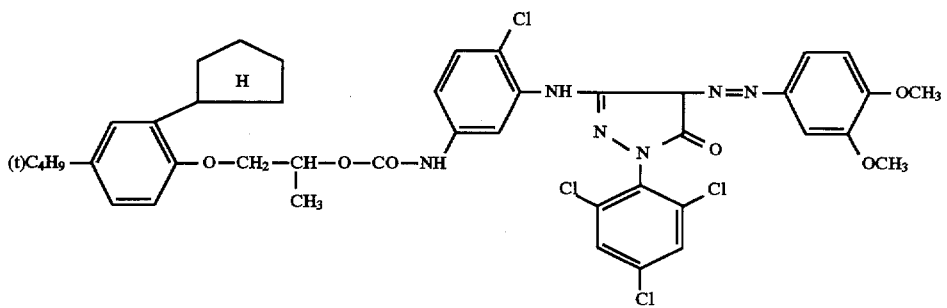
YM-3

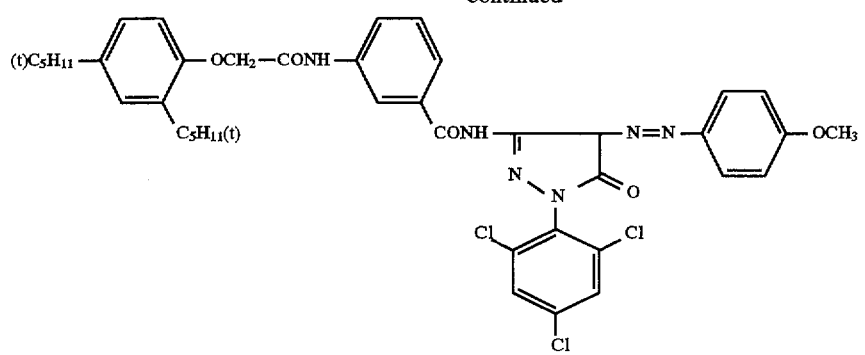
YM-4
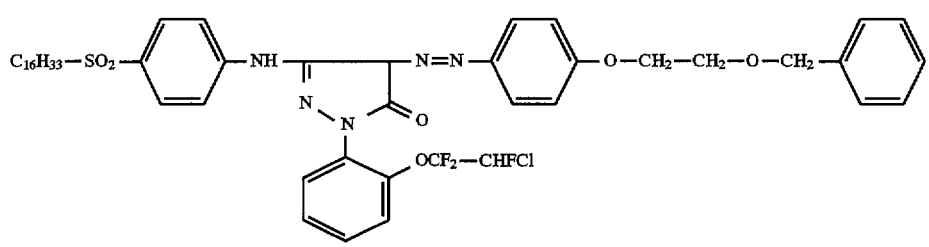
YM-5
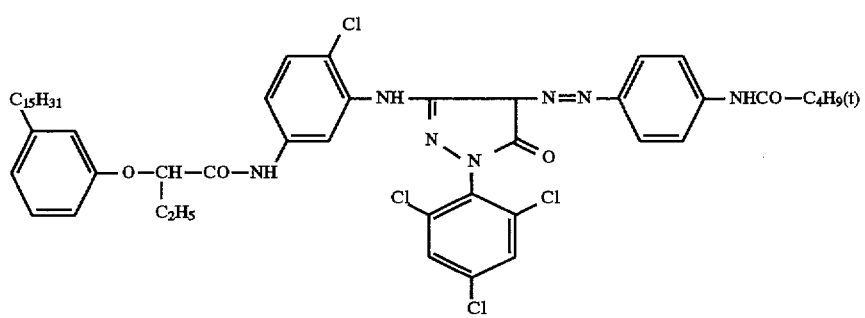
YM-6
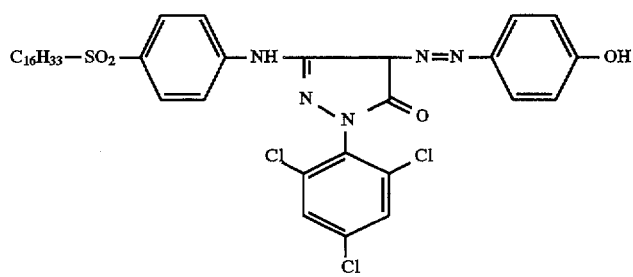
YM-7
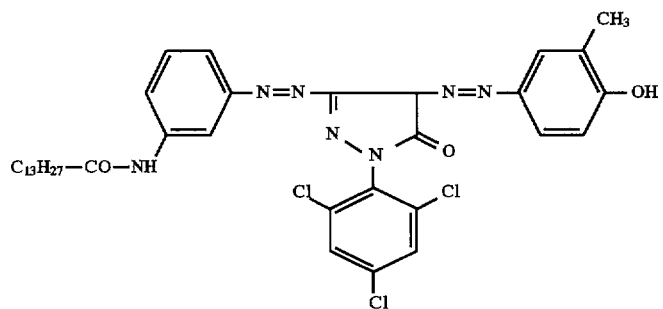
YM-8

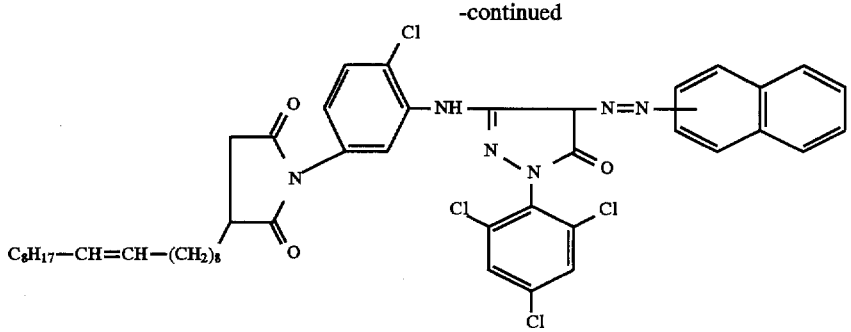

YM-9

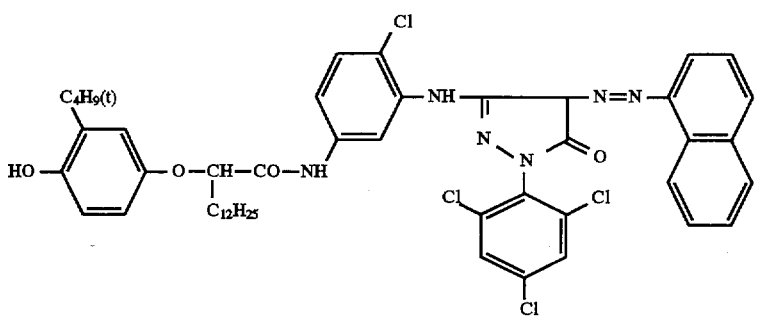

YM-10

DIR couplers, which liberate development inhibitors of the azole type, for example triazoles and benzotriazoles, are described in DE-A-2 414 006, 2 610 546, 2 659 417, 2 754 281, 2 842 063, 3 626 219, 3 630 564, 3 636 824 and 3 644 416. Further advantages for colour reproduction, i.e. colour separation and colour purity, and for detail reproduction, i.e. sharpness and granularity, can be achieved using DIR couplers which, for example, do not liberate the development inhibitor directly as a consequence of coupling with the oxidized colour developer, but instead only do so after a further reaction, which is achieved, for example, with a time-control group. Examples thereof are described in DE-A-2 855 697, 3 299 671, 3 818 231 and 3 518 797, in EP-A-0 157 146 and 0 204 175, in U.S. Pat. Nos. 4,146,396 and 4,438,393, and in GB-A-2 072 363.

DIR couplers which release a development inhibitor which is decomposed in the developer bath to give products which are essentially inactive in photographic terms are described, for example, in DE-A-3 209 486 and EP-A-0 167 168 and 0 219 713. This measure achieves flawless development and processing constancy.

On the use of DIR couplers, in particular those which eliminate a readily diffusable development inhibitor, suitable measures during optical sensitization allow improvements to be achieved in colour reproduction, for example differentiated colour reproduction, as described, for example, in EP-A-0 115 304, and 0 167 173, GB-A-2 165 058, DE-A-3 700 419 and U.S. Pat. No. 4,707,436.

In a multilayer photographic material, the DIR couplers can be added to a wide variety of layers, including, for example, light-insensitive layers or interlayers. However, they are preferably added to the photosensitive silver-halide emulsion layers, the characteristic properties of the silver-halide emulsions, for example their iodide content, the structure of the silver-halide grains or their grain-size distribution, affecting the photographic properties achieved. The effect of the inhibitors liberated can be limited, for example, by incorporating an inhibitor scavenger layer as described in DE-A-2 431 223. For reactivity or stability reasons, it may be advantageous to employ a DIR coupler which, in the particular layer containing it, forms, on coupling, a colour different from the colour to be generated in this layer.

In order to increase the sensitivity, the contrast and the maximum density, use can be made, in particular, of DAR or FAR couplers which release a development accelerator or a fogging agent. Compounds of this type are described, for example, in DE-A-2 534 466, 3 209 110, 3 333 355, 3 410 616, 3 429 545, 3 441 823, in EP-A-0 089 834, 0 110 511, 0 118 087 and 0 147 765, and in U.S. Pat. Nos. 4,618,572 and 4,656,123.

For an example of use in BAR (bleach accelerator releasing) couplers, reference is made to EP-A-193 389.

It may be advantageous to modify the effect of a photographically active group released from a coupler so that an intermolecular reaction of this group with another group occurs after its release, as described in DE-A-3 506 805.

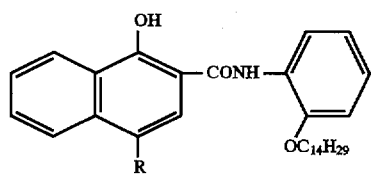

R=

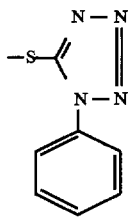

DIR-1

R=
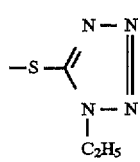
R=
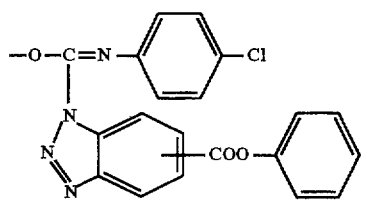
DIR-2
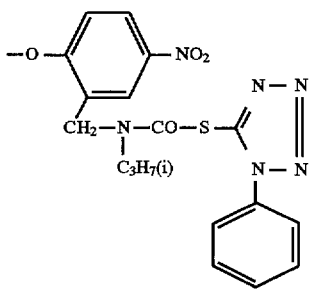 DIR-4
DIR-3
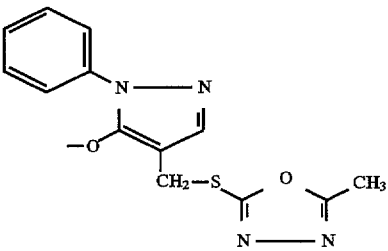 DIR-5
R=
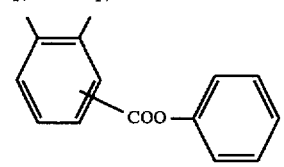 DIR-6
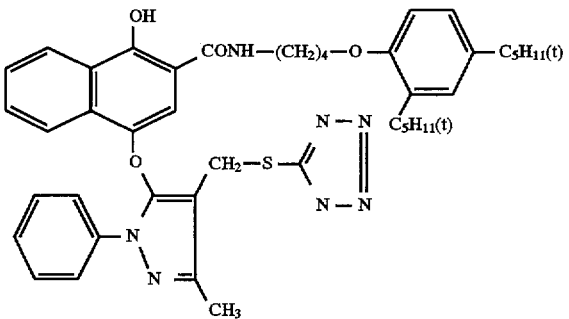 DIR-7
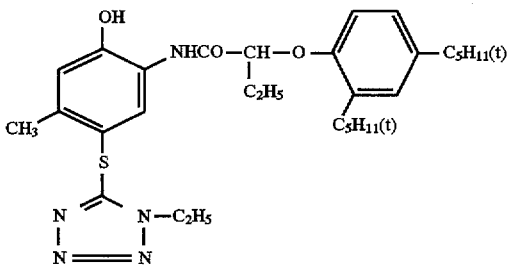 DIR-8

-continued
DIR-9
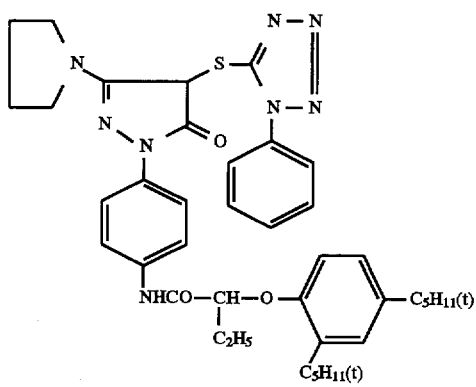
DIR-10
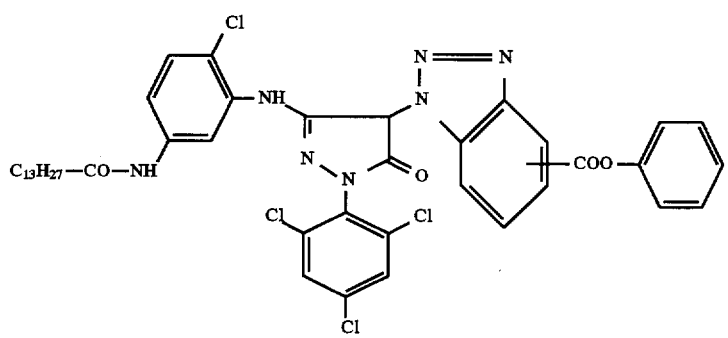
DIR-11
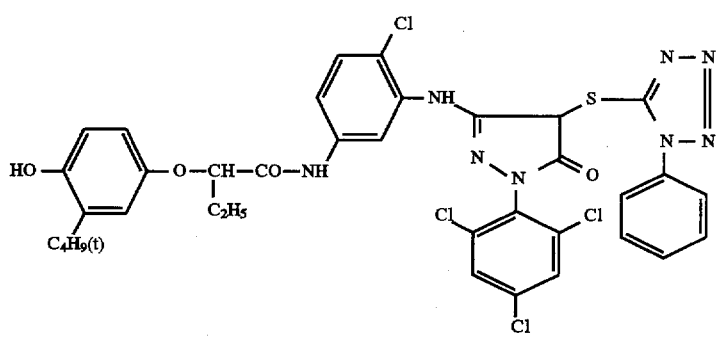
DIR-12
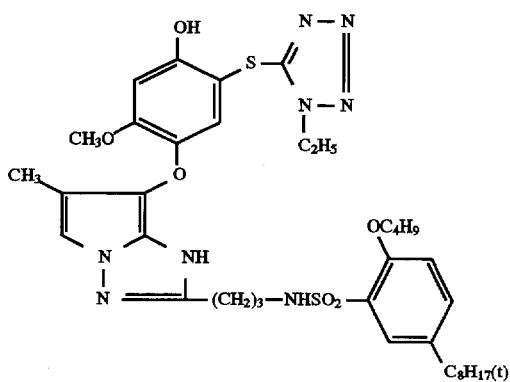

-continued
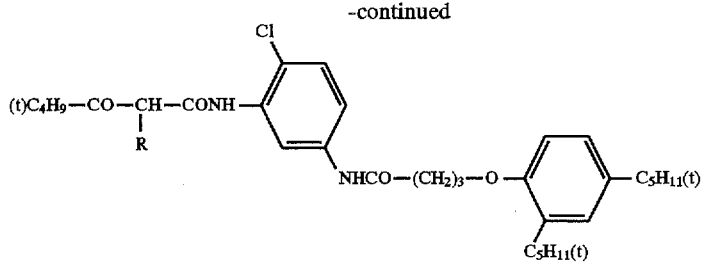
R=
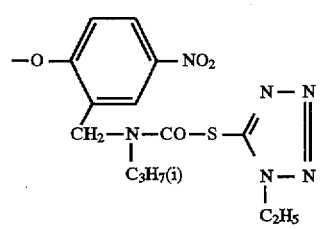
DIR-13
R=
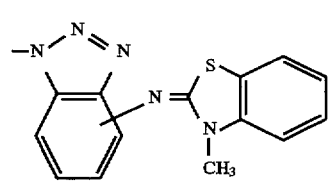
DIR-14
R=
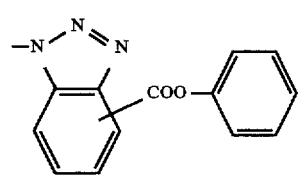
DIR-15
R=
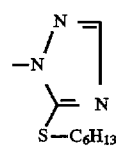
DIR-16
R=
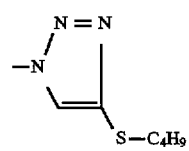
DIR-17
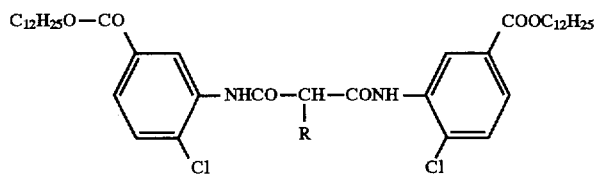
R=
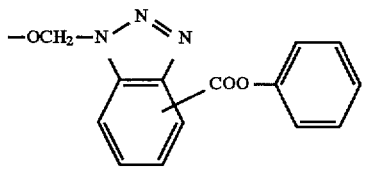
DIR-18
R=
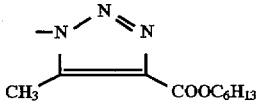
DIR-19
R=
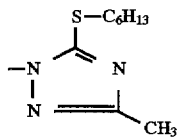
DIR-20

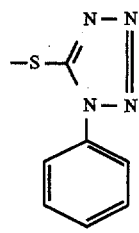
DIR-21
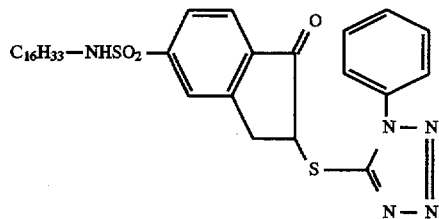
DIR-22
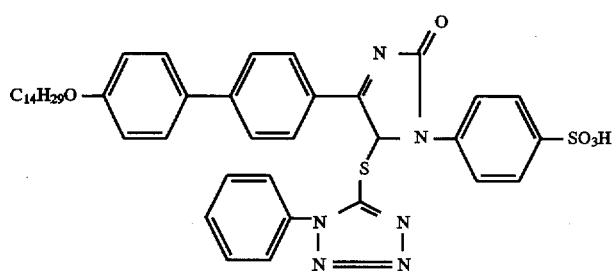
DIR-23
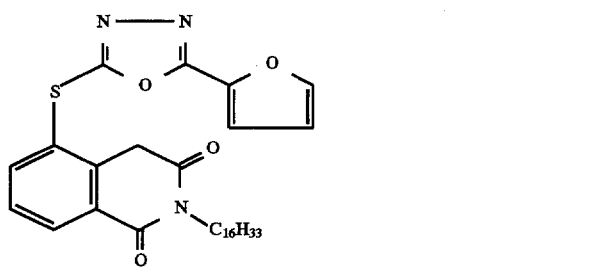
DIR-24
Examples of DAR couplers are the following:
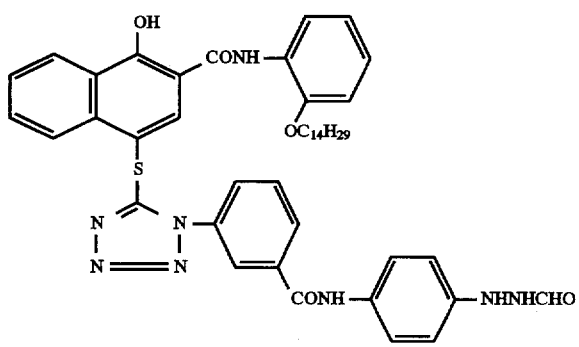
DAR-1
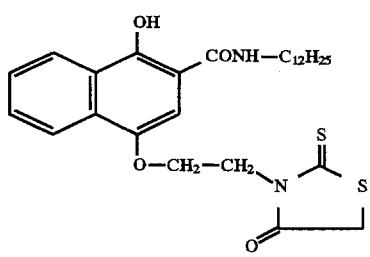
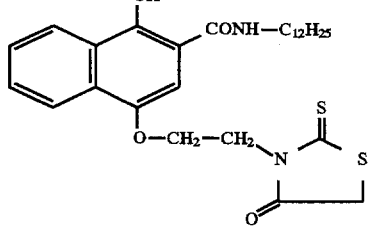
DAR-2

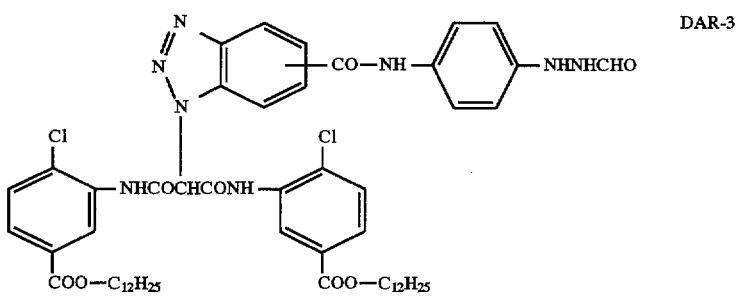

DAR-3

Since, in DIR, DAR and FAR couplers, it is principally the activity of the radical released on coupling that is desired and the colour-forming properties of these couplers are less important, suitable DIR, DAR and FAR couplers include those which give essentially colourless products on coupling (DE-A-1 547 640).

The radical which can be released may also be a balanced radical, so that reaction with colour developer oxidation products gives coupling products which are diffusable or at least have low or restricted mobility (U.S. Pat. No. 4,420, 556).

The material may furthermore contain compounds other than couplers, which can release, for example, a development inhibitor, a development accelerator, a bleach accelerator, a developer, a silver-halide solvent, a fogging agent or an antifogging agent, for example DIR hydroquinones or other compounds, as described, for example, in U.S. Pat. Nos. 4,636,546, 4,345,024 and 4,684,604, and in DE-A-3 145 640, 2 515 213, 2 447 079 and in EP-A-198 438. These compounds fulfil the same function as the DIR, DAR or FAR couplers, but do not form coupling products.

High-molecular-weight colour couplers are described, for example in DE-A-1 297 4 17, DE-A-2 407 569, DE-A-3 148 125, DE-A-3 217 200, DE-A-3 320 079, DE-A-3 324 932, DE-A-3 331 743, DE-A-3 340 376, EP-A-27 284 and U.S. Pat. No. 4,080,211. The high-molecular-weight colour couplers are generally prepared by polymerization of ethylenically unsaturated, monomeric colour couplers. However, they can also be obtained by polyaddition or polycondensation. The couplers or other compounds can be incorporated into silver-halide emulsion layers by first preparing a solution, dispersion or emulsion of the compound in question and then adding this to the casting solution for the layer in question. The choice of suitable solvent or dispersion medium depends on the particular solubility of the compound.

Methods for incorporating compounds which are essentially insoluble in water by grinding processes are described, for example, in DE-A-2 609 741 and DE-A-2 609 742.

Hydrophobic compounds can also be introduced into the casting solution using high-boiling solvents, known as oil formers. Corresponding methods are described, for example, in U.S. Pat. Nos. 2,322,027, 2,801,170, 2,801,171 and EP-A-0 043 037.

The high-boiling solvents can also be replaced by oligomers or polymers, known as polymeric oil formers.

The compounds can also be introduced into casting solution in the form of loaded lattices. Reference is made, for example, to DE-A-2 541 230, DE-A-2 541 274, DE-A-2 835 856, EP-A-0 014 921, EP-A-0 069 671, EP-A-0 130 115 and U.S. Pat. No. 4,291,113.

The diffusion-resistant incorporation of anionic, water-soluble compounds (for example dyes) can also be effected with the aid of cationic polymers, known as mordant polymers.

The UV absorbers of the formula I according to the invention can be incorporated into the colour-photographic material alone or together with the colour coupler and any further additives by pre-dissolving them in high-boiling organic solvents.

Examples of suitable high-boiling solvents are alkyl phthalate, phosphonates, phosphates, citrates, benzoates, amides, fatty acid esters, trimesates, alcohols, phenols, anilin derivatives and hydrocarbons.

Examples of suitable high-boiling solvents are dibutyl phthalate, dicyclohexyl phthalate, di-2-ethylhexyl phthalate, decyl phthalate, triphenyl phosphate, tricresyl phosphate, 2-ethylhexyl diphenyl phosphate, tridecyl phosphate, tributoxyethyl phosphate, trichloropropyl phosphate, di-2-ethylhexyl phenyl phosphate, 2-ethylhexyl benzoate, dodecyl benzoate, 2-ethylhexyl p-hydroxybenzoate, diethyldodecanamide, N-tetradecylpyrrolidone, isostearyl alcohol, 2,4-di-t-amylphenol, dioctyl acetate, glycerol tributyrate, isostearyl lactate, trioctyl citrate, N,N-dibutyl-2-butoxy-5-t-octylanilin, paraffin, didecylbenzene and diisopropylnaphthalene.

Further details on high-boiling solvents which can be used are given in the publications below:

Phosphates: GB-A-791 219, BE-A-755 248, JP-A-76/76 739, 78/27 449, 78/218 252, 78/97 573, 79/148 133, 82/216 177, 82/93 323 and 83/216 177 and EP-A-265 296.

Phthalates: GB-A-791 219, JP-A-77/98 050, 82/93 322, 82/216 176, 82/218 251, 83/24 321, 83/45 699 and 84/79 888.

Amides: GB-A-791 129, JP-A-76/105 043, 77/13 600, 77/61 089, 84/189 556, 87/239 149, U.S. Pat. No. 928,741, EP-A-270 341 and WO 88/00 723.

Phenols: GB-A-820 329, FR-A-1 220 657, JP-A-69/69 946, 70/3 818, 75/123 026, 75/82 078, 78/17 914, 78/21 166, 82/212 114 and 83/45 699.

Other oxygen-containing compounds: U.S. Pat. Nos. 3,748,141, 3,779,765, JP-A-73/75 126, 74/101 114, 74/10 115, 75/101 625, 76/76 740, 77/61 089, EP-A-304 810 and BE-A-826 039.

Other compounds: JP-A-72/115 369, 72/130 258, 73/127 521, 73/76 592, 77/13 193, 77/36 294, 79/95 233, 91/2 748, 83/105 147 and Research Disclosure 82/21 918.

The amount of high-boiling solvent is, for example, in the range from 50 mg to 2 g per m² of base, preferably from 200 mg to 1 g per m².

If desired, the UV absorbers can also be dispersed in the gelatin layer without oil; Research Disclosure 88/296 017 and 89/303 070.

Furtherefore, the UV absorber or a mixture of UV absorbers can be introduced into at least one of the photographic layers in such a way that a latex containing small lipophilic particles (typical diameter 0.02 to 2 μm) is produced which contains both the UV absorber and a hydrophobic polymer.

A corresponding method is described, for example, in column 17 of U.S. Pat. No. 5,200,307 for benzotriazoles. UV absorbers of the formula I can, in accordance with the invention, be dissolved, alone or in combination with another UV absorber of the same or a different class, for example from the class of the 2-hydroxyphenylbenzotriazoles, be dissolved together with a hydrophobic polymer in a suitable organic solvent, for example ethyl acetate; this solution can subsequently be emulsified and dispersed to give a latex in water or aqueous gelatin. After removal of the organic solvent, the latex can be introduced into the photographic system. Examples of suitable hydrophobic polymers are homopolymers or copolymers as can be obtained by polymerization of ethylenically unsaturated monomers of the formulae II to VII described below:

(II) $R_{18}$—CH=C($R_{17}$)—C(=O)—X'—$R_{20}$, in which

X' is —O— or —$NR_{19}$—;

$R_{17}$ is H, $C_1$-$C_4$alkyl, —$CH_2$—$COOR_{21}$, —Cl or —CN;

$R_{18}$ is H, —$COOR_{21}$ or —$CH_3$;

$R_{19}$ is H, $C_1$-$C_8$alkyl, $C_4$-$C_{12}$cycloalkyl, —N($R_X$)$_2$-substituted $C_1$-$C_4$alkyl, —S(=O)—$R_X$, —C(CH$_3$)$_2$—CH$_2$—C(=O)—CH$_3$, —C(CH$_3$)$_2$—CH$_2$—SO$_3$M, —(CH$_2$)$_s$—SO$_3$M or

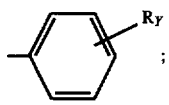
;

$R_{20}$ is H; $C_1$-$C_{18}$alkyl, $C_2$-$C_{18}$alkenyl, $C_2$-$C_{18}$alkyl which is interrupted by one or more O atoms and can be substituted by OH, or —(CH$_2$)$_s$—SO$_3$M;

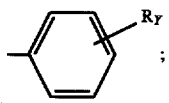
;

—CH$_2$F, —CH$_2$Cl, —CH$_2$CN, —CH$_2$CH$_2$Cl, —CH$_2$CH$_2$CN, —CH$_2$CH$_2$—COOR$_X$, $C_7$-$C_{11}$phenylalkyl, naphthyl, —N($R_X$)$_2$-substituted $C_1$-$C_4$alkyl, adamantyl or $C_6$-$C_{12}$cycloalkyl;

$R_{21}$ is H, $C_1$-$C_{18}$aralkyl, phenyl or $C_2$-$C_{18}$alkenyl;

$R_X$ is $C_1$-$C_4$alkyl or phenyl;

$R_Y$ is H, $C_1$-$C_{12}$alkyl, phenyl, —CO—OR$_X$, —CN, —F, or —Cl;

M is H or an alkali metal; and s is a number from 1 to 5.

(III) $R_{22}$—C(=O)—O—CH=CH$_2$, in which $R_{22}$ is $C_1$-$C_{19}$alkyl or phenyl.

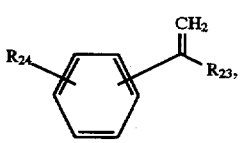
(IV)

in which $R_{23}$ is H or —CH$_3$;

$R_{24}$ is H, —C$R_{23}$=CH$_2$, —C(O)-phenyl or —SO$_3$M; and

M is H or an alkali metal.

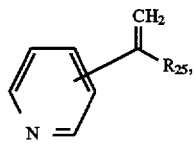
(V)

in which $R_{25}$ is H or —CH$_3$.

(VI) CH$_2$=C$R_{26}$—$R_{27}$, in which $R_{26}$ is H, —F, —Cl or —CH$_3$ and $R_{27}$ is —Cl, —Br, —F or —CN.

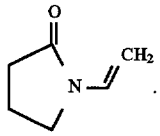
(VII)

In certain cases, the hydrophobic polymer can be a condensation polymer, for example a polyester such as 1,4-butanediol/adipic acid polyester or polycaprolactone. A high-boiling organic solvent can also be used in addition if, for example, the UV absorber employed is not liquid. Mixtures of suitable organic solvents can also be expediently employed.

The invention therefore also relates to a photographic recording material which, in at least one of the layers, contains a hydrophobic polymer in addition to the UV absorber. This polymer can be, for example, a hydrophobic homopolymer or copolymer of monomers of the formulae II to VII described above. This polymer preferably contains no polyoxyalkylene, no hydroxyl groups and no sulfone groups.

Another method, described analogously, for example, in GB-A-2 016 017 and U.S. Pat. No. 5,372,922, comprises adding the novel UV absorber to a latex prepared by emulsion polymerization as described above and comprising small, water-insoluble, solvent-containing particles; the UV absorber is then taken up by the particles. The loaded latex can subsequently be introduced into the photographic system.

The invention therefore furthermore relates to a photographic recording material comprising the UV absorber and the hydrophobic polymer in at least one of the layers, which material is obtainable by dissolving the UV absorber and the hydrophobic polymer in an organic solvent and then emulsifying and dispersing the solution in an aqueous medium and introducing the latex into the photographic system, and to a corresponding process for the production of a photographic recording material.

Each of the photosensitive layers of different sensitization can comprise a single layer or alternatively two or more silver-halide emulsion part-layers (DE-C-1 121 470). Red-sensitive silver-halide emulsion layers are frequently arranged closer to the layer base than are green-sensitive silver-halide emulsion layers, which are in turn arranged closer to the layer base than are blue-sensitive layers; in general, a non-photosensitive yellow filter layer is positioned between green-sensitive layers and blue-sensitive layers.

If the inherent sensitivity of the green- and red-sensitive layers is suitably low, other layer arrangements omitting the yellow filter layer can be chosen in which, for example, the blue-sensitive, then the red-sensitive and finally the green-sensitive layers are arranged on the base.

The non-photosensitive interlayers generally arranged between layers of different spectral sensitivity can contain agents which prevent undesired fusion of developer oxidation products from a photosensitive layer into another photosensitive layer of different spectral sensitization.

Suitable agents, also known as EOP scavengers, are described in Research Disclosure 17 643 (December 1978), Chapter VII, 17 842 (February 1979) and 18 716 (November 2979), page 650, and in EP-A-0 069 070, 0 098 072, 0 124 877 and 0 125 522.

Examples of particularly suitable compounds are:

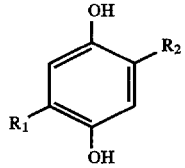

$R_1$ and $R_2$=
$C_8H_{17}(t)$
$C_{12}H_{25}(s)$
$C_6H_{13}(t)$

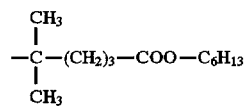

$C_8H_{17}(s)$
$C_{15}H_{31}(t)$

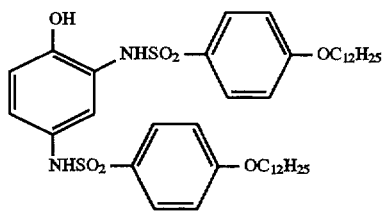

If the material contains a plurality of sub-layers of identical spectral sensitization, these can differ in composition, in particular regarding the type and amount of silver-halide grains. In general, the sub-layer of higher sensitivity will be arranged further from the base than will the sub-layer of lower sensitivity. Sub-layers of identical spectral sensitization can be adjacent to one another or separated by other layers, for example by layers of different spectral sensitization. For example, all high-sensitivity layers and all low-sensitivity layers can in each case be combined to form a layer packet (DE-A-1 958 709, DE-A-2 530 645 and DE-A-2 622 922).

The photographic material may furthermore contain UV absorbing compounds, white toners, spacers, filter dyes, formalin scavengers, light stabilizers, antioxidants, $D_{min}$ dyes, additives for improving the dye, coupler and white destabilization and for reducing colour casts, plasticizers (lattices), biocides, inter alia.

The photographic layers in the novel material, in particular layers b, c and/or d in the colour-photographic material described above by way of example, may also contain other UV absorbers. Examples of such UV absorbers are benzotriazoles, 2-hydroxybenzophenones, oxanilides, cyanoacrylates, salicylates, acrylonitrile derivatives and thiazolines.

Such UV absorbers are described in greater detail, for example, in the following publications: U.S. Pat. Nos. 3,314,794, 3,352,681, 3,705,805, 3,707,375, 4,045,229, 3,700,455, 3,700,458, 3,533,794, 3,698,907, 3,705,805, 3,738,837, 3,762,272, 4,163,671, 4,195,999, 4,309,500, 4,431,726, 4,443,543, 4,576,908 and 4,749,643, GB-A-1 564 089, EP-A-190 003 and JP-A-71/2784, 81/111 826, 81/27 146, 88/53 543 and 88/55 542. Preferred UV absorbers are benzotriazoles, in particular 2-(2-hydroxyphenyl)benzotriazoles.

Preference is also given to a photographic recording material additionally comprising a UV absorber from the hydroxyphenyltriazine series which does not conform to the formula (I), as described, for example, in U.S. Pat. No. 5,300,414 and U.S. Pat. No. 5,364,749.

Examples of particularly suitable compounds are:

Benzotriazole compounds of the formula AII

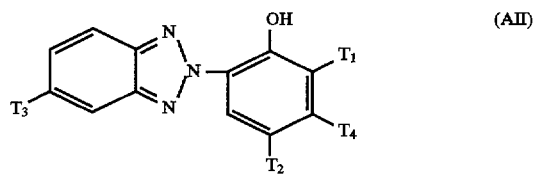

in which $T_1$, $T_2$ and $T_3$, independently of one another, are hydrogen, halogen, alkyl, carboxylate-substituted alkyl, alkoxy, aryloxy, hydroxyl or acyloxy, and $T_4$ is hydrogen, alkoxy, aryloxy or acyloxy.

Examples of HBT compounds of the formula AII are:

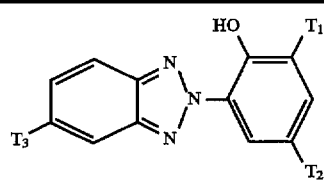

| HBT No. | $T_1$ | $T_2$ | $T_3$ |
|---|---|---|---|
| HBT-1 | H | $CH_3$ | H |
| HBT-2 | H | $C(CH_3)_3$ | H |
| HBT-3 | $C(CH_3)_3$ | $CH_3$ | Cl |
| HBT-4 | $C(CH_3)_3$ | $C(CH_3)_3$ | Cl |
| HBT-5 | $C(CH_3)_2C_2H_5$ | $C(CH_3)_2C_2H_5$ | H |
| HBT-6 | $CH(CH_3)C_2H_5$ | $C(CH_3)_3$ | H |
| HBT-7 | $C(CH_3)_2$-Ph | $C(CH_3)_2$-Ph | H |
| HBT-8 | $C(CH_3)_3$ | $CH_2CH_2COOC_8H_{17}$ (Isomers)* | Cl |
| HBT-9 | $C(CH_3)_3$ | $CH_2CH_2COOC_8H_{17}$ (Isomers)* | H |
| HBT-10 | $C_{12}H_{25}$ (Isomers)* | $CH_3$ | H |

*Principal product

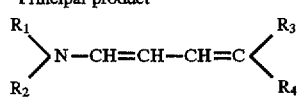

$R_1$ and $R_2$=—$C_6H_{13}(n)$; $R_3$ and $R_4$=—CN $R_1$ and $R_2$=—$C_2H_5$; $R_3$=

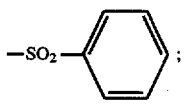

$R_4$=—CO—$OC_8H_{17}$ $R_1$ and $R_2$=—$C_2H_5$; $R_3$=

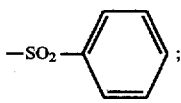

$R_4$=—COO—$C_{12}H_{25}$ $R_1$ and $R_2$=—$CH_2$=CH—$CH_2$; $R_3$ and $R_4$=—CN

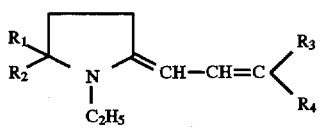

$R_1$ and $R_2$=H; $R_3$=—CN; $R_4$=—CO—$NHC_{12}H_{25}$ $R_1$ and $R_2$=—$CH_3$; $R_3$=—CN; $R_4$=—CO—$NHC_{12}H_{25}$

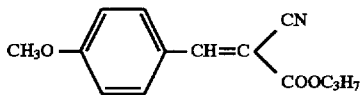

It is also possible to use UV-absorbing couplers (such as cyan couplers of of the α-naphthol type) and UV-absorbing polymers. These UV absorbers can be fixed in a specific layer by mordants.

Filter dyes which are suitable for visible light include oxonol dyes, hemioxonol dyes, styryl dyes, merocyanine dyes, cyanine dyes and azo dyes. Of these dyes, oxonol dyes, hemioxonol dyes and merocyanine dyes are particularly advantageous.

Examples of suitable white toners are described in Research Disclosure 17 643 (December 1978), Chapter V, in U.S. Pat. No. 2,632,701 and U.S. Pat. No. 3,269,840, and in GB-A-852 075 and 1 319 763.

Certain binder layers, in particular the layer furthest removed from the base, but also occasionally interlayers, in particular if they form the layer furthest removed from the base during production, may contain photographically inert particles of an inorganic or organic nature, for example as matting agents or as spacers (DE-A-3 331 542; DE-A-3 424 893 and Research Disclosure 17 643 (December 1978), Chapter XVI).

The mean particle diameter of the spacers is, in particular, in the range from 0.2 to 2 μm. The spacers are water-insoluble and can be alkali-insoluble or alkali-soluble, the alkali-soluble spacers generally being removed from the photographic material in the alkaline development bath. Examples of suitable polymers are polymethyl acrylate, copolymers of acrylic acid and methyl methacrylate, and hydroxypropylmethylcellulose hexahydrophthalate.

Suitable formalin scavengers are, for example:

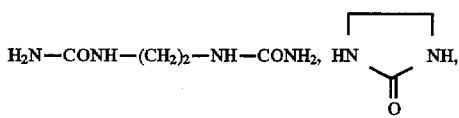

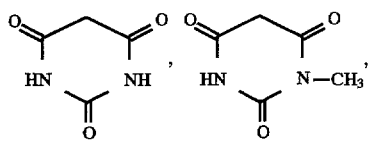

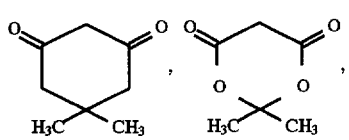

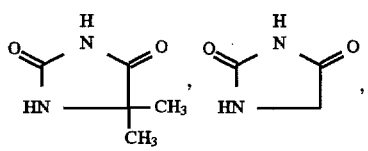

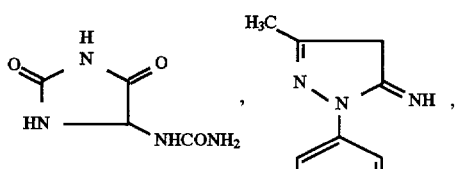

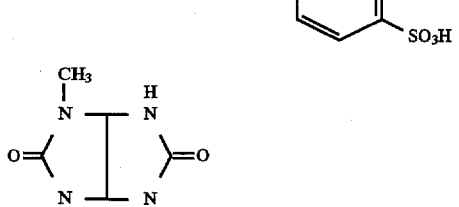

The photographic layers may also contain phenolic compounds which act as light stabilisers for the colour image and as colour cast inhibitors. They may be present in a photosensitive layer (colour layer) or in an interlayer, alone or together with other additives. Such compounds are described in greater detail, for example, in the publications below: U.S. Pat. Nos. 3,700,455, 3,591,381, 3,573,052, 4,030,931, 4,174,220, 4,178,184, 4,228,235, 4,268,593, 4,279,990, 4,346,165, 4,366,226, 4,447,523, 4,528,264, 4,581,326, 4,562,146 and 4,559,297, GB-A-1 309 277, 1 547 302, 2 023 862, 2 135 788, 2 139 370 and 2 156 091; DE-A-2 301 060, 2 347 708, 2 526 468, 2 621 203 and 3 323 448; DD-A-200 691 and 214 468; EP-A-106 799, 113 124, 125 522, 159 912, 161 577, 164 030, 167 762, 176 845, 246 766, and 320 776; JP-A-74/134 326, 76/127 730, 76/30 462, 77/3 822, 77/154 632, 78/10 842, 79/48 535, 79/70 830, 79/73 032, 79/147 038, 79/154 325, 79/155 836, 82/142 638, 83/224 353, 84/5 246, 84/72 443, 84/87 456, 84/192 246, 84/192 247, 84/204 039, 84/204 040, 84/212 837, 84/220 733, 84/222 836, 84/228 249, 86/2 540, 86/8 843, 86/18 835, 86/18 836, 87/11 456, 87/42 245, 87/62 157, 86/6 652 and 89/137 258 and in Research Disclosure 79/17 804.

The photographic layers may also contain certain phosphorus(III) compounds, in particular phosphites and phosphonites. These act as light stabilisers for the colour images and as dark-storage stabilisers for magenta couplers. They are preferably added to the high-boiling solvents together with the coupler. Phosphorus(III) compounds of this type are described in greater detail, for example, in the publications below: U.S. Pat. No. 4,407,935, U.S. Pat. No. 4,436,811, U.S. Pat. No. 4,956,406, EP-A-181 289, JP-A-73/32 728, JP-A-76/1 420 and JP-A-55/66 741.

The photographic layers may also contain organometallic complexes which are light stabilisers for the colour images, in particular for the magenta dyes. Such compounds and combinations thereof with other additives are described in greater detail, for example, in the publications below: U.S. Pat. Nos. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165 and 4,590,153; JP-A-81/167 138, 81/168 652, 82/30 834 and 82/161 744; EP-A-137 271, 161 577 and 185 506; DE-A-2 853 865.

The photographic layers may also contain hydroquinone compounds. These act as light stabilsers for the colour couplers and for the colour images and as scavengers of oxidized developer in interlayers. They are used in particular in the magenta layer. Hydroquinone compounds of this type and combinations thereof with other additives are described in greater detail, for example, in the publications below: U.S. Pat. Nos. 2,360,290, 2,336,327, 2,403,721, 2,418,613, 2,675,314, 2,701,197, 2,710,801, 2,732,300, 2,728,659, 2,735,765, 2,704,713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572 and 4,559,297, FR-A-885 982; GB-A-891 158, 1 156 167, 1 363 921, 2 022 274, 2 066 975, 2 071 348, 2 081 463, 2 117 526 and 2 156 091; DE-A-2 408 168, 2 726 283, 2 639 930, 2 901 520, 3 308 766, 3 320 483 and 3 323 699; DD-A-216 476, 214 468, 214 469, EP-A-84 290, 110 214, 115 305, 124 915, 124 877, 144 288, 147 747, 178 165 and 161 577; JP-A-75/33 733, 75/21 249, 77/128 130, 77/146 234, 79/70 036, 79/133 131, 81/83 742, 81/87 040, 81/109 345, 83/134 628, 82/22 237, 82/112 749, 83/17 431, 83/21 249, 84/75 249, 84/149 348, 84/182 785, 84/180 557, 84/189 342, 84/228 249, 84/101 650, 79/24 019, 79/25 823, 86/48 856, 86/48 857, 86/27 539, 86/6 652, 86/72 040, 87/11 455 and 87/62 157, and in Research Disclosure 79/17 901, 79/17 905, 79/18 813, 83/22 827 and 84/24 014.

The photographic layers may also contain derivatives of hydroquinone ethers. These compounds act as light stabilisers and are particularly suitable for stabilising magenta dyes. Such compounds and combinations thereof with other additives are described in greater detail, for example, in the publications below: U.S. Pat. Nos. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,134,011, 4,273,864, 4,264,720, 4,279,990, 4,332,886, 4,436,165, 4,360,589, 4,416,978, 4,385,111, 4,459,015 and 4,559,297; GB-A 1 347 556, 1 366 441, 1 547 392, 1 557 237 and 2 135 788; DE-A 3 214 567; DD-214 469, EP-A 161 577, 167 762, 164 130 and 176 845; JP-A 76/123 642, 77/35 633, 77/147 433, 78/126, 78/10 430, 78/53 321, 79/24 019, 79/25 823, 79/48 537, 79/44 521, 79/56 833, 79/70 036, 79/70 830, 79/73 032, 79/95 233, 79/145 530, 80/21 004, 80/50 244, 80/52 057, 80/70 840, 80/139 383, 81/30 125, 81/151 936, 82/34 552, 82/68 833, 82/204 306, 82/204 037, 83/134 634, 83/207 039, 84/60 434, 84/101 650, 84/87 450, 84/149 348, 84/182 785, 86/72 040, 87/11 455, 87/62 157, 87/63 149, 86/2 151, 86/6 652, 86/48 855 and 89/309 058 and in Research Disclosure 78/17 051.

The photographic layers, and especially the layers containing the UV absorber of the invention, may also contain sterically hindered amine light stabilizers (HALS), examples are the compounds which have been described above already as coadditives for the coating application of the instant UV absorbers. Some especially suitable stabilizers are those mentioned in the above list of coadditives under point 2.6.

Examples of particularly suitable compounds are:

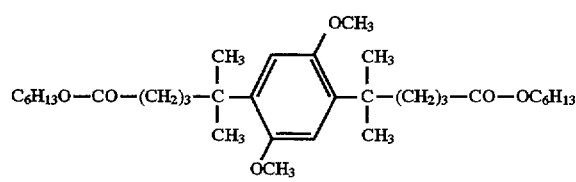
(ST-1)

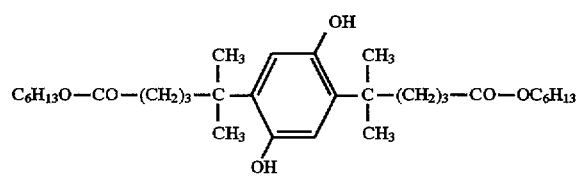
(ST-2)

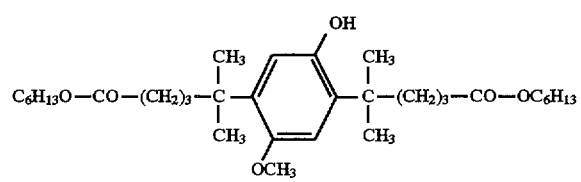
(ST-3)

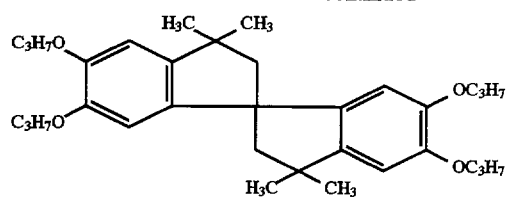
(ST-4)
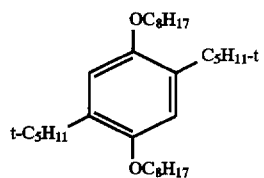
(ST-5)
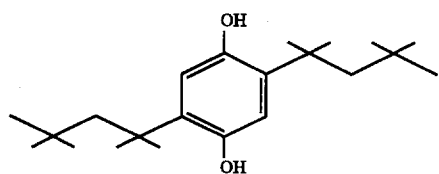
(ST-6)
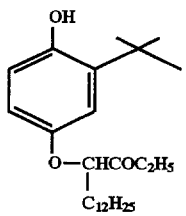
(ST-7)
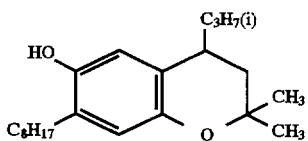
(ST-8)
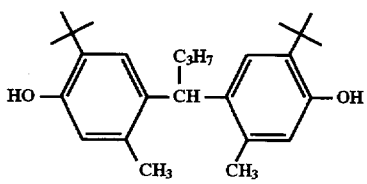
(ST-9)
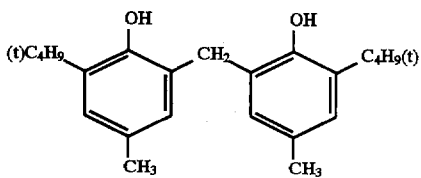
(ST-10)
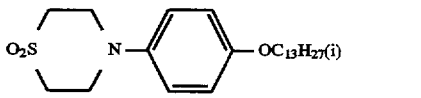
(ST-11)

-continued
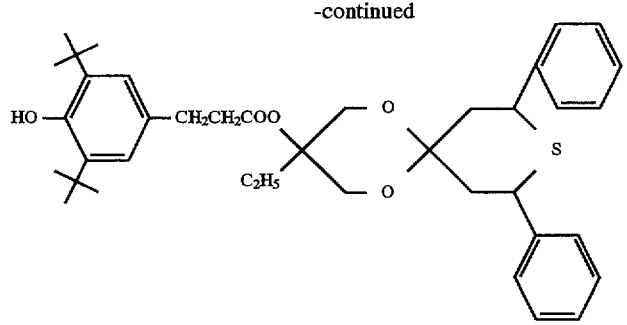 (ST-12)
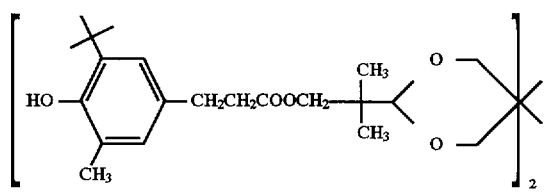 (ST-13)
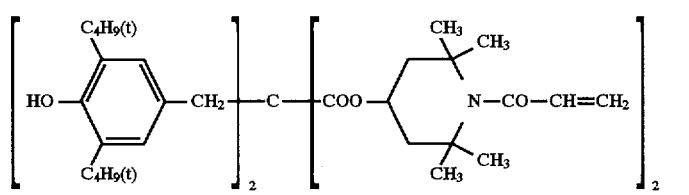 (ST-14)
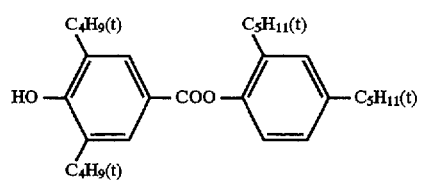 (ST-15)
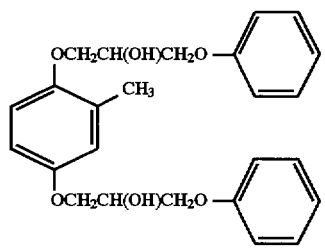 (ST-16)
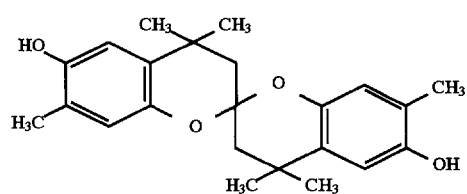 (ST-17)
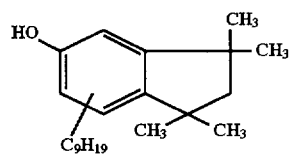 (ST-18)
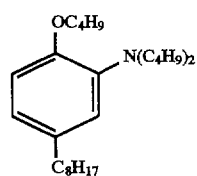 (ST-19)

and the compounds mentioned as EOP scavengers.

The layers of the photographic material can be cured using conventional curing agents. Examples of suitable curing agents are formaldehyde, glutaraldehyde and similar aldehyde compounds, diacetyl, cyclopentadione and similar ketone compounds, bis(2-chloroethylurea), 2-hydroxy-4,6-dichloro-1,3,5-triazine and similar compounds containing reactive halogen (U.S. Pat. No. 3,288,775, U.S. Pat. No. 2,732,303, GB-A-974 723 and GB-A-1 167 207), divinyl sulfone compounds, 5-acetyl-1,3-diacryloylhexahydro-1,3,5-triazine and other compounds containing a reactive olefin bond (U.S. Pat. No. 3,635,718, U.S. Pat. No. 3,232,763 and GB-A-994 869); N-hydroxymethylphthalimide and other N-methylol compounds (U.S. Pat. No. 2,732,316 and U.S. Pat. No. 2,586,168); isocyanates (U.S. Pat. No. 3,103,437); aziridine compounds (U.S. Pat. No. 3,017,280 and U.S. Pat. No. 2,983,611); acid derivatives (U.S. Pat. No. 2,725,294 and U.S. Pat. No. 2,725,295); compounds of the carbodiimide type (U.S. Pat. No. 3,100,704); carbamoylpyridinium salts (DE-A-2 225 230 and U.S. Pat. No. 2,439,511); carbamoylpyridinium compounds (DE-A-2 408 814); compounds containing a phosphorus-halogen bond (JP-A-113 929/83); N-carbonyloximide compounds (JP-A-43 353/81); N-sulfonyloximido compound (U.S. Pat. No. 4,111,926), dihydroquinoline compounds (U.S. Pat. No. 4,013,468), 2-sulfonyloxypyridinium salts (JP-A-110 762/81 ), formamidinium salts (EP-A-0 162 308), compounds containing two or more N-acyloximino groups (U.S. Pat. No. 4,052,373), epoxy compounds (U.S. Pat. No. 3,091,537), compounds of the isoxazole type (U.S. Pat. No. 3,321,313 and U.S. Pat. No. 3,543,292); halocarboxaldehydes, such as mucochloric acid; dioxane derivatives, such as dihydroxydioxane and dichlorodioxane; and inorganic curing agents, such as chromiumalum and zirconium sulfate.

The curing can be accomplished in a known manner by adding the curing agent to the casting solution for the layer to be cured or by coating the layer to be cured with a layer comprising a diffusable curing agent.

The classes mentioned include slow-acting and fast-acting curing agents and so-called instant curing agents, which are particularly advantageous. The term "instant curing agents" is taken to mean compounds which crosslink suitable binders in such a way that, immediately after casting, at the latest after 24 hours, preferably at the latest after 8 hours, the curing is complete to such an extent that no further change in sensitometry caused by the crosslinking reaction or swelling of the layer system occurs. The term "swelling" is taken to mean the difference between the wet-layer thickness and the dry-layer thickness in the case of aqueous processing of the film (Photogr. Sci., Eng. 8 (1964), 275; Photogr. Sci., Eng. (1972), 449).

These curing agents which react very quickly with gelatin are, for example, carbamoylpyridinium salts which are capable of reacting with free carboxyl groups of the gelatin so that the latter react with free amino groups of the gelatin to form peptide bonds and crosslinking of the gelatin.

Suitable examples of instant curing agents are compounds of the formula $$\begin{array}{c} R_1 \\ \diagdown \\ N-CO-\overset{\oplus}{N}\diagup\!\!\!\diagup Z \quad X^{\ominus} \\ \diagup \quad \quad \quad | \\ R_2 \quad \quad \quad R_3 \end{array} \quad \text{(a)}$$

in which $R_1$ is alkyl, aryl or aralkyl, $R_2$ is as defined for $R_1$ or is alkylene, arylene, aralkylene or alkarylene, where the second bond is linked to a group of the formula, $$\begin{array}{c} R_1 \\ | \\ -N-CO-\overset{\oplus}{N}\diagup\!\!\!\diagup Z \quad X^{\ominus} \\ \quad \quad \quad | \\ \quad \quad \quad R_3 \end{array}$$

or $R_1$ and $R_2$ together are the atoms necessary to complete a substituted or unsubstituted heterocyclic ring, for example a piperidine, piperazine or morpholine ring, where the ring may be substituted, for example, by example, by $C_1$–$C_3$alkyl or halogen, $R_3$ is hydrogen, alkyl, aryl, alkoxy, —$NR_4$—$COR_5$, —$(CH_2)_m$—$NR_8R_9$, —$(CH_2)_n$—$CONR_{13}R_{14}$ or $$-(CH_2)_p-\underset{\underset{R_{15}}{|}}{CH}-Y-R_{16}$$

or a bridge or a direct bond to a polymer chain, where $R_4$, $R_6$, $R_7$, $R_9$, $R_{14}$, $R_{15}$, $R_{17}$, $R_{18}$, and $R_{19}$ are hydrogen or $C_1$–$C_4$alkyl, $R_5$ is hydrogen, $C_1$–$C_4$alkyl or $NR_6R_7$, $R_8$ is —$COR_{10}$ $R_{10}$ is $NR_{11}R_{12}$ $R_{11}$ os $C_1$–$C_4$alkyl or aryl, in particular phenyl, $R_{12}$ is hydrogen, $C_1$–$C_4$alkyl or aryl, in particular phenyl $R_{13}$ is hydrogen, $C_1$–$C_4$alkyl or aryl, in particular phenyl, $R_{16}$ is hydrogen, $C_1$–$C_4$alkyl, —$COR_{18}$ or $CONHR_{19}$, m is a number from 1 to 3 n is a number from 0 to 3 p is a number from 2 to 3,

Y is O or $NR_{17}$, or $R_{13}$ and $R_{14}$ together are the atoms necessary to complete a substituted or unsubstituted heterocyclic ring, for example a piperidine, piperazine or morpholine ring, where the ring may be substituted, for example, by $C_1$–$C_3$alkyl or halogen, Z is the atoms necessary to complete a 5- or 6-membered aromatic heterocyclic ring, with or without a fused benzene ring, and $X^{\ominus}$ is an anion, which is absent if an anionic group is already linked to the remainder of the molecule;

$$\begin{array}{c} R_1 \quad \quad O \quad \quad \quad \quad R_3 \\ \diagdown \quad \quad \| \quad \quad \diagup\!\!\!\diagup \\ N-C-O-\overset{\oplus}{N} \quad \quad \quad X^{\ominus} \\ \diagup \quad \quad \quad \quad \diagdown\!\!\!\diagdown \\ R_2 \end{array} \quad \text{(b)}$$

in which $R_1$, $R_2$, $R_3$ and $X^{\ominus}$ are as defined for the formula (a).

There are diffusable curing agents which have a curing action in the same manner on all layers within a layer system. However, there are also non-diffusing, low-molecular weight and high-molecular weight curing agents whose action is restricted to certain layers. They can be used to effect particularly strong crosslinking of individual layers, for example the protective layer. This is important if the silver-halide layer cures to a low extent owing to the increase in silver covering power and the mechanical properties must be improved with the protective layer (EP-A-0 114 699).

Colour-photographic negative materials are usually processed by development, bleaching, fixing and washing or by development, bleaching, fixing and stabilization without subsequent washing, it being possible for bleaching and fixing to be combined in a single processing step. The colour developer compound can be any developer compound which is capable of reacting, in the form of its oxidation product, with colour couplers to form azomethine or indophenol dyes. Suitable colour developers are aromatic compounds of the p-phenylenediamine type containing at least one primary amino group, for example N,N-dialkyl-p-phenylenediamine, such as N,N-diethyl-p-phenylenediamine, 1-(N-ethyl-N-methanesulfonamidoethyl)-3-methyl-p-phenylenediamine and 1-(N-ethyl-N-methoxyethyl)-3-methyl-p-phenylenediamine. Other colour developers which can be used are described, for example, in J. Amer. Chem. Soc. 73, 3106 (1951) and G. Haist, Modern Photographic Processing, 1979, John Wiley & Sons, New York 545 ff.

The colour development can be followed by an acidic stop bath or washing.

The material is usually bleached and fixed immediately after colour development. Examples of bleaches which can be used are Fe(III) salts and Fe(III) complex salts such as ferricyanides, dichromates and water-soluble cobalt complexes. Particular preference is given to iron(III) complexes of aminopolycarboxylic acids, in particular, for example, of ethylenediaminetetraacetic acid, propylenediaminetetraacetic acid, diethylenetriaminepentaacetic acid, nitrilotriacetic acid, iminodiacetic acid, N-hydroxyethylethylenediaminetriacetic acid, alkyliminodicarboxylic acids and of corresponding phosphonic acids. Other suitable bleaches are persulfates and peroxides, for example hydrogen peroxide.

The bleaching/fixing bath or fixing bath is usually followed by washing, either in countercurrent or in a plurality of tanks with their own water supply.

Favourable results can be obtained if a subsequent final bath is used which contains no or only little formaldehyde.

However, the washing can also be replaced in its entirety by a stabilizing bath, which is usually carried out in countercurrent. If formaldehyde is added, this stabilizing bath also takes on the function of a final bath.

In colour reversal materials, the first step is development with a black/white developer whose oxidation product is not capable of reacting with the colour couplers. This is followed by diffuse second exposure and then development with a colour developer, bleaching and fixing.‖

The present invention therefore also relates to a process for stabilizing photographic recording material comprising, on a base, at least one silver-halide emulsion layer and, if desired, at least one interlayer and/or protection layer, wherein a UV absorber of the formula (I) is added to at least one of said layers.

The present invention furthermore relates to the use of compounds of the formula (I) for stabilizing photographic recording material comprising, on a base, at least one silver-halide emulsion layer and, if desired, at least one interlayer and/or protection layer.

The preferences described in greater detail above under the novel photographic recording material also apply correspondingly to the novel process, the novel use and the novel compounds of the formula (I).

The examples below describe the subject-matter of the invention in greater detail without representing a limitation. In the examples, parts and percentages are by weight; if an example mentions room temperature, this is taken to mean a temperature in the range 20°–25° C. These definitions apply in each case unless otherwise stated. Wherever possible, compound numbers relate to the list of novel compounds given above. Alkyl radicals denoted by -n are straight-chain; i- denotes isomer mixtures.

The following abbreviations are used:

| THF | tetrahydrofuran |
| --- | --- |
| abs. | anhydrous |
| m.p. | melting point or melting range |
| $T_g$ | glass transition temperature |
| b.p. | boiling point |
| NMR | nuclear magnetic resonance |
| liq. | liquid |
| mmHg | torr (1 torr = 133,322 Pa) |
| DSC | differential scanning calorimetry |
| ε | absorbance coefficient (ethyl acetate); the index denotes the wavelength |

A) Preparation Examples

EXAMPLE A1

2-mesityl-4,6-dichloro-1,3,5-triazine

A solution of 109.5 g (0.55 mol) of 2-bromomesitylene (purity 98%) in 150 ml of abs. THF (purity 99.5%) is added over the course of 1½ hours under nitrogen to a stirred suspension held at 60° C. of 14.6 g (0.60 mol) of magnesium turnings (purity 99.8%) in 100 ml of abs. THF to which an iodine crystal has been added. The mixture is subsequently kept at the reflux temperature (68° C.) for 30 minutes.

After cooling, the resultant Grignard reagent is transferred into a dropping funnel and added dropwise to a solution of 96.0 g (0.52 mol) of cyanuric chloride (98%) in 270 ml of THF. During the addition, which takes 1½ hours, the temperature is kept at between 15° and 30° C. by cooling. The mixture is subsequently stirred at 25° C. for 2 hours, then poured into 2 l of an ice/water mixture containing 80 ml of 32% HCl (0.81 mol). The mixture is stirred for one hour and filtered. The filter cake is suspended in 1000 ml of water, stirred for 30 minutes and re-filtered. This operation is repeated twice. The filter cake is dried over $P_2O_5$ for 24 hours at 25° C. and a pressure of 60 mmHg (8000 Pa). 171.0 g of crude product are subsequently dissolved in toluene, filtered while hot and crystallized by addition of hexane and cooling to 0° C. Filtering-off and drying give 82.8 g of the title product (compound 1a)

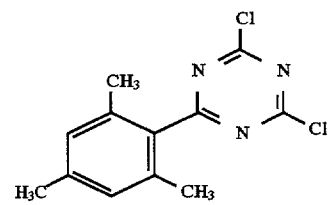

Compound 1a of m.p. 85°–91° C.

$^1$H-NMR (CDCl$_3$, 300 MHz): δ 2.22 (s, 6H); 2.32 (s, 3H); 6.95 (s, 2H).

EXAMPLE A2

2-mesityl-4,6-bis(2,4-dihydroxyphenyl)-1,3,5-triazine 148.7 g (1.21 mol) of anhydrous aluminium trichloride (purity 98%) are added with stirring to a suspension of 130.0 g (0.485 mol) of 2-mesityl-4,6-dichloro-1,3,5-triazine (compound 1a) in 300 ml of petroleum ether (boiling range 110°–140° C.) and 385 ml of sulfolane. During this addition, the mixture warms to 45° C. A solution of 133.5 g (1.21 mol) of resorcinol (purity 98%) in 155 ml of sulfolane is added over the course of 45 minutes. The mixture is warmed at 80°–85° C. for 5 hours 30 minutes with evolution of HCl. The upper phase (petroleum ether) is removed, and the lower, viscous phase is transferred while hot into a stirred mixture of 2.1 l of methanol and 2.1 l of water. After the mixture has been stirred for 14 hours, the solid is filtered off, stirred for 1 hour in 2.2 l of 1 molar HCl and filtered off again. The filter cake is suspended in 1000 ml of water, stirred for 30 minutes and re-filtered. This operation is repeated twice. The filter cake is dried for 24 hours at 80° C. and a pressure of 60 mmHg (8000 Pa), giving 170.5 g of the title product (compound 1b) of the formula

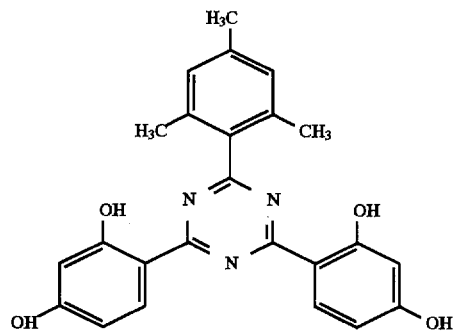

of m.p. 230°–234° C.

EXAMPLE A3

2-mesityl-4,6-bis(2-hydroxy-4-[3-n-butoxy-2-hydroxypropoxy]phenyl)-1,3,5-triazine A mixture of 20.0 g (0.048 mol) of 2-mesityl-4,6-bis(2,4-dihydroxyphenyl)-1,3,5-triazine (compound 1b), 13.8 g (0.105 mol) of n-butyl glycidyl ether (purity 95%) and 1.8 g (4.8 mmol) of ethyltriphenylphosphonium bromide (purity 97%) in 100 ml of mesitylene (purity 99%) is stirred at 140° C. under nitrogen for 21 hours. Decantation and evaporation of the remaining solvent gives 41.2 g of crude product. This is dissolved in 100 ml of ethyl acetate and filtered through a 10.5 cm layer of silica gel 60 (230–400 mesh) of diameter 7.5 cm, with elution with 3 l of ethyl acetate/hexane (1:1 mixture). The 34.0 g of solid obtained after removal of the solvent are re-dissolved in 25 ml of ethyl acetate. 250 ml of hexane are added to the viscous solution. The mixture is stirred at 0° C. for 2 hours and filtered, and the solid is dried for 24 hours at 80° C. and a pressure of 60 mmHg (8000 Pa), giving 23.0 g of the title product (compound 2) of the formula

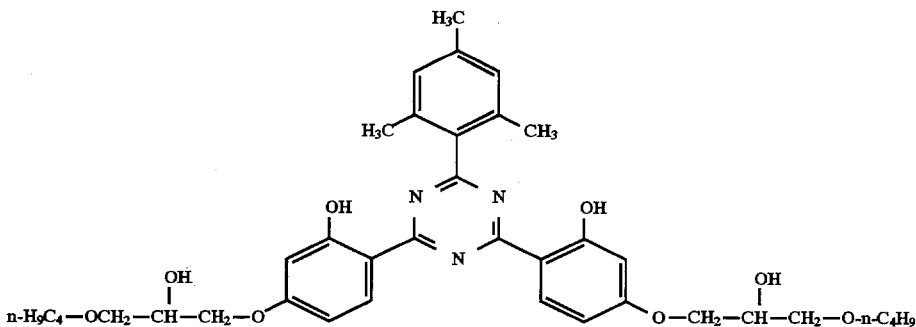

of m.p. 125°–131° C.

EXAMPLE A4

2-mesityl-4,6-bis(2-hydroxy-4-[3-(2-ethylhexyloxy)-2-hydroxypropoxy]-phenyl)-1,3,5-triazine A mixture of 39.5 g (0.095 mol) of 2-mesityl-4,6-bis(2,4-dihydroxyphenyl)-1,3,5-triazine (compound 1b), 40.7 g (0.2185 mol) of 2-ethylhexyl glycidyl ether (purity 98%) and 3.5 g (9.5 mmol) of ethyltriphenylphosphonium bromide (purity 97%) in 250 ml of mesitylene (purity 99%) is stirred at 140° C. under nitrogen for 16 hours. The clear solution is freed from solvent under reduced pressure. The crude product is dissolved in 200 ml of ethyl acetate and filtered through a 6.0 cm layer of silica gel 60 (230–400 mesh) of diameter 8.0 cm, with elution with 1000 ml of ethyl acetate. Removal of the solvent and drying for 2 hours at 100° C. and a pressure of 0.6 mmHg (80 Pa) give 61.3 g (yield 81.8%) of the title product (compound 7; Tg 54.4° C.) of the formula

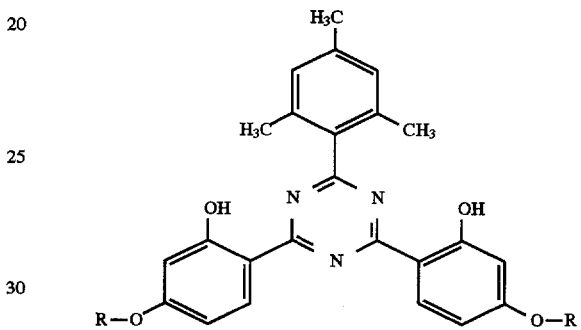

where R=CH$_2$—CH(OH)—CH$_2$O—CH$_2$—CH(C$_2$H$_5$)—CH$_2$CH$_2$CH$_2$CH$_3$.

UV maxima (ethyl acetate): ε (299 nm)=32780; ε (352 nm)=41690.

EXAMPLE A5

2-mesityl-4,6-bis(2-hydroxy-4-[3-(iso*-dodecyloxy)-2-hydroxypropoxy]-phenyl)-1,3,5-triazine In the compound name, iso*-dodecyloxy represents a mixture of various dodecyl substituents (i-C$_{12}$H$_{25}$).

A mixture of 29.9 g (0.072 mol) of 2-mesityl-4,6-bis(2,4-dihydroxyphenyl)-1,3,5-triazine (compound 1b), 40.1 g (0.166 mol) of dodecyl glycidyl ether (isomer mixture, obtainable as HAGE®-12, Shell) and 2.7 g (7.2 mmol) of ethyltriphenylphosphonium bromide (purity 97%) in 200 ml of mesitylene (purity 99%) is stirred at 140° C. under nitrogen for 15 hours. The clear brown solution is freed from solvent under reduced pressure. The crude product is dissolved in 200 ml of ethyl acetate and filtered through a 6.0 cm layer of silica gel 60 (230–400 mesh) of diameter 8.0 cm, with elution with 500 ml of ethyl acetate. Removal of the solvent and drying for 2 hours at 140° C. and a pressure of 0.9 mmHg (120 Pa) give 60.2 g (yield: 92.9%) of the title product (compound 8; $T_g$ 0.8° C.) of formula

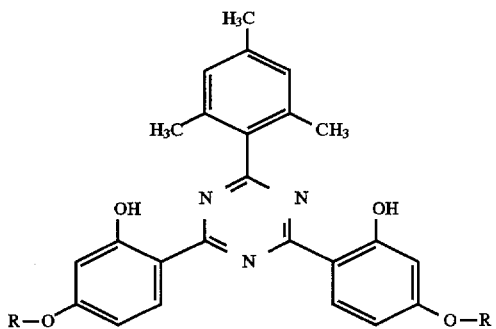

where R=CH$_2$—CH(OH)—CH$_2$O-i-C$_{12}$H$_{25}$.

UV maxima (ethyl acetate): ε (298 nm)=30790; ε (351.5 nm)=39520.

The following compounds of the general formulae shown are obtained by the same method, but replacing dodecyl glycidyl ether by the reagents shown in Table A5 below. The temperatures shown in the final column indicate the melting points, unless otherwise stated; temperatures followed by * are glass transition temperatures.

A mixture of 25.0 g (60 mmol) of 2-mesityl-4,6-(2,4-dihydroxyphenyl)-1,3,5-triazine, 18.2 g (132 mmol) of K$_2$CO$_3$ (Fluka, 99%), 200 ml of diethylene glycol dimethyl ether (Fluka, 99.5%) and 24.8 g (150 mmol) of 1-bromohexane is kept at 115° C. for 17 hours with stirring. The mixture is filtered while hot, and the solvent is removed (rotary evaporator). Recrystallization from 100 ml of ethylene glycol monoethyl ether and drying for 24 hours at 60° C./60 mmHg give 20.7 g (58.9%) of 2-mesityl-4,6-bis-(2-hydroxy-4-n-hexyloxyphenyl)-1,3,5-triazine (compound 9), m.p. 140°–142° C.

Compound (10) is obtained as an orange resin by the same method using 1-bromo-1-ethylhexane instead of 1-bromohexane; $T_g$ 8.1° C.

EXAMPLE A7

(i) Preparation of a 1-bromooctane isomer mixture 75.0 g (0.75 mol) of sulfuric acid (98%) are added dropwise, with stirring and cooling in an ice bath, to a solution of 195.3 g (1.50 mol) of isooctanol (obtainable from Exxon under the name Exxal® 8N). 379.2 g (256.2 ml) of 48% aqueous HBr (2.25 mol) are subsequently added dropwise. The mixture is heated at 113° C. for 5 hours and then cooled, and the organic (upper) phase is separated off and diluted with 250 ml of ethyl acetate. The solution is washed successively 1× with 250 ml of water,
2× with 250 ml of 10% aqueous NaHCO$_3$ and
2× with 250 ml of saturated aqueous sodium chloride solution.

TABLE A5

Preparation of compounds 1, 3, 4, 4a, 5, 6, 8d, 8x, 12, 17 and 20a-d

| Comp. No. | R | Reagent | Charact. |
|---|---|---|---|
| (1) | CH$_2$CH(OH)CH$_2$OC$_2$H$_5$ | Ethyl glycidyl ether | 49° C.* |
| (3) | CH$_2$CH(OH)CH$_2$OC(CH$_3$)$_3$ | Isopropyl glycidyl ether | 54.9° C.* |
| (4) | CH$_2$CH(OH)CH$_2$OCH$_2$CH(CH$_3$)CH$_3$ | Isobutyl glycidyl ether | 147–152° C. |
| (4a) | CH$_2$CH(OH)CH$_2$OCH(CH$_3$)C$_2$H$_5$ | sec-Butyl glycidyl ether | 28.2° C.* |
| (5) | CH$_2$CH(OH)CH$_2$O—(CH(CH$_3$)—C$_2$H$_5$/CH(CH$_3$)—C$_3$H$_7$-n) | 1:1 mixture of sec-butyl and sec-pentyl glycidyl ether | 22.3° C.* |
| (6) | CH$_2$CH(OH)CH$_2$O—C$_6$H$_{13}$-n | n-Hexyl glycidyl ether | 50.6° C.* |
| (8d) | CH$_2$CH(OH)CH$_2$O—C$_6$H$_5$ | Phenyl glycidyl ether | 56.4° C.* |
| (8x) | CH$_2$CH(OH)CH$_2$O—(—C$_{12}$H$_{25}$/—C$_{13}$H$_{27}$) | 1:1 (w/w) mixture of various dodecyl and tridecyl glycidyl ethers (HAGE 12 [Shell]; EUREPOX RV-G [Witco] | ε$_{353}$ = 40230** |
| (12) | CH$_2$CH(OH)CH$_2$O—(CH$_2$—CH$_2$—O—)$_{7-8}$—CH$_3$ | Polyethyleneoxymethyl glycidyl ether, principal component 7-8 ethylene oxide units (350 g/mol) | ε$_{353}$ = 40480** |
| (17) | CH$_2$CH(OH)CH$_2$O—CH$_2$CH=CH$_2$ | Allyl glycidyl ether | 122–127° C. |
| (20a) | CH$_2$CH(OH)—C$_4$H$_9$-n | 1,2-Epoxyhexane | 160–164° C. |
| (20b) | CH$_2$CH(OH)—(CH$_2$)$_2$CH=CH$_2$ | 1,2-Epoxyhex-5-ene | 124–129° C. |
| (20c) | CH$_2$CH(OH)—(CH$_2$)$_6$CH=CH$_2$ | 1,2-Epoxydec-9-ene | 39.2° C.* |
| (20d) | [cyclohexane with HO] | Epoxycyclohexane | 35.3° C.* |

**UV data: solvent ethyl acetate.

EXAMPLE A6

2-Mesityl-4,6-bis(2-hydroxy-4-n-hexyloxyphenyl)-1,3,5-triazine

After drying (MgSO$_4$) and removal of the solvent, the product is distilled over a Vigreux column, giving 214.10 g (73.9%) of a mixture of various bromooctane isomers as a colourless liquid, b.p. 66°–69° C. (16 mmHg).

(ii) 2-Mesityl-4,6-bis(2-hydroxy-4-i-octyloxyphenyl)-1,3,5-triazine

A mixture of 20.0 g (48.0 mmol) of 2-mesityl-4,6-(2,4-dihydroxyphenyl)-1,3,5-triazine, 13.3 g (96.0 mmol) of $K_2CO_3$ (Fluka, 99%), 0.5 g.(3 mmol) of KI (Merck, 99.5%), 90 ml of diethylene glycol dimethyl ether (Fluka, 99.5%) and 24.8 g (150 mmol) of 1-bromooctane isomer mixture (i) is heated at 120° C. for 23 hours with stirring. The mixture is filtered while hot, and the solvent is removed (rotary evaporator). The crude product is dissolved in 60 ml of toluene and filtered through an 8 cm layer of silica gel 60 (230–400 mesh) of diameter 10 cm with elution with 1000 ml of toluene. Removal of the solvent and drying at 130° C./0.1 mmHg for 4 hours give 23.8 g (77.5%) of 2-mesityl-4,6-bis(2-hydroxy-4-iso-octyloxyphenyl)-1,3,5-triazine (compound 11) as a yellow resin; $T_g$ 122.9° C.

EXAMPLE A8

2-mesityl-4,6-bis(2-hydroxy-4-[1-(ethoxycarbonyl)ethoxy]phenyl)-1,3,5-triazine

A mixture of 24.9 g (60.0 mmol) of 2-mesityl-4,6-(2,4-dihydroxyphenyl)-1,3,5-triazine, 16.6 g (96.0 mmol) of $K_2CO_3$ (Fluka, 99%), 0.5 g (3 mmol) of potassium iodide (Merck, 99.5%), 90 ml of diethylene glycol dimethyl ether (Fluka, 99.5%) and 23.9 g (132.0 mmol) of ethyl α-bromopropionate (Fluka, 98%) is heated at 110° C. for 17 hours with stirring. The mixture is filtered while hot, and the solvent is removed (rotary evaporator). The crude product is dissolved in 100 ml of ethyl acetate and filtered through a 4.5 cm layer of silica gel 60 (230–400 mesh) of diameter 6.5 cm, with elution with 200 ml of ethyl acetate. Removal of the solvent, drying at 100° C./0.1 mmHg for 2 hours, powdering of the solid and further drying for 14 hours at 80° C./60 mmHg give 32.8 g (88.8%) of 2-mesityl-4,6-bis(2-hydroxy-4-[1-(ethoxycarbonyl)ethoxy]phenyl)-1,3,5-triazine (compound 13), m.p. 142°–147° C.

The following compounds of the general formula

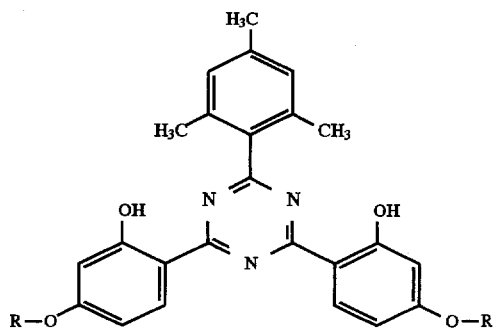

are obtained by the method described under A8, with the ethyl α-bromopropionate being replaced by the reagents shown in Table A8 below. The temperatures in the final column denote the melting points, unless otherwise stated; temperatures followed by * are glass transition temperatures; i-octyl denotes an octyl isomer mixture. UV data: solvent ethyl acetate.

TABLE A8

Preparation of compounds 14, 15 and 15a–c

| Comp. No. | R | Reagent | Charact. |
|---|---|---|---|
| (14) | $CH(C_4H_9-n)$—CO—$OC_2$—$H_5$ | Ethyl α-bromohexanoate | $\epsilon_{351}$ = 39590 |
| (15) | —$(CH_2)_5$—CO—O—$C_2H_5$ | 1-Bromo-5-ethoxy-carbonyl-pentane | |
| (15a) | $CH(C_2H_5)$—CO—$OC_2H_5$ | Ethyl α-bromobutanoate | 50.3° C.* |
| (15b) | $CH(CH_3)_2$—CO—$OC_2H_5$ | Ethyl α-bromo-α-methylpropionate | 50.4° C.* |
| (15c) | $CH(C_2H_5)$—CO—$OC_8H_{17}$ | i-Octyl α-bromobutanoate | $\epsilon_{351}$ = 40360 |

EXAMPLE A9

2-mesityl-4,6-bis[2-hydroxy-4-((3-n-butoxy-2-acetoxy)propoxy)phenyl]-1,3,5-triazine A mixture of 25.0 g (37.0 mmol) of 2-mesityl-4,6-bis[2-hydroxy-4-(3-n-butoxy-2-hydroxypropoxy)phenyl]-1,3,5-triazine (compound 2), 8.7 g (110 mmol) of acetyl chloride (Fluka, 99%) and 0.4 g (5 mmol) of pyridine (Fluka, 99%) in 120 ml of toluene (Fluka, 99.5%) is heated at 55° C. for 14 hours with stirring. The solvent is removed (rotary evaporator). The crude product is dissolved in 50 ml of methylene chloride and filtered through a 5 cm layer of silica gel 60 (230–400 mesh) of diameter 6 cm, with elution with 500 ml of methylene chloride. Removal of the solvent and drying at 80° C./0.2 mmHg for 2 hours give 25.1 g (89.3%) of 2-mesityl-4,6-bis-[2-hydroxy-4-((3-n-butoxy-2-acetoxy)propoxy)phenyl]-1,3,5-triazine (compound 16), as a yellow resin.

$^1$H-NMR (300 MHz, $CDCl_3$): the spectrum is consistent with the desired product. UV maxima (ethyl acetate): ε (298 nm)=35490; ε (351 nm) =41410.

EXAMPLE A10

Starting compounds for compounds (21)–(22a)

(i) Use of 2,6-dimethylbromobenzene instead of 2-bromomesitylene in the process described in Example A1 gives the compound of the formula

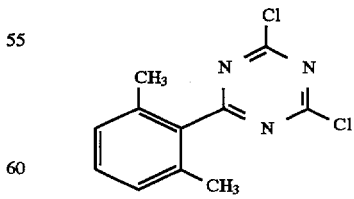

as a slow-crystallizing resin; m.p. 70°–83° C.

(ii) Use of the above compound A10(i) instead of compound 1a in the process described in Example A2 gives the compound of the formula

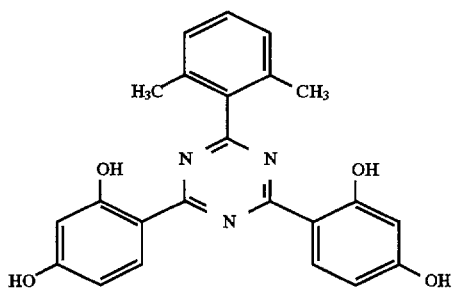

m.p. 161.5°–164.5° C.

EXAMPLE A11

Starting compounds for compounds (23) and (24)

(i) Use of 2,3,5,6-tetramethylbromobenzene instead of 2-bromomesitylene in the process described in Example A1 gives the compound of the formula

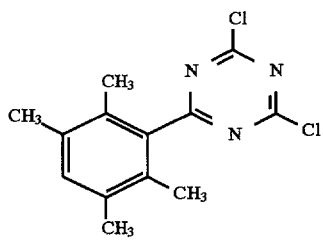

m.p. 210°–213° C.

(ii) Use of the above compound A11(i) instead of compound 1a in the process described in Example A2 gives the compound of the formula

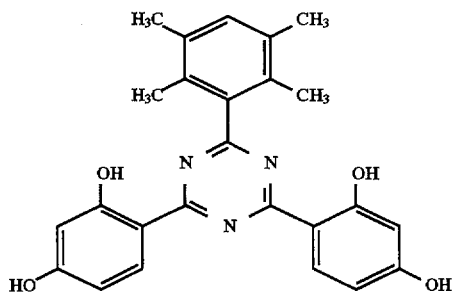

as a pale yellow solid; m.p. 300°–307° C.

EXAMPLE A12

Starting compounds for compounds (25) and (26)

(i) Use of 2,3,4,6-tetramethylbromobenzene instead of 2-bromomesitylene in the process described in Example A1 gives the compound of the formula

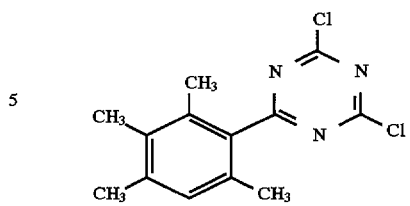

as a white solid; m.p. 103.5°–105° C.

(ii) Use of the above compound A12(i) instead of compound 1a in the process described in Example A2 gives the compound of the formula

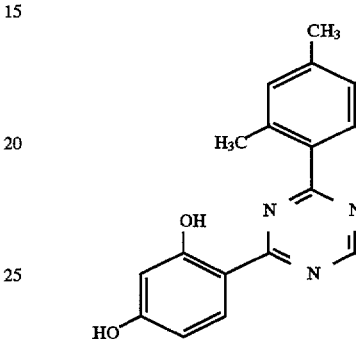

as a yellow solid; m.p. 279°–290° C.

EXAMPLE A13

Starting compounds for compounds (27) and (28)

(i) Use of 2,3,4,5,6-pentamethylbromobenzene instead of 2-bromomesitylene in the process described in Example A1 gives the compound of the formula

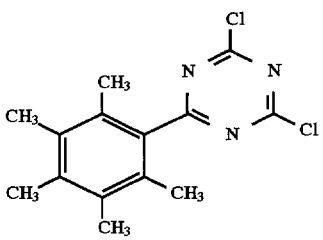

as a white solid; m.p. 177°–178° C.

(ii) Use of the above compound A13(i) instead of compound 1a in the process described in Example A2 gives the compound of the formula

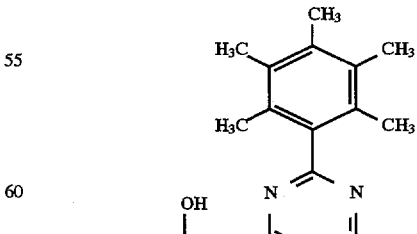

as a yellow solid; m.p. 258°–283° C.

EXAMPLE A14

Starting compounds for compounds (29) and (30)

(i) Use of 2,6-dimethyl-4-tert-butylbromobenzene instead of 2-bromomesitylene in the process described in Example A1 gives the compound of the formula

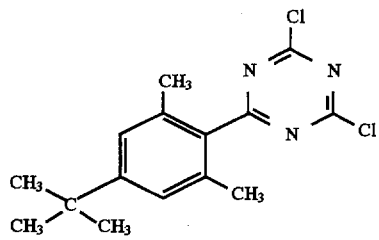

m.p. 149°–150.5° C.

(ii) Use of the above compound A14(i) instead of compound 1a in the process described in Example A2 gives the compound of the formula

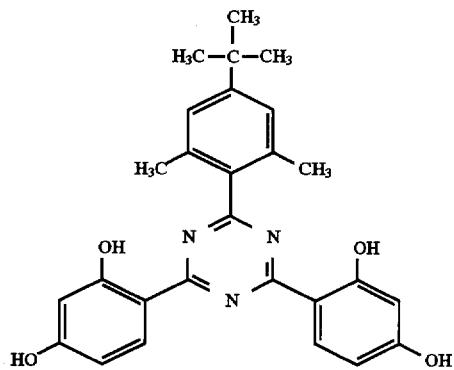

m.p. 291°–300° C.

EXAMPLE A15

Starting compounds for compounds (31) and (32)

(i) Use of 2,6-dimethyl-4-methoxybromobenzene instead of 2-bromomesitylene in the process described in Example A1 gives the compound of the formula

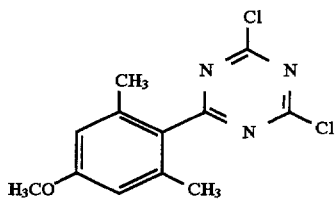

m.p. 111°–114° C.

(ii) Use of the above compound A15(i) instead of compound 1a in the process described in Example A2 gives the compound of the formula

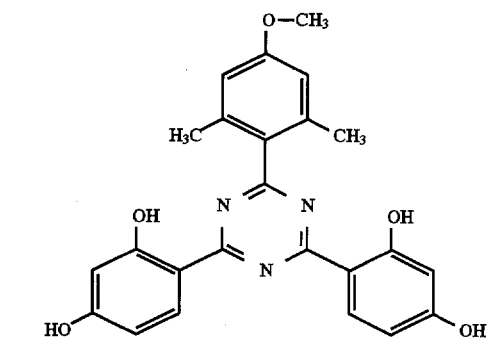

as a yellow solid; m.p. 292°–298° C.

EXAMPLE A16

Starting compounds for compounds (33) and (34)

(i) Use of 2,4,6-triisopropylbromobenzene instead of 2-bromomesitylene in the process described in Example A1 gives the compound of the formula

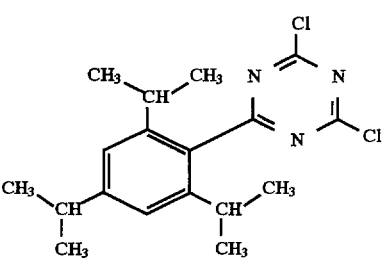

as a pale yellow solid; m.p. 95°–101° C.

(ii) Use of the above compound A16(i) instead of compound 1a in the process described in Example A2 gives the compound of the formula

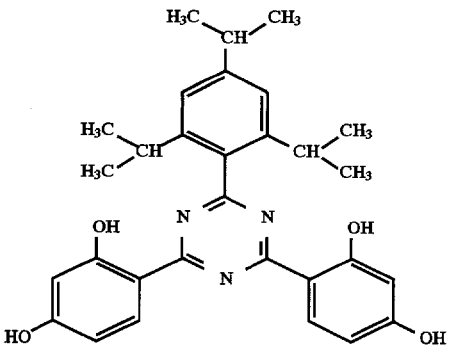

Decomposition point: 307°–315° C.

EXAMPLE A17

Starting compounds for compounds (35) and (36)

(i) Use of 2,6-dimethyl-4-chlorobromobenzene instead of 2-bromomesitylene in the process described in Example A1 gives the compound of the formula

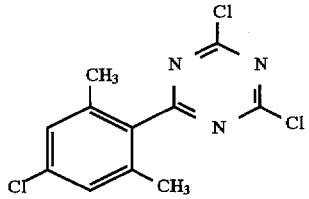

(ii) Use of the above compound A17(i) instead of compound 1a in the process described in Example A2 gives the compound of the formula

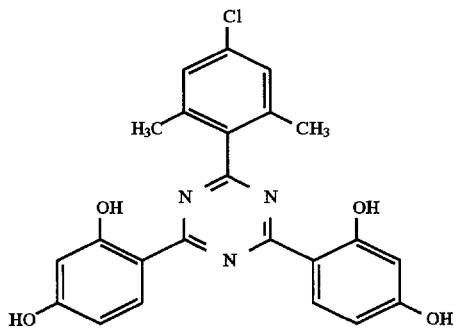

EXAMPLE A18

Shafting compounds for compound (37)

(i) Use of 2,4,6-trimethyl-3-methoxybromobenzene instead of 2-bromomesitylene in the process described in Example A1 gives the compound of the formula

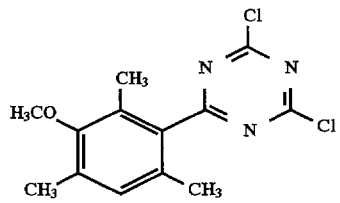

m.p. 103°–105° C.

(ii) Use of the above compound A18(i) instead of compound 1a in the process described in Example A2 gives the compound of the formula

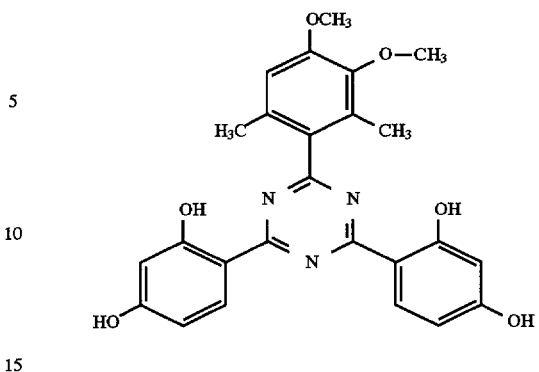

as a yellow solid; m.p. 268°–276° C.

EXAMPLE A19

The compounds shown in the table below are prepared by the method described in Example A3.

TABLE A19

Preparation of compounds (21), (23), (25), (27), (29), (31), (33), (35), (37)

| Comp. No. | Starting material from Example | Characterization |
| --- | --- | --- |
| 21 | A10 | Melting range 110–122° C. |
| 23 | A11 | Melting range 112–123° C. |
| 25 | A12 | UV (ethyl acetate) $\epsilon_{352}$ = 40360 |
| 27 | A13 | Melting range 127–145° C. (DSC) |
| 29 | A14 | UV (ethyl acetate) $\epsilon_{351}$ = 38700 |
| 31 | A15 | UV (ethyl acetate) $\epsilon_{350.5}$ = 43240 |
| 33 | A16 | UV (ethyl acetate) $\epsilon_{353}$ = 39200 |
| 35 | A17 | |
| 37 | A18 | Yellow resin; $T_g$ 18.4° C. |

EXAMPLE 20

Compounds (22), (22a), (24), (26), (28), (30), (32), (34) and (36) are prepared as shown in Table A20.

TABLE A20

| Comp. No. | Process of Example | Starting compounds | Characterization |
| --- | --- | --- | --- |
| 22 | A7(ii) | A10(ii), A7(i) | $T_g$ 118.2° C. |
| 22a | A6 | A10(ii), 1-Bromohexane | m.p. 135–137° C. |
| 24 | A8 | A11(ii), 1-Bromo-ethoxy-carbonyldecane | m.p. 78.5° C. (DSC) |
| 26 | A5 | A12(ii), 1,2-Epoxyoctane | m.p. 132.7° C. (DSC) |
| 28 | A5 | A13(ii), i-Dodecyl glycidyl ether | Tg. 3.2° C. (DSC) |
| 30 | A5 | A14(ii), Phenyl glycidyl ether | m.p. 167.0° C. (DSC) |
| 32 | A5 | A15(ii), Allyl glycidyl ether | $T_g$ 49° C. |
| 34 | A5 | A16(ii), Epoxycyclohexane | m.p. 247–251° C. |
| 36 | A6 | A17(ii), 1-Bromohexane | |

B) Use Examples

EXAMPLE B1

Stabilization of a 2-layer metallic finish

The compound to be tested is incorporated into 5–10 g of xylene and tested in a varnish having the following composition:

| | |
|---|---:|
| Synthacryl® SC 303[1] | 27.51 |
| Synthacryl® SC 370[2] | 23.34 |
| Maprenal® MF 650[3] | 27.29 |
| Butyl acetate/butanol (37/8) | 4.33 |
| Isobutanol | 4.87 |
| Solvesso® 150[4] | 2.72 |
| Crystal Oil K-30[5] | 8.74 |
| Baysilon® MA flow-control agent[6] | 1.20 |
| | 100.00g |

[1] Acrylate resin, Hoechst AG; 65% solution in xylene/butanol 26:9
[2] Acrylate resin, Hoechst AG; 75% solution in Solvesso® 100[4]
[3] Melamine resin, Hoechst AG; 55% solution in isobutanol
[4] Aromatic hydrocarbon mixture, boiling range 182–203° C. (Solvesso® 150) or 161–178° C. (Solvesso® 100); manufacturer ESSO
[5] Aliphatic hydrocarbon mixture, boiling range 145–200° C.; manufacturer Shell 1% in Solvesso® 150[4]; manufacturer Bayer AG 1.7%, based on the solids content of the varnish, of the compound to be tested are added to the varnish. Some further varnish samples are produced which, in addition to the novel compound, contain 1% of the compound

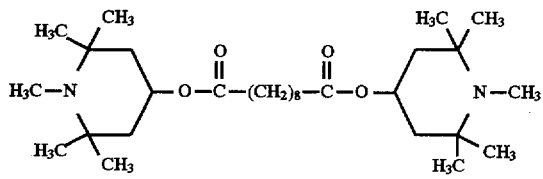

(compound A) based on the solids content of the varnish. The comparison is a varnish containing no light stabilizer.

The varnish is thinned to sprayable consistency with Solvesso® 100 and sprayed onto a prepared aluminium sheet (coil coat, filler, silver-metallic base coat) and baked at 130° C. for 30 minutes, giving a dry film thickness of 40–50 μm of varnish.

The samples are then weathered in an Atlas UVCON® weathering unit (UVB-313 lamps) in a cycle of UV irradiation at 70° C. for 8 hours and condensation at 50° C. for 4 hours.

The surface gloss (20° gloss as per DIN 67530) of the samples is measured at regular intervals. In addition, the surface is assessed for cracking. The results are shown in Table B1.

TABLE B1

| | 20° gloss before and during weathering | | | | | |
|---|---|---|---|---|---|---|
| | | 20° gloss after weathering | | | | Cracking |
| Stabilizer | 0 h | 800 h | 1200 h | 1600 h | 2400 h | after |
| none | 87 | 70 | 46 | 1 | | 1600 h |
| (2) | 87 | 87 | 86 | 55 | 3 | 2000 h |
| (7) | 86 | 84 | 83 | | | |
| (8) | 87 | 87 | 83 | | | |
| (8×) | 87 | 87 | 86 | 68 | 6 | 2000 h |
| (2) + (A) | 88 | 90 | 87 | 87 | 86 | |
| (7) + (A) | 86 | 86 | 86 | 85 | 85 | |
| (8) + (A) | 88 | 87 | 87 | 87 | 86 | |
| (8×) + (A) | 87 | 87 | 87 | 87 | 87 | |

The samples stabilized in accordance with the invention have significantly better weathering stability (gloss retention, cracking resistance) than the unstabilized comparative sample. A considerable further improvement is achieved by the additional use of compound A.

EXAMPLE B2

Stabilization with a UVA combination

The novel compounds listed in Table B2 are incorporated into a varnish and tested as described in Example B1, but, in addition to the stated amount of the novel compound to be tested, a mixture of 85 parts by weight of a further UV absorber (UVA) of the formula

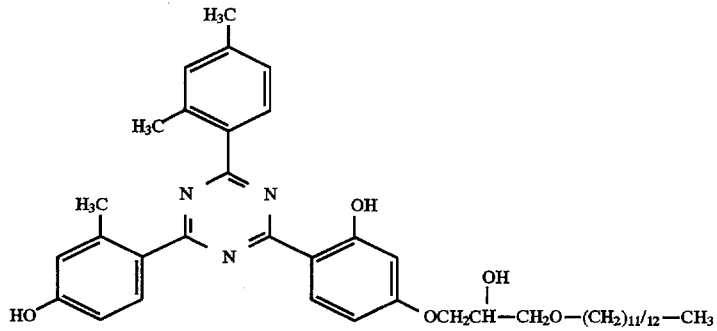

(compound B; isomer mixture containing $C_{12}$- and $C_{13}$alkyl radicals) and 15 parts by weight of 1-methoxy-2-propanol is additionally added to the varnish (amounts in each case based on the solids content of the varnish).

The results are shown in Table B2.

TABLE B2

| | 20° gloss before and during weathering | | | | | |
|---|---|---|---|---|---|---|
| | | 20° gloss after weathering | | | | Cracking |
| Stabilizer | 0 h | 800 h | 1200 h | 1600 h | 2400 h | after |
| none | 87 | 70 | 46 | 1 | | 1600 h |
| 0.85% (8) +1% (B) | 87 | 89 | | | | |
| 0.85% (8) +1% (B) +1% (A) | 88 | 90 | 88 | 88 | 87 | |

TABLE B2-continued

| | 20° gloss before and during weathering | | | | | |
|---|---|---|---|---|---|---|
| | | 20° gloss after weathering | | | | Cracking |
| Stabilizer | 0 h | 800 h | 1200 h | 1600 h | 2400 h | after |
| 1% (8) +0.82% (B) +1% (A) | 87 | 90 | 81 | 79 | 86 | |

EXAMPLE B3

Stabilization of a 2-component polyurethane varnish

A varnish is prepared from the following two components:

Component 1:

| | |
|---|---|
| 28.8% | of Desmophen ® A VP LS 2051 (75% in xylene)[1] |
| 13.4% | of Desmophen ® VP LS 2971 (80% in butyl acetate)[1] |
| 0.5% | of Baysilon OL 17 (10% in xylene)[2] |
| 0.5% | of Modaflow (1% in xylene)[3] |
| 33.5% | of a 1:1 mixture of 1-methoxypropyl acetate and Solvent Naphtha 100 |

Component 2:

| | |
|---|---|
| 23.5% | of Desmodur ® N 3390 (90% in 1:1 mixture of butyl acetate/Solvent Naphtha 100)[4] |
| 100.0% | |

[1] Polyol (Bayer AG)
[2] Flow-control agent (Bayer AG)
[3] Flow-control agent (Monsanto)
[4] Isocyanurate (Bayer AG)

The novel compounds are incorporated into the solvent component of component 1 together with costabilizers (A) and/or (B) as described in Examples B1 and B2. For comparative purposes, an unstabilized varnish sample is prepared. The varnish is applied to a prepared aluminium sheet (electrocoating, aqueous silver-metallic base coat) and baked at 130° C. for 30 minutes, giving a dry film thickness of approx. 45 μm.

The weathering is carried out in a Xenon Weather-O-Meter (CAM 180).

The surface gloss (20° gloss as per DIN 67530) of the samples is measured at regular intervals. The results are shown in Table B3.

TABLE B3

| | 20° gloss before and during weathering | | | |
|---|---|---|---|---|
| | | 20° gloss after weathering | | |
| Stabilizer | 0 h | 400 h | 800 h | 1200 h |
| none | 88 | 50 | 31 | |
| 1.7% (8) + 1% (A) | 88 | 87 | 87 | 88 |
| 0.85% (8) +1% (A) + 1% (B) | 88 | 86 | 87 | 88 |

EXAMPLE B4

A gelatin layer containing silver bromide, a magenta coupler and a stabilizer is applied to a polyethylene base material. A further gelatin layer contains a UV absorber (UVA) of the formula I; the number in Table B4 relates to the list reproduced at the outset.

The gelatin layers contain the following components (per $m^2$ of base material):

| Component | AgBr layer | UV filter |
|---|---|---|
| Gelatin | 5.15 g | 1.2 |
| Curing agent | 300 mg | 40 mg |
| Wetting agent | 85 mg | 100 mg |
| Silver bromide | 520 mg* | — |
| | 260 mg** | — |
| Tricresyl phosphate | A | 510 mg |
| Magenta coupler | 0.535 mmol | — |
| UV absorber | — | 220 mg |
| Stabilizer | B | — |

*on use of tetraequivalent couplers,
**on use of diequivalent couplers
A (amount of oil) = 50% of the amount of magenta coupler,
B (amount of stabilizer) = 35% of the amount of magenta coupler The curing agent used is a solution of the potassium salt of 2,4-dichloro-6-hydroxytriazine, and the wetting agent used is the sodium salt of diisobutylnaphthalenesulfonic acid.

A step wedge having a density difference of 0.30 logE per step is exposed onto each of the resultant samples and subsequently processed in accordance with the manufacturer's instructions by the Kodak RA 4 process for negative colour papers.

After exposure and processing, the remission density in green for the magenta step is measured at a density of between 0.9 and 1.1 of the wedge. The wedge is then exposed in an Atlas exposure unit with a total of 30 $kJ/cm^2$, and the remission density is re-measured. The drop in dye density ($-\Delta D_G$ in %) is shown in Table B4.

TABLE B4:

| Drop in dye density $-\Delta D_G$ after exposure | | | |
|---|---|---|---|
| Magenta coupler (mg) | Stabilizer (mg) | UVA No. (mg) | $-\Delta D_G$ |
| M-2 (417) | ST-8 (144) | none | 79% |
| M-2 (417) | ST-8 (144) | 2 (220) | 40% |
| M-2 (417) | ST-8 (144) | 10 (220) | 42% |
| M-2 (417) | ST-8 (144) | 13 (220) | 43% |
| M-5 (253) | ST-11 (88,6) | none | 52% |
| M-5 (253) | ST-11 (88,6) | 2 (220) | 36% |
| M-5 (253) | ST-11 (88,6) | 10 (220) | 36% |
| M-5 (253) | ST-11 (88,6) | 13 (220) | 39% |
| M-5 (253) | ST-11*, ST-9* | none | 45% |
| M-5 (253) | ST-11*, ST-9* | 2 (220) | 37% |
| M-5 (253) | ST-11*, ST-9* | 10 (220) | 36% |
| M-5 (253) | ST-16 (88.6) | none | 70% |
| M-5 (253) | ST-16 (88.6) | 2 (220) | 54% |
| M-5 (253) | ST-16 (88.6) | 10 (220) | 56% |
| M-5 (253) | ST-16 (88.6) | 13 (220) | 54% |
| M-6 (306) | ST-1 (107) | none | 24% |
| M-6 (306) | ST-1 (107) | 2 (220) | 19% |
| M-6 (306) | ST-1 (107) | 10 (220) | 19% |
| M-6 (306) | ST-1 (107) | 13 (220) | 17% |
| M-6 (306) | ST-4 (107) | none | 26% |
| M-6 (306) | ST-4 (107) | 2 (220) | 17% |
| M-6 (306) | ST-4 (107) | 10 (220) | 17% |
| M-6 (306) | ST-4 (107) | 13 (220) | 18% |
| M-6 (306) | ST-16 (107) | none | 31% |
| M-6 (306) | ST-16 (107) | 2 (220) | 26% |
| M-6 (306) | ST-16 (107) | 10 (220) | 26% |
| M-6 (306) | ST-16 (107) | 13 (220) | 27% |

*per 44.3 mg

The mixture of a novel UV absorber and a stabilizer produces a smaller drop in magenta density than in a sample containing no UV absorber.

EXAMPLE B5

The procedure is as described in Example B4, but no stabilizer is added and a cyan coupler is used. The composition of the gelatin layers (per $m^2$) is as follows:

| Component | AgBr layer | UV filter |
|---|---|---|
| Gelatin | 5.15 g | 1.2 g |
| Curing agent | 300 mg | 40 mg |
| Wetting agent | 170 mg | 100 mg |
| Silver bromide | 260 mg | — |
| Tricresyl phosphate | — | 510 mg |
| Dibutyl phthalate | A | — |
| Cyan coupler | 0.535 mmol | — |
| UV absorber | — | 220 mg |

A (amount of oil) = 1.5 × the amount of cyan coupler

After exposure and processing as described in Example B4, the remission density in red for the cyan step is measured at a density of between 0.9 and 1.1 of the wedge. The wedge is then exposed in an Atlas exposure unit with a total of 30 kJ/$cm^2$, and the remission density is re-measured. The drop in dye density ($-\Delta D_R$ in %) is shown in Table B5.

TABLE B5

Drop in dye density $-\Delta D_R$ after exposure

| Cyan coupler (mg) | UVA No. (mg) | $\Delta D_R$ |
|---|---|---|
| E-1 (264) | none | 15% |
| E-1 (264) | 2 (220) | 11% |
| E-1 (264) | 10 (220) | 10% |
| E-1 (264) | 13 (220) | 11% |
| E-2 (272) | none | 20% |
| E-2 (272) | 2 (220) | 17% |
| E-2 (272) | 10 (220) | 17% |
| E-2 (272) | 13 (220) | 17% |
| E-5 (358) | none | 31% |
| E-5 (358) | 2 (220) | 23% |
| E-5 (358) | 10 (220) | 23% |
| E-5 (358) | 13 (220) | 23% |
| E-6 (331) | none | 35% |
| E-6 (331) | 2 (220) | 27% |
| E-6 (331) | 10 (220) | 28% |
| E-6 (331) | 13 (220) | 27% |

The novel UV absorbers produce a smaller drop in the density of the cyan dye than a sample containing no UV absorber.

EXAMPLE B6

The procedure is as in Example B4, but no stabilizer is added and a yellow coupler is used.

The composition of the gelatin layers (per $m^2$) is as follows:

| Component | AgBr layer | UV filter |
|---|---|---|
| Gelatin | 5.15 g | 1.2 g |
| Curing agent | 300 mg | 40 mg |
| Wetting agent (anionic) | 340 mg | 100 mg |
| Silver bromide | 520 mg | — |
| Tricresyl phosphate | — | 510 mg |
| Dibutyl phthalate | A | — |
| Yellow coupler | 1.07 mmol | — |
| UV absorber | — | 220 mg |

A (amount of oil) = 33% of the amount of yellow coupler

After exposure and processing as described in Example B4, the remission density in blue for the yellow step is measured at a density of between 0.9 and 1.1 of the wedge. The wedge is then exposed in an Atlas exposure unit with a total of 45 kJ/$cm^2$, and the remission density is re-measured. The drop in dye density ($-\Delta D_B$ in %) is shown in Table B6.

TABLE B6

Drop in dye density $-\Delta D_B$ after exposure

| Yellow coupler (mg) | UVA No. (mg) | $-\Delta D_B$ |
|---|---|---|
| Y-2 (859) | none | 35% |
| Y-2 (859) | 2 (220) | 19% |
| Y-2 (859) | 10 (220) | 19% |
| Y-2 (859) | 13 (220) | 20% |
| Y-3 (973) | none | 64% |
| Y-3 (973) | 2 (220) | 31% |
| Y-3 (973) | 10 (220) | 29% |
| Y-3 (973) | 13 (220) | 32% |
| Y-8 (927) | none | 64% |
| Y-8 (927) | 2 (220) | 31% |
| Y-8 (927) | 10 (220) | 31% |
| Y-8 (927) | 13 (220) | 34% |
| Y-9 (854) | none | 54% |
| Y-9 (854) | 2 (220) | 29% |
| Y-9 (854) | 10 (220) | 30% |
| Y-9 (854) | 13 (220) | 32% |

The novel UV absorbers produce a smaller drop in yellow dye density than a sample containing no UV absorber.

EXAMPLE B7

The procedure is as in Example B4.

The amounts of magenta coupler and stabilizer are shown in Table B7.

For comparative purposes, a UV absorber of the prior art is also employed in some samples; this is the following compound:

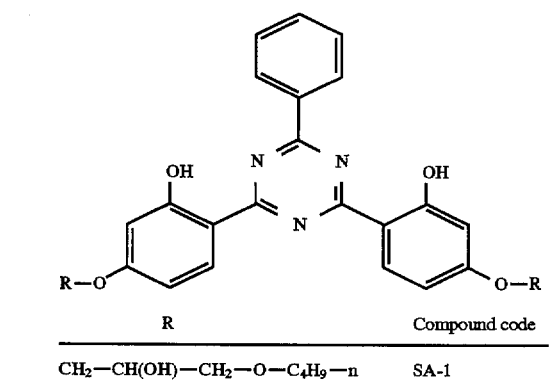

| R | Compound code |
|---|---|
| $CH_2-CH(OH)-CH_2-O-C_4H_9-n$ | SA-1 |

The remission density in blue for yellowing is measured. The wedge is exposed in an Atlas exposure unit with a total of 45 kJ/$cm^2$, and the remission density at 406 nm is then measured. Table B7 shows the yellow value ($D_{406}$) determined.

TABLE B7

Yellow value $D_{406}$ after exposure

| Magenta coupler (mg) | Stabilizer (mg) | UVA No. (mg) | $100 \cdot D_{406}$ |
|---|---|---|---|
| M-1 (329) | ST-4 (118) | none | 31 |
| M-1 (329) | ST-4 (118) | 2 (220) | 45 |

TABLE B7-continued

| | Yellow value $D_{406}$ after exposure | | |
|---|---|---|---|
| Magenta coupler (mg) | Stabilizer (mg) | UVA No. (mg) | $100 \cdot D_{406}$ |
| M-1 (329) | ST-4 (118) | SA-1 (220) | 47 |
| M-1 (329) | ST-4 (118) | 10 (220) | 42 |
| M-1 (329) | ST-4 (118) | 13 (220 | 43 |

Use of the novel UV absorbers as a mixture with a stabilizer results in a lower yellow value compared with a structurally similar UV absorber of the prior art.

EXAMPLE B8

The procedure is as in Example B4, but
① exposure is only carried out with 30 kJ/cm²
② the UV absorber of the invention (110 mg) is mixed with hydroxybenzotriazole (110 mg)
The following hydroxybenzotriazoles are employed:

| HBT No. | $T_1$ | $T_2$ | $T_3$ |
|---|---|---|---|
| HBT-5 | $C(CH_3)_2C_2H_5$ | $C(CH_3)_2C_2H_5$ | H |
| HBT-8 | $C(CH_3)_3$ | $CH_2CH_2COOC_8H_{17}$ (isomers) | Cl |
| HBT-10 | $C_{12}H_{25}$ | $CH_3$ | H |

The drop in dye density ($-\Delta D_G$ in %) is shown in Table B8.

TABLE B8

| | Drop in dye density $-\Delta D_G$ after exposure | | |
|---|---|---|---|
| Magenta coupler (mg) | Stabilizer (mg) | UVA | $-\Delta D_G$ |
| M-2 (417) | ST-8 (144) | none | 79% |
| M-2 (417) | ST-8 (144) | 2, HBT-10 | 47% |
| M-2 (417) | ST-8 (144) | 10, HBT-10 | 45% |
| M-2 (417) | ST-8 (144) | 13, HBT-10 | 49% |
| M-2 (417) | ST-8 (144) | 2, HBT-5 | 43% |
| M-2 (417) | ST-8 (144) | 10, HBT-5 | 46% |
| M-6 (306) | ST-4 (128) | none | 26% |
| M-6 (306) | ST-4 (128) | 2, HBT-10 | 19% |
| M-6 (306) | ST-4 (128) | 10, HBT-10 | 18% |
| M-6 (306) | ST-4 (128) | 13, HBT-10 | 19% |

Use of the novel UV absorbers as a mixture with a hydroxybenzotriazole produces a smaller drop in magenta dye density.

EXAMPLE B9

A gelatin layer containing silver bromide, a cyan coupler and a UV absorber of the formula (I) is applied to a polyethylene base material. The gelatin layer contains the following components (per m² of base material)

| Component | AgBr layer |
|---|---|
| Gelatin | 5.15 g |
| Curing agent | 300 mg |
| Wetting agent (anionic) | 170 mg |
| Silver bromide | 260 mg |
| Tricresyl phosphate | A |
| Cyan coupler | 0.535 mmol |
| UV absorber | see Table 6 |

A (amount of oil) = 1.5 × the amount of cyan coupler

After exposure and processing as described in Example B4, the remission density in red for the cyan step is meausred at a density of between 0.9 and 1.1 of the wedge. The wedge is then exposed in an Atlas exposure unit with 30 kJ/cm², and the remission density is re-measured. The drop in dye density ($-\Delta D_R$ in %) is shown in Table B9.

TABLE B9

| Drop in dye density $-\Delta D_R$ after exposure | | |
|---|---|---|
| Cyan coupler (mg) | UVA No. (mg) | $-\Delta D_R$ |
| E-5 (358) | none | 31% |
| E-5 (358) | 2 (358) | 19% |
| E-5 (358) | 13 (358) | 22% |
| E-6 (321) | none | 35% |
| E-6 (321) | 2 (321) | 24% |
| E-6 (321) | 13 (321) | 23% |

Use of the novel UV absorbers produces a smaller drop in cyan dye density than a sample containing no UVA.

EXAMPLE B10

The procedure is as in Example B6, but the UV absorber of the invention (110 mg) is mixed with a hydroxybenzotriazole (110 mg) as indicated in Example B8.

The drop in dye density ($-\Delta D_B$ in %) is shown in Table B10.

TABLE B10

| Drop in dye density $-\Delta D_B$ after exposure | | |
|---|---|---|
| Yellow coupler (mg) | UVA | $-\Delta D_B$ |
| Y-8 (927) | none | 43% |
| Y-8 (927) | 2, HBT-10 | 24% |
| Y-8 (927) | 10, HBT-10 | 24% |
| Y-8 (927) | 13, HBT-10 | 25% |
| Y-8 (927) | 2, HBT-8 | 24% |
| Y-8 (927) | 10, HBT-8 | 23% |
| Y-8 (927) | 13, HBT-8 | 25% |

With the aid of the novel UV absorbers mixed with a hydroxybenzotriazole, a smaller drop in yellow dye density is achieved than in a sample containing no UVA.

EXAMPLE B11

The procedure is as in Example B6, but a stabilizer is additionally added.

The amounts of yellow coupler and stabilizer and drop in dye density ($-\Delta D_B$ in %) are shown in Table B11.

TABLE B11

Drop in dye density $-\Delta D_B$ after exposure

| Yellow coupler (mg) | Stabilizer (mg) | UVA No. (mg) | $-\Delta D_B$ |
|---|---|---|---|
| Y-2 (859) | ST-12 (258) | none | 19% |
| Y-2 (859) | ST-12 (258) | 2 (220) | 10% |
| Y-2 (859) | ST-12 (258) | 10 (220) | 10% |
| Y-2 (859) | ST-12 (258) | 13 (220) | 10% |
| Y-2 (859) | ST-13 (258) | none | 22% |
| Y-2 (859) | ST-13 (258) | 2 (220) | 12% |
| Y-2 (859) | ST-13 (258) | 10 (220) | 12% |
| Y-2 (859) | ST-13 (258) | 13 (220) | 13% |
| Y-3 (973) | ST-12 (292) | none | 35% |
| Y-3 (973) | ST-12 (292) | 2 (220) | 15% |
| Y-3 (973) | ST-12 (292) | 10 (220) | 15% |
| Y-3 (973) | ST-12 (292) | 13 (220) | 16% |
| Y-8 (927) | ST-12 (278) | none | 32% |
| Y-8 (927) | ST-12 (278) | 2 (220) | 12% |
| Y-8 (927) | ST-12 (278) | 10 (220) | 12% |
| Y-8 (927) | ST-12 (278) | 13 (220) | 14% |
| Y-8 (927) | ST-15 (278) | none | 44% |
| Y-8 (927) | ST-15 (278) | 2 (220) | 20% |
| Y-8 (927) | ST-15 (278) | 10 (220) | 20% |
| Y-8 (927) | ST-15 (278) | 13 (220) | 22% |
| Y-9 (854) | ST-12 (256) | none | 42% |
| Y-9 (854) | ST-12 (256) | 2 (220) | 15% |
| Y-9 (854) | ST-12 (256) | 10 (220) | 17% |
| Y-9 (854) | ST-12 (256) | 13 (220) | 16% |
| Y-9 (854) | ST-12 (256) | none | 39% |
| Y-9 (854) | ST-12 (256) | 2 (220) | 20% |
| Y-9 (854) | ST-12 (256) | 10 (220) | 20% |
| Y-9 (854) | ST-12 (256) | 13 (220) | 21% |

With the aid of the novel UV absorbers mixed with a stabilizer, a smaller drop in yellow dye density is achieved than in a sample containing no UVA.

EXAMPLE B12

The procedure is as in Example B11, but the UV absorber of the invention (110 mg) is mixed with a hydroxybenzotriazole (110 mg) as indicated in Example B8.

The drop in dye density ($-\Delta D_B$ in %) is shown in Table B12.

TABLE B12

Drop in dye density $-\Delta D_B$ after exposure

| Yellow coupler (mg) | Stabilizer(mg) | UVA | $-\Delta D_B$ |
|---|---|---|---|
| Y-8 (927) | ST-12 (278) | none | 16% |
| Y-8 (927) | ST-12 (278) | 2, HBT-8 | 9% |

With the aid of the novel UV absorbers mixed with a stabilizer and a hydrobenzotriazole, a smaller drop in yellow dye density is achieved than in a sample containing no UVA.

EXAMPLE B13

A photographic material having the following layer structure is produced:

Protective layer
Red-sensitive layer
Second gelatin interlayer
Green-sensitive layer
First gelatin interlayer
Blue-sensitive layer
Polyethylene base The gelatin layers comprise the following components (per $m^2$ of base material):

| Blue-sensitive layer | |
|---|---|
| Yellow coupler Y-2 | 859 mg |
| Tricresyl phosphate | 286 mg |
| Gelatin | 5.15 g |
| Curing agent | 300 mg |
| Wetting agent | 340 mg |
| AgBr | 520 mg |
| First gelatin interlayer | |
| Gelatin | 3.90 g |
| Curing agent | 230 mg |
| Wetting agent | 65 mg |
| Green-sensitive layer | |
| Magenta coupler M-6 | 306 mg |
| Tricresyl phosphate | 153 mg |
| Gelatin | 5,15 g |
| Curing agent | 300 mg |
| Wetting agent | 85 mg |
| AgBr | 260 mg |
| Stabilizer | 107 mg |
| Second gelatin interlayer | |
| Gelatin | 3.90 g |
| Curing agent | 230 mg |
| Wetting agent | 65 mg |
| Red-sensitive layer | |
| Cyan coupler E-6 | 331 mg |
| Tricresyl phosphate | 496 mg |
| Gelatin | 5.15 g |
| Curing agent | 300 mg |
| Wetting agent | 170 mg |
| AgBr | 260 mg |

A protective layer is produced with and without UV absorber.

| | with UV absorber | without UV absorber |
|---|---|---|
| Gelatin | 1.2 g | 2.4 g |
| UV absorber | 220 mg | — |
| Tricresyl phosphate | 510 mg | — |
| Curing agent | 40 mg | 80 mg |
| Wetting agent | 100 mg | 200 mg |

The curing agent and wetting agent are the corresponding compounds as in Example B4.

Three step wedges having a density difference of 0.3 kJ per step are exposed onto each of the samples (with blue, green and red light).

The photographic material is then processed by the Kodak RA 4 process for negative colour papers.

After exposure and processing, the remission densities in red for the cyan step, in green for the magenta step and in blue for the yellow step are measured at a density of between 0.9 and 1.1 of the wedges. The wedges are then exposed in an Atlas exposure unit with a total of 15 $kJ/cm^2$, and the remission densities are re-measured.

The remission density in blue for yellowing before and after exposure is also measured for the magenta wedge.

The presence of the UV absorber reduces the drop in cyan, magenta and yellow image dye density and the yellowing.

EXAMPLE B14

A photographic material having the following layer structure is produced:

Top layer
Red-sensitive layer
Second gelatin interlayer
Green-sensitive layer
First gelatin interlayer
Blue-sensitive layer
Polyethylene base The gelatin layers comprise the following components (per $m^2$ of base material):
Blue-sensitive layer
α-(3-Benzyl-4-ethoxyhydantoin-1-yl)-α-pivaloyl-2-chloro-5-[α-(2,4-di-t-amylphenoxy)butanamido]acetanilide (400 mg)
α-(1-Butylphenylurazol-4-yl)-α-pivaloyl-5-(3-dodecanesulfonyl-2-methylpropanamido)-2-methoxyacetamide (400 mg)
Dibutyl phthalate (130 mg)
Dinonyl phthalate (130 mg)
Gelatin (1200 mg)
1,5-Dioxa-3-ethyl-3-[β-(3,5-di-t-butyl-4-hydroxyphenyl)propionyloxymethyl]-8,10-diphenyl-9-thia[5,5]spiroundecane (150 mg)
Bis(1-acryloyl-2,2,6,6-tetramethyl-4-piperidyl) 2,2-bis(3,5-di-t-butyl-4-hydroxybenzyl)malonate (150 mg)
2,4-Di-t-amylphenyl 3,5-di-t-butyl-4-hydroxybenzoate (150 mg)
Poly(N-t-butylacrylamide) (50 mg)
Blue-sensitive silver-chlorobromide emulsion (240 mg)
First gelatin interlayer
Gelatin (1,000 mg)
2,5-Di-t-octylhydroquinone (100 mg)
Hexyl 5-[2,5-dihydroxy-4-(4-hexyloxycarbonyl-1,1-dimethylbutyl)phenyl]-5-methylhexanoate (100 mg)
Dibutyl phthalate (200 mg)
Diisodecyl phthalate (200 mg)
Green-sensitive layer
7-Chloro-2-{2-[2-(2,4-di-t-amylphenoxy)octanamido]-1-methylethyl}-6-methyl-1H-pyrazolo[1,5-b][1,2,4]triazole (100 mg)
6-t-Butyl-7-chloro-3-(3-dodecanesulfonylpropyl)-1H-pyrazolo[5,1-o][1,2,4]triazole (100 mg)
Dibutyl phthalate (100 mg)
Dicresyl phosphate (100 mg)
Trioctyl phosphate (100 mg)
Gelatin (1400 mg)
3,3,3',3'-Tetramethyl-5,5',6,6'-tetrapropoxy-1,1'-spirobiindane (100 mg)
4-(i-Tridecyloxyphenyl)thiomorpholine 1,1-dioxide (100 mg)
4,4'-Butylidenebis(3-methyl-6-t-butylphenol) (50 mg)
2,2'-Isobutylidenebis(4,6-dimethylphenol) (10 mg)
Ethyl 3,5-dichloro-4-(hexadecyloxycarbonyloxy)benzoate (20 mg)
Sodium 3,5-bis[3-(2,4-di-t-amylphenoxy)propylcarbamoyl]benzenesulfinate (20 mg)
Green-sensitive silver chlorobromide emulsion (150 mg)
Second gelatin interlayer
Gelatin (1000 mg)
5-Chloro-2-(3,5-di-t-butyl-2-hydroxyphenyl)-1,2,3-benzotriazole (200 mg)
2-(3-Dodecyl-2-hydroxy-5-methylphenyl)-1,2,3-benzotriazole (200 mg)
Trinonyl phosphate (300 mg)
2,5-Di-t-octylhydroquinone (50 mg)
Hexyl 5-[2,5-dihydroxy-4-(4-hexyloxycarbonyl-1,1-dimethylbutyl)phenyl]-5-methylhexanoate (50 mg)
Red-sensitive layer
2-[α-(2,4-Di-t-amylphenoxy)butanamido]-4,6-di-chloro-5-ethylphenol (150 mg)
2,4-Dichloro-3-ethyl-6-hexadecanamidophenol (150 mg)
4-Chloro-2-(1,2,3,4,5-pentafluorobenzamido)-5-[2-(2,4-di-t-amylphenoxy)-3-methylbutanamido]phenol (100 mg)
Dioctyl phthalate (100 mg)
Dicyclohexyl phthalate (100 mg)
Gelatin (1200 mg)
5-Chloro-2-(3,5-di-t-butyl-2-hydroxyphenyl)-1,2,3-benzotriazole (100 mg)
2-(3-Dodecyl-2-hydroxy-5-methylphenyl)-1,2,3-benzotriazole (100 mg)
2,4-Di-t-amylphenyl 3,5-di-t-butyl-4-hydroxybenzoate (50 mg)
Poly(N-t-butylacrylamide) (300 mg)
N,N-Diethyl-2,4-di-t-amylphenoxyacetamide (100 mg)
2,5-Di-t-octylhydroquinone (50 mg)
Red-sensitive silver chlorobromide emulsion (200 mg)
The top layer is produced with and without UV absorber.
With UV absorber:
2,5-Di-t-octylhydroquinone (20 mg)
Hexyl 5-[2,5-dihydroxy-4-(4-hexyloxycarbonyl-1,1-dimethylbutyl)phenyl]-5-methylhexanoate (20 mg)
Gelatin (400 mg)
Trinonyl phosphate (120 mg)
UV absorber No. (2) (200 mg)
Without UV absorber:
Gelatin (800 mg)
The curing agent used is a solution of the potassium salt of 2,4-dichloro-6-hydroxytriazine, and the wetting agent used is the sodium salt of diisobutylnaphthalenesulfonic acid.

Three step wedges having a density difference of 0.3 kJ per step are exposed onto each of the samples (with blue, green and red light). The photographic material is then processed by the Kodak RA 4 process for negative colour papers.

After exposure and processing, the remission densities in red for the cyan step, in green for the magenta step and in blue for the yellow step are measured at a density of between 0.9 and 1.1 of the wedges. The wedges are then exposed in an Atlas exposure unit with a total of 15 kJ/cm$^2$ and the remission densities are re-measured.

The remission density in blue for yellowing before and after exposure is also measured for the magenta wedge.

The presence of the UV absorber reduces the drop in cyan, magenta and yellow image dye density.

EXAMPLE B15

A gelatin layer having a dry layer thickness of approx. 2 μm and containing a UV absorber (UVA) listed in Table B15 is applied to a transparent polyester base. The structure of the UVA tested as comparison is indicated in Example B7. The gelatin layer contains 1.2 g of gelatin, 40 mg of curing agent (potassium salt of 2,4-dichloro-6-hydroxytriazine), 100 mg of wetting agent (sodium salt of diisobutylnaphthalenesulfonic acid), 510 mg of tricresyl phosphate and 220 mg of UVA per m$^2$. The cured layer is analysed spectrophotometrically; from the data, the specific absorption coefficient ($\epsilon_{sp}$) for the particular wavelength is calculated. High absorption in the vicinity of the UV maximum at approx. 252 nm and very low absorption in the visible region above 400 nm are desired. The results are shown in Table B15.

TABLE B15

| | Specific absorption coefficient ($\epsilon_{sp}$) | | | | | | |
|---|---|---|---|---|---|---|---|
| UVA $\epsilon_{sp}$ | 252 | 390 | 395 | 400 | 405 | 410 | nm |
| 2 | 51614 | 2718 | 855 | 127 | 0 | 0 | |
| SA-1 | 42709 | 5536 | 2991 | 1586 | 791 | 509 | |

The comparison shows that novel UVA (2) surprisingly absorbs more strongly in the UV region than does a comparable UVA from the prior an (SA-1), while (2) exhibits virtually no absorption at the edge of the visible region.

EXAMPLE B16

The procedure is as in Example B4, but a yellow coupler is used and the hydrophobic polymer described below is additionally used in the blue-sensitive layer.

The composition of the gelatin layers (amounts in each case per $m^2$) is as follows:

| Component | AgBr layer | UV filter |
|---|---|---|
| Gelatin | 5.15 g | 1.2 g |
| Curing agent | 300 mg | 40 mg |
| Wetting agent (anionic) | 340 mg | 100 mg |
| Silver bromide | 520 mg | — |
| Dibutyl phthalate | 285 mg | — |
| Yellow coupler Y-9 | 854 mg | — |
| UV absorber | — | 220 mg |

After exposure and processing as described in Example B4, the remission density in blue for the yellow step is measured at a density of between 0.9 and 1.1 of the wedge. The wedge is then exposed in an Atlas exposure unit with a total of 30 kJ/cm² and the remission density is re-measured. The drop in dye density ($-\Delta D_B$ in %) is shown in Table B16.
P1 is a homopolymer of tert-butylacrylamide;
P2 is a copolymer of dibutyl fumarate and 2-ethylhexyl acrylate;
TCP denotes tricresyl phosphate.

TABLE B16

Drop in dye density $-\Delta D_B$ after exposure

| Filter layer: UVA oil (510 mg) | Polymer (mg) | Yellow coupler layer: Polymer(256 mg) | $-\Delta D_B$ |
|---|---|---|---|
| — | — | — | 34 |
| 2 | TKP | — | 20 |
| 2 | TKP P1 (22) | — | 19 |
| 2 | TKP P2 (22) | — | 21 |
| 2 | TKP P1 (44) | — | 22 |
| 2 | TKP P2 (44) | — | 19 |
| 2 | — P1 (22) | — | 20 |
| 2 | — P2 (22) | — | 21 |
| 2 | — P1 (44) | — | 23 |
| 2 | — P2 (44) | — | 22 |
| 2 | TKP | P1 | 15 |
| 2 | TKP | P2 | 19 |
| 2 | TKP P1 (22) | P1 | 17 |
| 2 | TKP P2 (22) | P1 | 15 |
| 2 | TKP P1 (44) | P1 | 17 |
| 2 | TKP P2 (44) | P1 | 16 |

TABLE B16-continued

Drop in dye density $-\Delta D_B$ after exposure

| Filter layer: UVA oil (510 mg) | Polymer (mg) | Yellow coupler layer: Polymer(256 mg) | $-\Delta D_B$ |
|---|---|---|---|
| 2 | TKP P1 (22) | P2 | 19 |
| 2 | TKP P2 (22) | P2 | 19 |
| 2 | TKP P1 (44) | P2 | 19 |
| 2 | TKP P2 (44) | P2 | 20 |
| 2 | — P1 (22) | P1 | 16 |
| 2 | — P2 (22) | P1 | 15 |
| 2 | — P1 (44) | P1 | 16 |
| 2 | — P2 (44) | P1 | 16 |
| 2 | — P1 (22) | P2 | 20 |
| 2 | — P2 (22) | P2 | 20 |
| 2 | — P1 (44) | P2 | 20 |
| 2 | — P2 (44) | P2 | 21 |

The novel UV absorbers in combination with said polymers exhibit a good protective action for the yellow dye.
What is claimed is:
1. A compound of the formula I

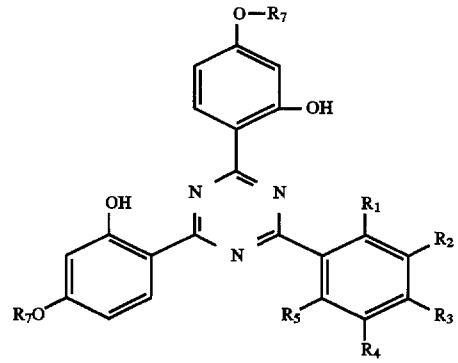

in which $R_1$ and $R_5$, independently of one another, are $C_1$–$C_{12}$alkyl; $R_2$, $R_3$ and $R_4$, independently of one another, are H; $C_1$–$C_{12}$alkyl; $C_2$–$C_6$alkenyl; $C_1$–$C_{12}$alkoxy; $C_2$–$C_{18}$alkenyloxy; halogen; trifluormethyl; $C_7$–$C_{11}$phenylalkyl; phenyl; phenyl which is substituted by $C_1$–$C_{18}$alkyl, $C_1$–$C_{18}$alkoxy or halogen; phenoxy; or phenoxy which is substituted by $C_1$–$C_{18}$alkyl, $C_1$–$C_{18}$alkoxy or halogen;

the two radicals $R_7$ are identical or different and are hydrogen or $C_1$–$C_{18}$alkyl; or are $C_1$–$C_{18}$alkyl which is substituted by OH, $C_1$–$C_{18}$alkoxy, $C_3$–$C_6$alkenyloxy, halogen, —COOH, —COOR$_8$, —CONH$_2$, —CONHR$_9$, —CON(R$_9$)(R$_{10}$), —NH$_2$, —NHR$_9$, —N(R$_9$)(R$_{10}$), —NHCOR$_{11}$, —CN, —OCOR$_{11}$, phenoxy and/or phenoxy which is substituted by $C_1$–$C_{18}$alkyl, $C_1$–$C_{18}$alkoxy or halogen; or the radicals $R_7$ are $C_3$–$C_{50}$alkyl which is interrupted by —O— and may be substituted by OH, phenoxy or $C_7$–$C_{18}$alkylphenoxy; or the radicals $R_7$ are $C_3$–$C_6$alkenyl; glycidyl; $C_5$–$C_{12}$cycloalkyl; $C_5$–$C_{12}$cycloalkyl which is substituted by OH, $C_1$–$C_4$alkyl oder —OCOR$_{11}$; $C_7$–$C_{11}$phenylalkyl which is unsubstituted or substituted by OH, Cl or CH$_3$; $C_4$–$C_{14}$alkenyl which is substituted by OH or —OCOR$_{11}$; —CO—R$_{12}$ or —SO$_2$—R$_{13}$;

$R_8$ is $C_1$–$C_{18}$alkyl; $C_3$–$C_{18}$alkenyl; $C_3$–$C_{50}$alkyl which is interrupted by O, NH, NR$_9$ or S and/or is substituted by OH; $C_1$–$C_4$alkyl which is substituted by —P(O)(OR$_{14}$)$_2$, —N(R$_9$)(R$_{10}$) or —OCOR$_{11}$ and/or OH; glycidyl; $C_5$–$C_{12}$cycloalkyl; phenyl; $C_7$–$C_{14}$alkylphenyl or $C_7$–$C_{11}$phenylalkyl;

$R_9$ and $R_{10}$, independently of one another, are $C_1$–$C_{12}$alkyl; $C_3$–$C_{12}$alkoxyalkyl; $C_4$–$C_{16}$dialkylaminoalkyl or $C_5$–$C_{12}$cycloalkyl, or $R_9$ and $R_{10}$ together are $C_3$–$C_9$alkylene or -oxaalkylene or -azaalkylene; $R_{11}$ is $C_1$–$C_{18}$alkyl, $C_5$–$C_{12}$cycloalkyl or phenyl; or is $C_3$–$C_{50}$alkyl which is interrupted by —O— and may be substituted by OH;

$R_{12}$ is $C_1$–$C_{18}$alkyl; phenyl; $C_5$–$C_{12}$cycloalkyl; $C_1$–$C_{12}$alkoxy; phenoxy; $C_1$–$C_{12}$alkylamino; phenylamino; tolylamino or naphthylamino;

$R_{13}$ is $C_1$–$C_{12}$alkyl; phenyl; naphthyl or $C_7$–$C_{14}$alkylphenyl; and $R_{14}$ is $C_1$–$C_{12}$alkyl or phenyl.

2. A compound of the formula I according to claim 1, in which $R_1$ and $R_5$, independently of one another, are $C_1$–$C_4$alkyl;

$R_2$, $R_3$ and $R_4$, independently of one another, are H, $C_1$–$C_{12}$alkyl, $C_2$–$C_6$alkenyl, $C_1$–$C_{12}$alkoxy, Cl, F, phenyl or phenoxy.

3. A compound of the formula I according to claim 1, in which $R_7$ is hydrogen or $C_1$–$C_{18}$alkyl; or $C_1$–$C_{12}$alkyl which is substituted by OH, $C_1$–$C_{18}$alkoxy, $C_3$–$C_6$alkenyloxy, —Cl, —F, —COOH, —COOR$_8$, —CONHR$_9$, —CON(R$_9$)(R$_{10}$), —NH$_2$, —NHR$_9$, —N(R$_9$)(R$_{10}$), —NHCOR$_{11}$, —CN, —OCOR$_{11}$, phenoxy and/or phenoxy which is substituted by $C_1$–$C_{18}$alkyl, $C_1$–$C_{18}$alkoxy or halogen; or the radicals $R_7$ are $C_3$–$C_{50}$alkyl which is interrupted by —O— and may be substituted by OH, phenoxy or $C_7$–$C_{18}$alkylphenoxy; or the radicals $R_7$ are $C_3$–$C_6$alkenyl; glycidyl; $C_5$–$C_{12}$cycloalkyl; $C_5$$C_{12}$cycloalkyl which is substituted by OH, $C_1$–$C_4$alkyl or —OCOR$_{11}$; $C_7$–$C_{11}$phenylalkyl which is unsubstituted or substituted by OH, Cl or CH$_3$; $C_4$–$C_{14}$alkenyl which is substituted by OH or —OCOR$_{11}$; or —CO—R$_{12}$;

$R_8$ is $C_1$–$C_{18}$alkyl; $C_3$–$C_{18}$alkenyl; $C_3$–$C_{50}$alkyl which is interrupted by O and/or substituted by OH; $C_1$–$C_4$alkyl which is substituted by —P(O)(OR$_{14}$)$_2$, —N(R$_9$)(R$_{10}$) or —OCOR$_{11}$ and/or OH; glycidyl; $C_5$–$C_{12}$cycloalkyl; phenyl or $C_7$–$C_{11}$phenylalkyl;

$R_{11}$ is $C_1$–$C_{18}$alkyl, cyclohexyl or phenyl; or $C_3$–$C_{50}$alkyl which is interrupted by —O— and may be substituted by OH; and $R_{12}$ is $C_1$–$C_{18}$alkyl; phenyl; cyclohexyl; $C_1$–$C_{12}$alkoxy; phenoxy.

4. A compound of the formula I according to claim 1, in which $R_7$ is hydrogen or $C_1$–$C_{18}$alkyl; or $C_1$–$C_{18}$alkyl which is substituted by OH, $C_1$–$C_{18}$alkoxy, $C_3$–$C_6$alkenyloxy, phenoxy, —COOR$_8$, —CONHR$_9$, —CON(R$_9$)(R$_{10}$) and/or —OCOR$_{11}$; or $R_7$ is —(CH$_2$CHR$_{15}$—O)$_n$—R$_{18}$ or —CH$_2$—CH(OH)—CH$_2$—O—(CH$_2$CHR$_{15}$—O)$_n$—R$_{18}$, where n is a number in the range from 1 to 12; or the radicals $R_7$ are $C_3$–$C_6$alkenyl; glycidyl;

$C_5$–$C_{12}$cycloalkyl; $C_5$–$C_{12}$cycloalkyl which is substituted by OH or —OCOR$_{11}$;

$C_7$–$C_{11}$phenylalkyl; $C_4$$C_{14}$alkenyl which is substituted by OH or —OCOR$_{11}$; or —CO—R$_{12}$;

$R_8$ is $C_1$–$C_{18}$alkyl; $C_3$–$C_8$alkenyl; $C_3$–$C_{50}$alkyl which is interrupted by O and/or substituted by OH; $C_1$–$C_4$alkyl which is substituted by —P(O)(OR$_{14}$)$_2$ or —OCOR$_{11}$ and/or OH;

$C_5$–$C_{12}$cycloalkyl; phenyl or $C_7$–$C_{11}$phenylalkyl;

$R_{11}$ is $C_1$–$C_8$alkyl, cyclohexyl or phenyl;

$R_{12}$ is $C_1$–$C_{18}$alkyl or phenyl;

$R_{14}$ is $C_1$–$C_4$alkyl;

$R_{15}$ is H or methyl; and $R_{18}$ is H, $C_1$–$C_{18}$alkyl, phenyl or $C_7$–$C_{18}$alkylphenyl.

5. A compound according to claim 1, in which $R_1$ and $R_5$, independently of one another, are $C_1$–$C_4$alkyl;

$R_2$, $R_3$ and $R_4$, independently of one another, are H, $C_1$–$C_6$alkyl, allyl, $C_1$–$C_4$alkoxy, Cl, F or phenyl.

6. A compound according to claim 1, in which $R_1$ and $R_5$ are methyl;

$R_2$, $R_3$ and $R_4$ are H, $C_1$–$C_4$alkyl, $C_1$–$C_4$alkoxy, —Cl or phenyl; the radicals $R_7$ are identical and are hydrogen or $C_1$–$C_{18}$alkyl; or $C_1$–$C_{12}$alkyl which is substituted by OH, $C_1$–$C_{18}$alkoxy, $C_3$–$C_5$alkenyloxy, phenoxy, —COOR$_8$ and/or —OCOR$_{11}$; or $R_7$ is —(CH$_2$CHR$_{15}$—O)$_n$—R$_{18}$ or —CH$_2$—CH(OH)—CH$_2$—O—(CH$_2$CHR$_{15}$—O)$_n$—R$_{18}$, where n is a number in the range from 1 to 12; or the radicals $R_7$ are $C_5$–$C_{12}$cycloalkyl;

$C_5$–$C_{12}$cycloalkyl which is substituted by OH; or OH-substituted $C_4$–$C_{14}$alkenyl;

$R_8$ is $C_1$–$C_{12}$alkyl;

$R_{11}$ is $C_1$–$C_4$alkyl; and $R_{18}$ is H or $C_1$–$C_8$alkyl.

* * * * *